(12) United States Patent
Kim et al.

(10) Patent No.: US 12,428,446 B2
(45) Date of Patent: Sep. 30, 2025

(54) PEPTIDE COMPOUND OR PHARMACEUTICALLY ACCEPTABLE SALT THEREOF

(71) Applicant: Eyebio Korea, Busan (KR)

(72) Inventors: Yoo Seok Kim, Gyeonggi-do (KR); Myoung Hwan Kim, Gyeonggi-do (KR); Young In Kim, Gyeonggi-do (KR); Taek Joo Lim, Gyeonggi-do (KR); Hyeong Joon Lim, Gyeonggi-do (KR); Jee Young Kim, Busan (KR); Eun Young Park, Busan (KR)

(73) Assignee: Eyebio Korea, Busan (KR)

( * ) Notice: Subject to any disclaimer, the term of this patent is extended or adjusted under 35 U.S.C. 154(b) by 0 days.

(21) Appl. No.: 17/613,176

(22) PCT Filed: May 20, 2020

(86) PCT No.: PCT/KR2020/006594
§ 371 (c)(1),
(2) Date: Nov. 22, 2021

(87) PCT Pub. No.: WO2020/235932
PCT Pub. Date: Nov. 26, 2020

(65) Prior Publication Data
US 2024/0228538 A1    Jul. 11, 2024

(30) Foreign Application Priority Data
May 21, 2019  (KR) .......... 10-2019-0059628

(51) Int. Cl.
| | | |
|---|---|---|
| *A61K 38/00* | (2006.01) | |
| *A61K 8/64* | (2006.01) | |
| *A61P 29/00* | (2006.01) | |
| *A61Q 19/00* | (2006.01) | |
| *C07K 7/06* | (2006.01) | |

(52) U.S. Cl.
CPC .......... *C07K 7/06* (2013.01); *A61K 8/64* (2013.01); *A61P 29/00* (2018.01); *A61Q 19/00* (2013.01); *A61K 38/00* (2013.01); *A61K 2800/10* (2013.01)

(58) Field of Classification Search
CPC ..... A23L 33/18; A61K 2800/10; A61K 38/00; A61K 8/64; A61P 29/00; A61Q 19/00; C07K 7/06; A23V 2002/00; A23V 2200/30; A23V 2250/55
See application file for complete search history.

(56) References Cited

U.S. PATENT DOCUMENTS

| | | | |
|---|---|---|---|
| 6,037,135 A | 3/2000 | Kubo et al. | |
| 10,532,084 B2 | 1/2020 | Yang | |
| 2009/0074672 A1 | 3/2009 | Faris et al. | |
| 2011/0177491 A1 | 7/2011 | Kamiie et al. | |
| 2015/0160201 A1 | 6/2015 | Kane et al. | |
| 2016/0215018 A1 | 7/2016 | Yang et al. | |
| 2024/0352071 A1* | 10/2024 | Kim | A61Q 19/00 |

FOREIGN PATENT DOCUMENTS

| | | | | |
|---|---|---|---|---|
| AU | 2018281617 B2 * | 6/2022 | ............. | A61K 38/00 |
| CN | 107814840 A | 3/2018 | | |
| CN | 108727472 A | 11/2018 | | |
| EP | 0 489 089 B1 | 6/1996 | | |
| JP | 2008-528500 A | 7/2008 | | |
| KR | 10-2014-0018577 A | 2/2014 | | |
| KR | 10-2016-0079983 A | 7/2016 | | |
| KR | 10-2017-0115737 A | 10/2017 | | |
| KR | 10-1795650 B1 | 11/2017 | | |
| KR | 10-1795653 B1 | 11/2017 | | |
| KR | 10-2018-0126406 A | 11/2018 | | |
| KR | 10-2020-0134175 A | 12/2020 | | |
| WO | 2004/074312 A2 | 9/2004 | | |
| WO | 2006/078899 A2 | 7/2006 | | |
| WO | 2008/111063 A2 | 9/2008 | | |
| WO | 2009/033737 A2 | 3/2009 | | |
| WO | 2011/060349 A1 | 5/2011 | | |
| WO | 2017/175963 A1 | 10/2017 | | |
| WO | 2018/127719 A2 | 7/2018 | | |
| WO | 2018/191348 A1 | 10/2018 | | |
| WO | 2018/225961 A1 | 12/2018 | | |
| WO | 2020/099925 A2 | 5/2020 | | |

OTHER PUBLICATIONS

Dinarello et al. Grand challenge in inflammation. Frontiers in immunology. 3:12, 2012 (Year: 2012).*
Chen et al. Inflammatory responses and inflammation-associated diseases in organs. Oncotarget, 2018, vol. 9, (No. 6), pp. 7204-7218 (Year: 2018).*
Pahwa et al. Chronic Inflammation. NCBI Bookshelf (Year: 2020).*
Herkel, J. et al., "Activation of the Akt-CREB signalling axis by a proline-rich heptapeptide confers resistance to stress-induced cell death and inflammation," Immunology, vol. 151; 474-480 (2017).
Lee, J. et al., "The antimicrobial peptide CMA3 derived from the CA-MA hybrid peptide: antibacterial and anti-inflammatory activities with low cytotoxicity and mechanism of action in *Escherichia coli*," American Society for Microbiology, AAC Accepted Manuscript; doi:10.1128/AAC.01998-15; 42 pages (2015).
English Translation of Decision of a Patent for Korean Patent Application No. 10-2022-0053844, mailed Apr. 13, 2023.
International Search Report and Written Opinion received for PCT Patent Application No. PCT/KR2020/006594, mailed on Aug. 24, 2020, 34 pages (18 pages of English Translation and 16 pages of Original Document).

* cited by examiner

*Primary Examiner* — Li N Komatsu
*Assistant Examiner* — Mercy H Sabila
(74) *Attorney, Agent, or Firm* — Hamilton, Brook, Smith & Reynolds, P.C.

(57) ABSTRACT

The present invention relates to a novel peptide compound or a pharmaceutically acceptable salt thereof.

5 Claims, 17 Drawing Sheets

Specification includes a Sequence Listing.

PEPTIDE COMPOUND OR PHARMACEUTICALLY ACCEPTABLE SALT THEREOF

RELATED APPLICATIONS

This application is the U.S. National Stage of International Application No. PCT/KR2020/006594, filed on May 20, 2020, which designates the U.S., published in Korean, and claims priority under 35 U.S.C. § 119 to Korean Patent Application No. 10-2019-0059628, filed on May 21, 2019. The entire teachings of the above applications are incorporated herein by reference.

CROSS-REFERENCE TO SEQUENCE LISTING

The Sequence Listing identified as "CNP0034_ST25.TXT" (35,475 bytes), created Dec. 20, 2023, is hereby incorporated by reference.

TECHNICAL FIELD

Various embodiments of the present invention relate to a novel peptide compound or a pharmaceutically acceptable salt thereof. Specifically, various embodiments of the present invention relate to a novel peptide compound or a pharmaceutically acceptable salt thereof having an anti-inflammatory activity.

BACKGROUND ART

Recently, the proportion of the elderly continues to increase due to the development of medical technology and the extension of life expectancy according to the economic development, and chronic inflammatory diseases such as atopy and asthma are increasing as the inflammatory response become chronic due to the immune system abnormality according to the increase in environmental pollution and stress.

In general, the inflammatory response is a defense mechanism of the living tissue against external stimuli such as bacterial infection or internal stimuli such as in vivo metabolites, and it occurs when nitric oxide (NO) and various cytokines such as TNF-α, IL-1β, and IL-6, which are various inflammatory regulators in cells, are produced. In addition, lipopolysaccharide (LPS), also known as endotoxin, is present in the cellular outer membrane of Gram negative bacteria and induces the activation of NF-κB (nuclear facter-κB), an intracellular transcription factor, in macrophages or mononuclear cells, thereby inducing gene expression of inflammatory cytokines, iNOS (inducible nitric oxide synthase), and COX-2 (cyclooxygenase-2) and producing inflammatory mediators.

Therefore, in order to regulate the inflammatory response, it is a key factor to regulate the expression of iNOS, COX-2, or NF-κB, and the secretion of cytokines and nitric oxide, and substances that regulate the activity of these factors are attracting attention as preventive and therapeutic agents for inflammatory diseases.

Substances currently used for anti-inflammatory purposes include non-steroids such as flufenamic acid, ibuprofen, benzydamine, indomethacin, and the like; and steroids such as prednisolone, dexamethasone, hydrocortisone, betamethasone and the like. However, These substances are highly toxic and cause several serious side effects such as liver damage, cancer, and stroke, which limit their use. In addition, there are cases in which a problem of inducing severe immunosuppression occurs because it cannot selectively act on substances that cause inflammation. Accordingly, the development of an inflammation therapeutic agent using a natural product that is safe for the body and has the advantage of being easy to consume for a long period of time compared to conventional medicines is being made. However, in the case of an anti-inflammatory substance extracted from a natural product, there are problems that the effective concentration at which the substance exhibits efficacy is weak, and a high production cost is required because it must be cultivated in agricultural land, etc.

In order to improve the above problems, a new concept anti-inflammatory agent is being developed as an alternative to the existing chemical inflammation therapeutic agent or an inflammation therapeutic agent using a natural product, and in particular, a lot of research is being done on the synthesis of peptides having an anti-inflammatory activity.

Accordingly, the present inventors have developed a peptide that can be economically mass-produced using only 9 amino acid residues while continuing research on substances exhibiting excellent anti-inflammatory activity, and found that the peptide does not exhibit cytotoxicity and has excellent anti-inflammatory activity. Based on the above, the present inventors completed the present invention.

DETAILED DESCRIPTION OF THE INVENTION

Technical Problem

In various embodiments of the present invention, there is provided a novel peptide compound or a pharmaceutically acceptable salt thereof.

Solution to Problem

A novel peptide compound or a pharmaceutically acceptable salt thereof according to one embodiment of the present invention is represented by formula 1 below.

$$A1-A2-A3-A4-A5 \quad \text{[Formula 1]}$$

in formula 1, A1 to A5 are linked by a peptide bond represented by formula 2 below, A1 is a substituted or unsubstituted proline or glutamine,
A2 is a substituted or unsubstituted glycine or aspartic acid,
A3 is a substituted or unsubstituted glutamine or glycine,
A4 is a substituted or unsubstituted aspartic acid or leucine,
A5 is a substituted or unsubstituted glycine or alanine, and zero to two of A1 to A5 may be independently substituted with any one selected from the group consisting of substituted or unsubstituted glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, and arginine.

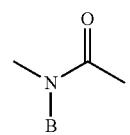

[Formula 2]

wherein, B is hydrogen, or is linked to at least any one of A1 to A5 to be cyclized.

Effects of the Invention

The present invention can provide novel peptide compounds having various structures or pharmaceutically acceptable salts thereof that can be used in various fields.

Since the novel peptide compound or pharmaceutically acceptable salt thereof of the present invention has only 5 to 8 amino acid residues, economical mass production is possible. In addition, it does not show cytotoxicity, has excellent stability, and exhibits excellent anti-inflammatory activity.

BEST MODE FOR CARRYING OUT THE INVENTION

Figure 1A:
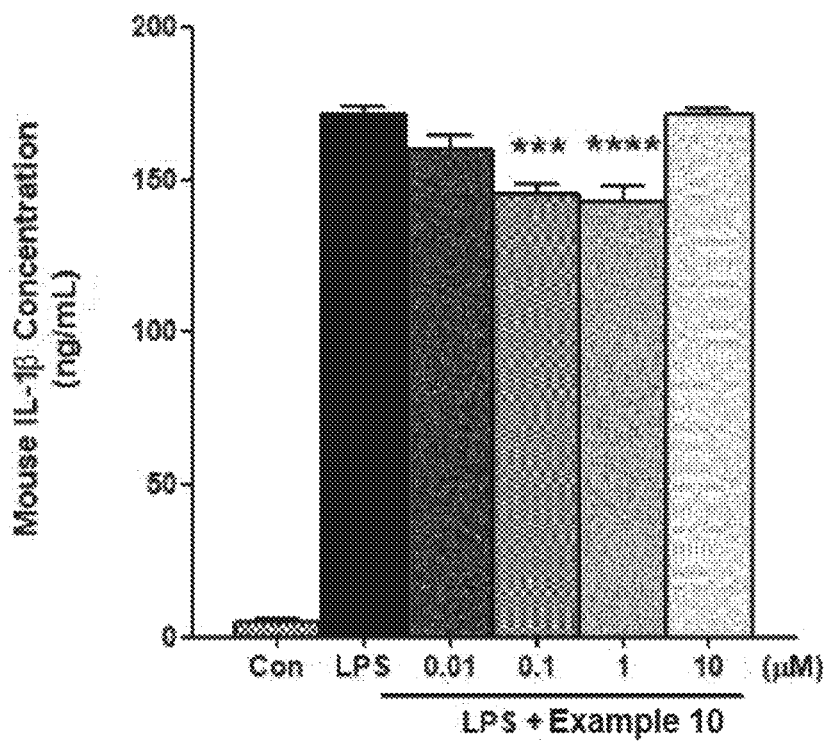
FIGS. 1a, 1b and 1c show results of measuring the expression levels of IL-1β, IL-6 and TNFα according to the treatment of Example 10 in LPS-stimulated macrophages, respectively.
Figure 1B:
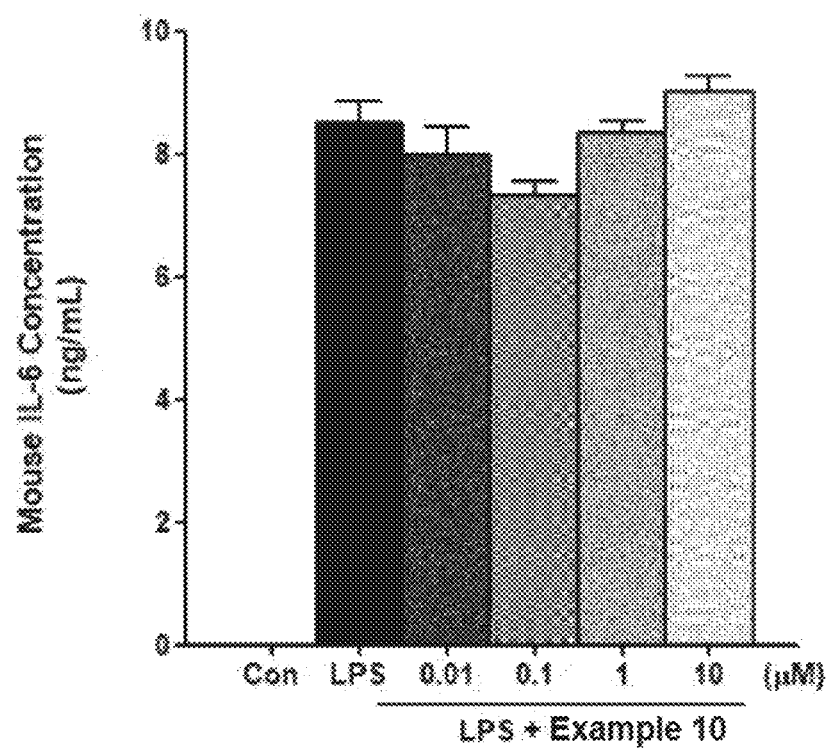

Hereinafter, various embodiments of the present specification are described with reference to the accompanying drawings. The embodiments and terms used herein are not intended to limit the technology described in this document to specific embodiments, and should be understood to include various modifications, equivalents, and/or substitutions of the embodiments.

A novel peptide compound or a pharmaceutically acceptable salt thereof according to one embodiment of the present invention is represented by formula 1 below.

$$A1\text{-}A2\text{-}A3\text{-}A4\text{-}A5 \quad \text{[Formula 1]}$$

in formula 1, A1 to A5 are linked by a peptide bond represented by formula 2 below, A1 is a substituted or unsubstituted proline or glutamine, A2 is a substituted or unsubstituted glycine or aspartic acid, A3 is a substituted or unsubstituted glutamine or glycine, A4 is a substituted or unsubstituted aspartic acid or leucine, A5 is a substituted or unsubstituted glycine or alanine, and zero to two of A1 to A5 may be independently substituted with any one selected from the group consisting of substituted or unsubstituted glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, and arginine.

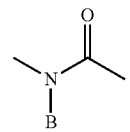

[Formula 2]

wherein, B is hydrogen, or is linked to at least any one of A1 to A5 to be cyclized.

A novel peptide compound or a pharmaceutically acceptable salt thereof according to one embodiment of the present invention is represented by formula 3 below.

$$A1\text{-}A2\text{-}A3\text{-}A4\text{-}A5\text{-}A6 \quad \text{[Formula 3]}$$

in formula 3, A1 to A6 are linked by a peptide bond represented by formula 2 below, A1 is a substituted or unsubstituted proline or glutamine, A2 is a substituted or unsubstituted glycine or aspartic acid, A3 is a substituted or unsubstituted glutamine or glycine, A4 is a substituted or unsubstituted aspartic acid or leucine, A5 is a substituted or unsubstituted glycine or alanine, A6 is a substituted or unsubstituted leucine or glycine, and zero to two of A1 to A6 may be independently substituted with any one selected from the group consisting of substituted or unsubstituted glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, and arginine.

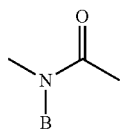

[Formula 2]

wherein, B is hydrogen, or is linked to at least any one of A1 to A6 to be cyclized.

A novel peptide compound or a pharmaceutically acceptable salt thereof according to one embodiment of the present invention is represented by formula 4 below.

A1-A2-A3-A4-A5-A6-A7        [Formula 4]

in formula 4, A1 to A7 are linked by a peptide bond represented by formula 2 below, A1 is a substituted or unsubstituted proline or glutamine,
A2 is a substituted or unsubstituted glycine or aspartic acid,
A3 is a substituted or unsubstituted glutamine or glycine,
A4 is a substituted or unsubstituted aspartic acid or leucine,
A5 is a substituted or unsubstituted glycine or alanine,
A6 is a substituted or unsubstituted leucine or glycine,
A7 is a substituted or unsubstituted alanine or proline, and zero to three of A1 to A7 may be independently substituted with any one selected from the group consisting of substituted or unsubstituted glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, and arginine.

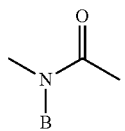

[Formula 2]

wherein, B is hydrogen, or is linked to at least any one of A1 to A7 to be cyclized.

A novel peptide compound or a pharmaceutically acceptable salt thereof according to one embodiment of the present invention is represented by formula 5 below.

A1-A2-A3-A4-A5-A6-A7-A8        [Formula 5]

in formula 5, A1 to A8 are linked by a peptide bond represented by formula 2 below,
A1 is a substituted or unsubstituted proline or glutamine,
A2 is a substituted or unsubstituted glycine or aspartic acid,
A3 is a substituted or unsubstituted glutamine or glycine,
A4 is a substituted or unsubstituted aspartic acid or leucine,
A5 is a substituted or unsubstituted glycine or alanine,
A6 is a substituted or unsubstituted leucine or glycine,
A7 is a substituted or unsubstituted alanine or proline, A8 is a substituted or unsubstituted glycine or lysine, and zero to three of A1 to A8 may be independently substituted with any one selected from the group consisting of substituted or unsubstituted glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, and arginine.

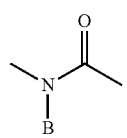

[Formula 2]

wherein, B is hydrogen, or is linked to at least any one of A1 to A8 to be cyclized.

A novel peptide compound or a pharmaceutically acceptable salt thereof according to one embodiment of the present invention is represented by formula 6 below.

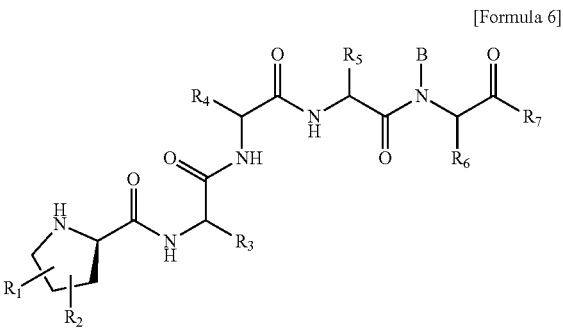

[Formula 6]

wherein, $R_1$ and $R_2$ are each independently hydrogen, a substituted or unsubstituted $C_{1-6}$alkyl, —X2, —Rb, —O—, =O, —CH$_2$Orb, or —ORb, wherein X2 is halogen, and Rb is hydrogen, a substituted or unsubstituted $C_{1-6}$alkyl, a substituted or unsubstituted $C_{5-12}$ aryl, a substituted or unsubstituted $C_{7-12}$ arylalkyl, or a substituted or unsubstituted heterocycle, $R_3$ to $R_7$ are hydrogen, a substituted or unsubstituted $C_{1-6}$alkyl, a substituted or unsubstituted $C_{1-10}$ alkoxy, a substituted or unsubstituted $C_{1-10}$ haloalkyl, a substituted or unsubstituted $C_{2-10}$ alkenyl, a substituted or unsubstituted $C_{2-10}$ alkynyl, a substituted or unsubstituted $C_{1-10}$ alkylene, a substituted or unsubstituted $C_{1-10}$ alkenylene, a substituted or unsubstituted $C_{1-10}$ alkynylene, a substituted or unsubstituted $C_{5-12}$ aryl, a substituted or unsubstituted $C_{7-12}$ arylalkyl, a substituted or unsubstituted $C_{5-14}$ arylalkynyl, a substituted or unsubstituted $C_{8-16}$ arylalkenyl, a substituted or unsubstituted $C_{3-10}$ heteroalkyl, a substituted or unsubstituted $C_{3-10}$ cycloalkyl, a substituted or unsubstituted $C_{3-10}$ heterocycloalkyl, or a substituted or unsubstituted $C_{5-12}$ heteroaryl, wherein the heteroalkyl, heterocycloalkyl or heteroaryl includes at least one of N, O or S, the substitution is one substituted with a non-hydrogen substituent, wherein the non-hydrogen substituent may be one or more selected from the group consisting of —RX, —Ra, —O—, =O, —ORa, —SRa, —S—, —N(Ra)2, —N+(Ra)3, =NRa, —C(RX)3, —CN, —OCN, —SCN, —N=C=O, —NSC, —NO, —NO2, =N—OH, =N2, —N3, —NHC(=O)Ra, —C(=O) Ra, —C(=O)NRaRa, —S(=O)2O—, —S(=O)2OH, —S(=O)2Ra, —OS(=O)2ORa, —S(=O)2NRa, —S(=O)Ra, —OP(=O)(ORa)2, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S) NRaRa and —C(=NRa)NRaNRa, wherein RX is F, Cl, Br or I, and Ra is H, $C_{1-6}$ alkyl, $C_{5-12}$ aryl, $C_{7-12}$ arylalkyl or heterocycle, and B is hydrogen, or is linked to at least any one of $R_5$ to $R_6$ to be cyclized.

A novel peptide compound or a pharmaceutically acceptable salt thereof according to one embodiment of the present invention is represented by formula 7 below.

[Formula 7]

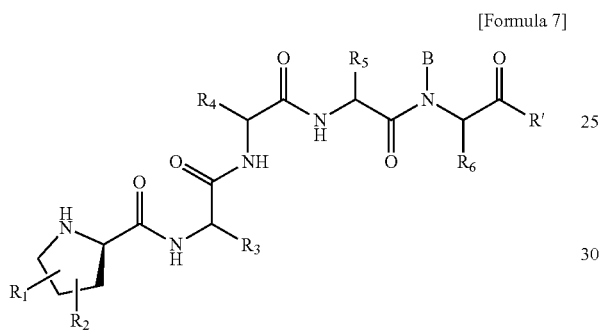

wherein, $R_1$ and $R_2$ are each independently hydrogen, a substituted or unsubstituted $C_{1-6}$alkyl, —X2, —Rb, —O—, =O, —CH2Orb, or —ORb, wherein X2 is halogen, and Rb is hydrogen, a substituted or unsubstituted $C_{1-6}$alkyl, a substituted or unsubstituted $C_{5-12}$ aryl, a substituted or unsubstituted $C_{7-12}$ arylalkyl, or a substituted or unsubstituted heterocycle, $R_3$ to $R_6$ are hydrogen, a substituted or unsubstituted $C_{1-6}$alkyl, a substituted or unsubstituted $C_{1-10}$ alkoxy, a substituted or unsubstituted $C_{1-10}$ haloalkyl, a substituted or unsubstituted $C_{2-10}$ alkenyl, a substituted or unsubstituted $C_{2-10}$ alkynyl, a substituted or unsubstituted $C_{1-10}$ alkylene, a substituted or unsubstituted $C_{1-10}$ alkenylene, a substituted or unsubstituted $C_{1-10}$ alkynylene, a substituted or unsubstituted $C_{5-12}$ aryl, a substituted or unsubstituted $C_{7-12}$ arylalkyl, a substituted or unsubstituted $C_{5-14}$ arylalkynyl, a substituted or unsubstituted $C_{8-16}$ arylalkenyl, a substituted or unsubstituted $C_{3-10}$ heteroalkyl, a substituted or unsubstituted $C_{3-10}$ cycloalkyl, a substituted or unsubstituted $C_{3-10}$ heterocycloalkyl, or a substituted or unsubstituted $C_{5-12}$ heteroaryl, wherein the heteroalkyl, heterocycloalkyl or heteroaryl includes at least one of N, O or S, the substitution is one substituted with a non-hydrogen substituent, wherein the non-hydrogen substituent may be one or more selected from the group consisting of —RX, —Ra, —O—, =O, —ORa, —SRa, —S—, —N(Ra)2, —N+ (Ra)3, =NRa, —C(RX)3, —CN, —OCN, —SCN, —N=C=O, —NSC, —NO, —NO2, =N—OH, =N2, —N3, —NHC(=O)Ra, —C(=O) Ra, —C(=O)NRaRa, —S(=O)2O—, —S(=O)2OH, —S(=O)2Ra, —OS(=O)20Ra, —S(=O)2NRa, —S(=O)Ra, —OP(=O)(ORa)2, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S) NRaRa and —C(=NRa)NRaNRa, wherein RX is F, Cl, Br or I, and Ra is H, $C_{1-6}$ alkyl, $C_{5-12}$ aryl, $C_{7-12}$ arylalkyl or heterocycle, B is hydrogen, or is linked to at least any one of $R_5$ to $R_6$ and R' to be cyclized, and R' is represented by any one of formulas 8 to 10 below.

[Formula 8]

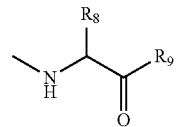

[Formula 9]

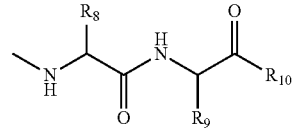

[Formula 10]

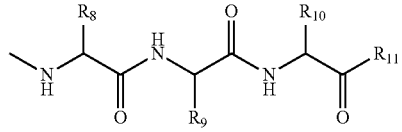

wherein, $R_8$ to $R_{11}$ are hydrogen, a substituted or unsubstituted $C_{1-6}$alkyl, a substituted or unsubstituted $C_{1-10}$ alkoxy, a substituted or unsubstituted $C_{1-10}$ haloalkyl, a substituted or unsubstituted $C_{2-10}$ alkenyl, a substituted or unsubstituted $C_{2-10}$ alkynyl, a substituted or unsubstituted $C_{1-10}$ alkylene, a substituted or unsubstituted $C_{1-10}$ alkenylene, a substituted or unsubstituted $C_{1-10}$ alkynylene, a substituted or unsubstituted $C_{5-12}$ aryl, a substituted or unsubstituted $C_{7-12}$ arylalkyl, a substituted or unsubstituted $C_{5-14}$ arylalkynyl, a substituted or unsubstituted $C_{8-16}$ arylalkenyl, a substituted or unsubstituted $C_{3-10}$ heteroalkyl, a substituted or unsubstituted $C_{3-10}$ cycloalkyl, a substituted or unsubstituted $C_{3-10}$ heterocycloalkyl, or a substituted or unsubstituted $C_{5-12}$ heteroaryl, wherein the heteroalkyl, heterocycloalkyl or heteroaryl includes at least one of N, O or S, and the substitution is one substituted with a non-hydrogen substituent, wherein the non-hydrogen substituent may be one or more selected from the group consisting of —RX, —Ra, —O—, =O, —ORa, —SRa, —S—, —N(Ra)2, —N+ (Ra)3, =NRa, —C(RX)3, —CN, —OCN, —SCN, —N=C=O, —NSC, —NO, —NO2, =N—OH, =N2, —N3, —NHC(=O)Ra, —C(=O) Ra, —C(=O)NRaRa, —S(=O)2O—, —S(=O)2OH, —S(=O)2Ra, —OS(=O)20Ra, —S(=O)2NRa, —S(=O)Ra, —OP(=O)(ORa)2, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S) NRaRa and —C(=NRa)NRaNRa, wherein RX is F, Cl, Br or I, and Ra is H, $C_{1-6}$ alkyl, $C_{5-12}$ aryl, $C_{7-12}$ arylalkyl or heterocycle.

A novel peptide compound or a pharmaceutically acceptable salt thereof according to one embodiment of the present invention is represented by formula 11 below.

[Formula 11]

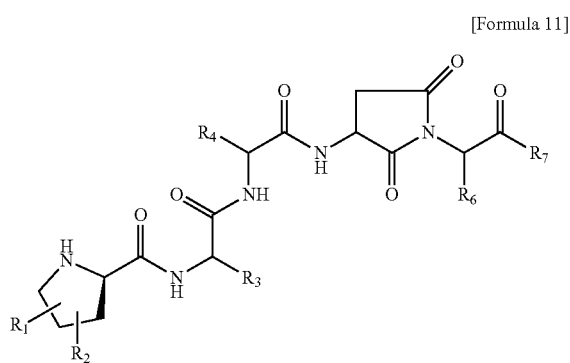

wherein, $R_1$ and $R_2$ are each independently hydrogen, a substituted or unsubstituted $C_{1-6}$alkyl, —X2, —Rb, —O—, =O, —CH$_2$Orb, or —ORb, wherein X2 is halogen, and Rb is hydrogen, a substituted or unsubstituted $C_{1-6}$alkyl, a substituted or unsubstituted $C_{5-12}$ aryl, a substituted or unsubstituted $C_{7-12}$ arylalkyl, or a substituted or unsubstituted heterocycle, $R_3$ $R_4$, $R_6$ and $R_7$ are hydrogen, a substituted or unsubstituted $C_{1-6}$alkyl, a substituted or unsubstituted $C_{1-10}$ alkoxy, a substituted or unsubstituted $C_{1-10}$ haloalkyl, a substituted or unsubstituted $C_{2-10}$ alkenyl, a substituted or unsubstituted $C_{2-10}$ alkynyl, a substituted or unsubstituted $C_{1-10}$ alkylene, a substituted or unsubstituted $C_{1-10}$ alkenylene, a substituted or unsubstituted $C_{1-10}$ alkynylene, a substituted or unsubstituted $C_{5-12}$ aryl, a substituted or unsubstituted $C_{7-12}$ arylalkyl, a substituted or unsubstituted $C_{5-14}$ arylalkynyl, a substituted or unsubstituted $C_{8-16}$ arylalkenyl, a substituted or unsubstituted $C_{3-10}$ heteroalkyl, a substituted or unsubstituted $C_{3-10}$ cycloalkyl, a substituted or unsubstituted $C_{3-10}$ heterocycloalkyl, or a substituted or unsubstituted $C_{5-12}$ heteroaryl, wherein the heteroalkyl, heterocycloalkyl or heteroaryl includes at least one of N, O or S, and the substitution is one substituted with a non-hydrogen substituent, wherein the non-hydrogen substituent may be one or more selected from the group consisting of —RX, —Ra, —O—, =O, —ORa, —SRa, —S—, —N(Ra)2, —N+ (Ra)3, =NRa, —C(RX)3, —CN, —OCN, —SCN, —N=C=O, —NSC, —NO, —NO2, =N—OH, =N2, —N3, —NHC(=O)Ra, —C(=O)Ra, —C(=O)NRaRa, —S(=O)2O—, —S(=O)2OH, —S(=O)2Ra, —OS(=O)2ORa, —S(=O)2NRa, —S(=O)Ra, —OP(=O)(ORa)2, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S) NRaRa and —C(=NRa)NRaNRa, wherein RX is F, Cl, Br or I, and Ra is H, $C_{1-6}$ alkyl, $C_{5-12}$ aryl, $C_{7-12}$ arylalkyl or heterocycle.

A novel peptide compound or a pharmaceutically acceptable salt thereof according to one embodiment of the present invention is represented by formula 12 below.

[Formula 12]

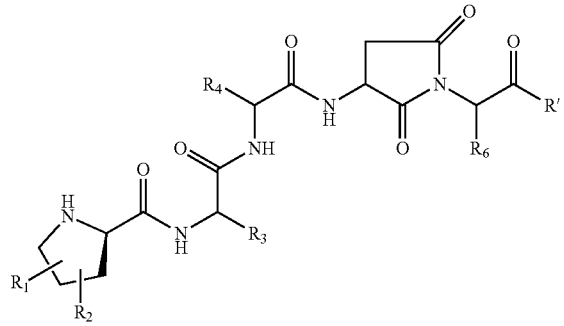

wherein, $R_1$ and $R_2$ are each independently hydrogen, a substituted or unsubstituted $C_{1-6}$alkyl, —X2, —Rb, —O—, =O, —CH$_2$Orb, or —ORb, wherein X2 is halogen, and Rb is hydrogen, a substituted or unsubstituted $C_{1-6}$alkyl, a substituted or unsubstituted $C_{5-12}$ aryl, a substituted or unsubstituted $C_{7-12}$ arylalkyl, or a substituted or unsubstituted heterocycle, $R_3$, $R_4$ and $R_6$ are hydrogen, a substituted or unsubstituted $C_{1-6}$alkyl, a substituted or unsubstituted $C_{1-10}$ alkoxy, a substituted or unsubstituted $C_{1-10}$ haloalkyl, a substituted or unsubstituted $C_{2-10}$ alkenyl, a substituted or unsubstituted $C_{2-10}$ alkynyl, a substituted or unsubstituted $C_{1-10}$ alkylene, a substituted or unsubstituted $C_{1-10}$ alkenylene, a substituted or unsubstituted $C_{1-10}$ alkynylene, a substituted or unsubstituted $C_{5-12}$ aryl, a substituted or unsubstituted $C_{7-12}$ arylalkyl, a substituted or unsubstituted $C_{5-14}$ arylalkynyl, a substituted or unsubstituted $C_{8-16}$ arylalkenyl, a substituted or unsubstituted $C_{3-10}$ heteroalkyl, a substituted or unsubstituted $C_{3-10}$ cycloalkyl, a substituted or unsubstituted $C_{3-10}$ heterocycloalkyl, or a substituted or unsubstituted $C_{5-12}$ heteroaryl, wherein the heteroalkyl, heterocycloalkyl or heteroaryl includes at least one of N, O or S, the substitution is one substituted with a non-hydrogen substituent, wherein the non-hydrogen substituent may be one or more selected from the group consisting of —RX, —Ra, —O—, =O, —ORa, —SRa, —S—, —N(Ra)2, —N+ (Ra)3, =NRa, —C(RX)3, —CN, —OCN, —SCN, —N=C=O, —NSC, —NO, —NO2, =N—OH, =N2, —N3, —NHC(=O)Ra, —C(=O)Ra, —C(=O)NRaRa, —S(=O)2O—, —S(=O)2OH, —S(=O)2Ra, —OS(=O)2ORa, —S(=O)2NRa, —S(=O)Ra, —OP(=O)(ORa)2, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S) NRaRa and —C(=NRa)NRaNRa, wherein RX is F, Cl, Br or I, and Ra is H, $C_{1-6}$ alkyl, $C_{5-12}$ aryl, $C_{7-12}$ arylalkyl or heterocycle, and R' is represented by any one of formulas 13 to 15 below.

[Formula 13]

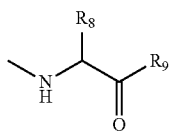

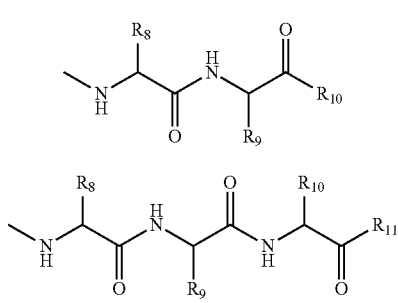

[Formula 14]

[Formula 15]

wherein, $R_8$ to $R_{11}$ are hydrogen, a substituted or unsubstituted $C_{1-6}$alkyl, a substituted or unsubstituted $C_{1-10}$ alkoxy, a substituted or unsubstituted $C_{1-10}$ haloalkyl, a substituted or unsubstituted $C_{2-10}$ alkenyl, a substituted or unsubstituted $C_{2-10}$ alkynyl, a substituted or unsubstituted $C_{1-10}$ alkylene, a substituted or unsubstituted $C_{1-10}$ alkenylene, a substituted or unsubstituted $C_{1-10}$ alkynylene, a substituted or unsubstituted $C_{5-12}$ aryl, a substituted or unsubstituted $C_{7-12}$ arylalkyl, a substituted or unsubstituted $C_{5-14}$ arylalkynyl, a substituted or unsubstituted $C_{8-16}$ arylalkenyl, a substituted or unsubstituted $C_{3-10}$ heteroalkyl, a substituted or unsubstituted $C_{3-10}$ cycloalkyl, a substituted or unsubstituted $C_{3-10}$ heterocycloalkyl, or a substituted or unsubstituted $C_{5-12}$ heteroaryl, wherein the heteroalkyl, heterocycloalkyl or heteroaryl includes at least one of N, O or S, and the substitution is one substituted with a non-hydrogen substituent, wherein the non-hydrogen substituent may be one or more selected from the group consisting of —RX, —Ra, —O—, =O, —ORa, —SRa, —S—, —N(Ra)2, —N+ (Ra)3, =NRa, —C(RX)3, —CN, —OCN, —SCN, —N=C=O, —NSC, —NO, —NO2, =N—OH, =N2, —N3, —NHC(—O)Ra, —C(=O)Ra, —C(=O)NRaRa, —S(=O)2O—, —S(=O)2OH, —S(=O)2Ra, —OS(=O)2ORa, —S(=O)2NRa, —S(=O)Ra, —OP(=O)(ORa)2, —C(=O)Ra, alkylene-C(—O)Ra, —C(=S)Ra, —C(—O)ORa, alkylene-C(=O)ORa, —C(=O)O—, alkylene-C(=O)O—, —C(=S)ORa, —C(—O)SRa, —C(=S) SRa, —C(=O)NRaRa, alkylene-C(=O)NRaRa, —C(=S) NRaRa and —C(—NRa)NRaNRa, wherein RX is F, Cl, Br or I, and Ra is H, $C_{1-6}$ alkyl, $C_{5-12}$ aryl, $C_{7-12}$ arylalkyl or heterocycle.

A novel peptide compound or a pharmaceutically acceptable salt thereof according to one embodiment of the present invention has a configuration of 5 mer to 8 mer continuously or discontinuously in the amino acid sequence of Hyp-Gly-Gln-Asp-Gly-Leu-Ala-Gly-Pro-Lys, wherein the 5 mer to 8 mer are linear, or at least a part of which is cyclized.

On the other hand, the peptide, at least a part of which is cyclized, may be a peptide containing Asu. Here, Asu is aspartimide or aminosuccinimide.

A novel peptide compound or a pharmaceutically acceptable salt thereof according to one embodiment of the present invention has a configuration of 5 mer to 8 mer continuously or discontinuously in the amino acid sequence of Hyp-Gly-Gln-Asp-Gly-Leu-Ala-Gly-Pro-Lys, wherein the 5 mer to 8 mer are linear, or at least a part of which is cyclized, it has a configuration in which at least any one of amino acids is substituted with any one selected from the group consisting of substituted or unsubstituted glycine, alanine, serine, threonine, cysteine, valine, leucine, isoleucine, methionine, proline, phenylalanine, tyrosine, tryptophan, aspartic acid, glutamic acid, asparagine, glutamine, histidine, lysine, and arginine in the configuration of 5 mer to 8 mer.

On the other hand, the peptide, at least a part of which is cyclized, may be a peptide containing Asu. Here, Asu is aspartimide or aminosuccinimide.

A novel peptide compound or a pharmaceutically acceptable salt thereof according to one embodiment of the present invention is represented by formula 16 below.

[Formula 16]

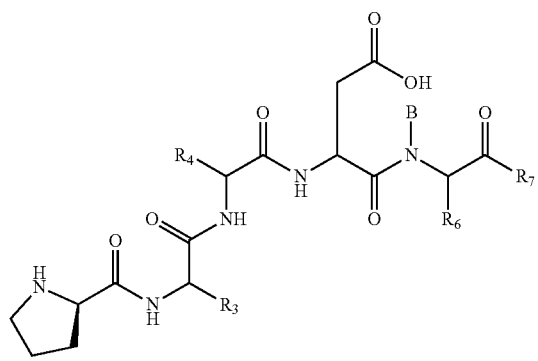

wherein, $R_3$, $R_4$, $R_6$ and $R_7$ are hydrogen, a substituted or unsubstituted $C_{1-6}$alkyl, a substituted or unsubstituted $C_{1-10}$ alkoxy, a substituted or unsubstituted $C_{1-10}$ haloalkyl, a substituted or unsubstituted $C_{2-10}$ alkenyl, a substituted or unsubstituted $C_{2-10}$ alkynyl, a substituted or unsubstituted $C_{1-10}$ alkylene, a substituted or unsubstituted $C_{1-10}$ alkenylene, a substituted or unsubstituted $C_{1-10}$ alkynylene, a substituted or unsubstituted $C_{5-12}$ aryl, a substituted or unsubstituted $C_{7-12}$ arylalkyl, a substituted or unsubstituted $C_{5-14}$ arylalkynyl, a substituted or unsubstituted $C_{8-16}$ arylalkenyl, a substituted or unsubstituted $C_{3-10}$ heteroalkyl, a substituted or unsubstituted $C_{3-10}$ cycloalkyl, a substituted or unsubstituted $C_{3-10}$ heterocycloalkyl, or a substituted or unsubstituted $C_{5-12}$ heteroaryl, wherein the heteroalkyl, heterocycloalkyl or heteroaryl includes at least one of N, O or S, the substitution is one substituted with a non-hydrogen substituent, wherein the non-hydrogen substituent may be one or more selected from the group consisting of —RX, —Ra, —O—, =O, —ORa, —SRa, —S—, —N(Ra)2, —N+ (Ra)3, =NRa, —C(RX)3, —CN, —OCN, —SCN, —N=C=O, —NSC, —NO, —NO2, =N—OH, =N2, —N3, —NHC(—O)Ra, —C(=O)Ra, —C(=O)NRaRa, —S(=O)2O—, —S(=O)2OH, —S(=O)2Ra, —OS(=O)2ORa, —S(=O)2NRa, —S(=O)Ra, —OP(=O)(ORa)2, —C(=O)Ra, alkylene-C(=O)Ra, —C(=S)Ra, —C(—O)ORa, alkylene-C(=O)ORa, —C(—O)O—, alkylene-C(=O)O—, —C(=S)ORa, —C(—O)SRa, —C(=S) SRa, —C(=O)NRaRa, alkylene-C(—O)NRaRa, —C(=S) NRaRa and —C(—NRa)NRaNRa, wherein RX is F, Cl, Br or I, and Ra is H, $C_{1-6}$ alkyl, $C_{5-12}$ aryl, $C_{7-12}$ arylalkyl or heterocycle, and B is hydrogen, or is linked to at least any one of aspartic acid and $R_6$ to be cyclized.

A novel peptide compound or a pharmaceutically acceptable salt thereof according to one embodiment of the present invention is represented by formula 17 below.

[Formula 17]

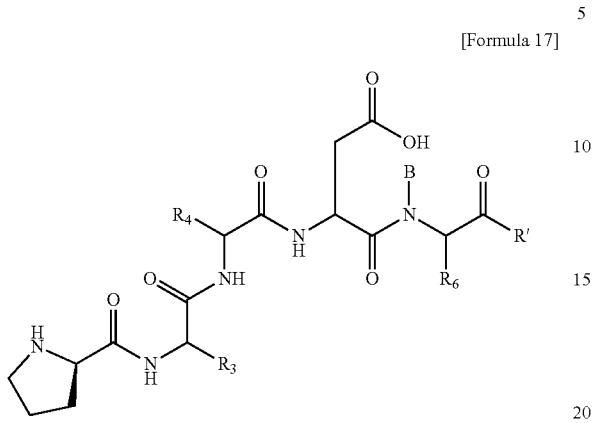

wherein, $R_3$, $R_4$, and $R_6$ are hydrogen, a substituted or unsubstituted $C_{1-6}$alkyl, a substituted or unsubstituted $C_{1-10}$ alkoxy, a substituted or unsubstituted $C_{1-10}$ haloalkyl, a substituted or unsubstituted $C_{2-10}$ alkenyl, a substituted or unsubstituted $C_{2-10}$ alkynyl, a substituted or unsubstituted $C_{1-10}$ alkylene, a substituted or unsubstituted $C_{1-10}$ alkenylene, a substituted or unsubstituted $C_{1-10}$ alkynylene, a substituted or unsubstituted $C_{5-12}$ aryl, a substituted or unsubstituted $C_{7-12}$ arylalkyl, a substituted or unsubstituted $C_{5-14}$ arylalkynyl, a substituted or unsubstituted $C_{8-16}$ arylalkenyl, a substituted or unsubstituted $C_{3-10}$ heteroalkyl, a substituted or unsubstituted $C_{3-10}$ cycloalkyl, a substituted or unsubstituted $C_{3-10}$ heterocycloalkyl, or a substituted or unsubstituted $C_{5-12}$ heteroaryl, wherein the heteroalkyl, heterocycloalkyl or heteroaryl includes at least one of N, O or S, the substitution is one substituted with a non-hydrogen substituent, wherein the non-hydrogen substituent may be one or more selected from the group consisting of —RX, —Ra, —O—, =O, —ORa, —SRa, —S—, —N(Ra)2, —N+ (Ra)3, =NRa, —C(RX)3, —CN, —OCN, —SCN, —N=C=O, —NSC, —NO, —NO2, =N—OH, =N2, —N3, —NHC(=O)Ra, —C(=O)Ra, —C(=O)NRaRa, —S(=O)2O—, —S(=O)2OH, —S(=O)2Ra, —OS(=O)2ORa, —S(=O)2NRa, —S(=O)Ra, —OP(=O)(ORa)2, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S)SRa, —C(=O)NRaRa, alkylene-C(=O)NRaRa, —C(=S) NRaRa and —C(—NRa)NRaNRa, wherein RX is F, Cl, Br or I, and Ra is H, $C_{1-6}$ alkyl, $C_{5-12}$ aryl, $C_{7-12}$ arylalkyl or heterocycle, B is hydrogen, or is linked to at least any one of aspartic acid and $R_6$ to be cyclized, and R' is represented by any one of formulas 8 to 10 below.

[Formula 8]

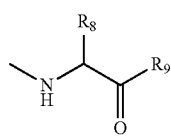

[Formula 9]

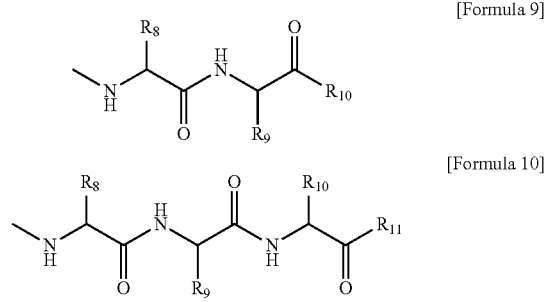

[Formula 10]

wherein, $R_8$ to $R_{11}$ are hydrogen, a substituted or unsubstituted $C_{1-6}$alkyl, a substituted or unsubstituted $C_{1-10}$ alkoxy, a substituted or unsubstituted $C_{1-10}$ haloalkyl, a substituted or unsubstituted $C_{2-10}$ alkenyl, a substituted or unsubstituted $C_{2-10}$ alkynyl, a substituted or unsubstituted $C_{1-10}$ alkylene, a substituted or unsubstituted $C_{1-10}$ alkenylene, a substituted or unsubstituted $C_{1-10}$ alkynylene, a substituted or unsubstituted $C_{5-12}$ aryl, a substituted or unsubstituted $C_{7-12}$ arylalkyl, a substituted or unsubstituted $C_{5-14}$ arylalkynyl, a substituted or unsubstituted $C_{8-16}$ arylalkenyl, a substituted or unsubstituted $C_{3-10}$ heteroalkyl, a substituted or unsubstituted $C_{3-10}$ cycloalkyl, a substituted or unsubstituted $C_{3-10}$ heterocycloalkyl, or a substituted or unsubstituted $C_{5-12}$ heteroaryl, wherein the heteroalkyl, heterocycloalkyl or heteroaryl includes at least one of N, O or S, and the substitution is one substituted with a non-hydrogen substituent, wherein the non-hydrogen substituent may be one or more selected from the group consisting of —RX, —Ra, —O—, =O, —ORa, —SRa, —S—, —N(Ra)2, —N+ (Ra)3, =NRa, —C(RX)3, —CN, —OCN, —SCN, —N=C—O, —NSC, —NO, —NO2, =N—OH, =N2, —N3, —NHC(=O)Ra, —C(=O)Ra, —C(=O)NRaRa, —S(=O)2O—, —S(=O)2OH, —S(=O)2Ra, —OS(—O)2ORa, —S(=O)2NRa, —S(=O)Ra, —OP(=O)(ORa)2, —C(=O)Ra, alkylene-C(=O)Ra, —C(=S)Ra, —C(=O)ORa, alkylene-C(=O)ORa, —C(=O)O—, alkylene-C(=O)O—, —C(=S)ORa, —C(=O)SRa, —C(=S) SRa, —C(=O)NRaRa, alkylene-C(—O)NRaRa, —C(=S) NRaRa and —C(—NRa)NRaNRa, wherein RX is F, Cl, Br or I, and Ra is H, $C_{1-6}$ alkyl, $C_{5-12}$ aryl, $C_{7-12}$ arylalkyl or heterocycle.

A novel peptide compound or a pharmaceutically acceptable salt thereof according to one embodiment of the present invention is represented by formula 17 below.

[Formula 17]

$$X_1—X_2—X_3—X_4—X_5$$

in formula 17, $X_1$ is any one selected from the group consisting of Hyp, D Hyp, cis-4F-Pro, trans-4NH$_2$-Pro, 4,4-difluoro-Pro, 4-methylene-Pro, 4,4-dimethyl Pro, and Pro, $X_2$ is any one selected from the group consisting of Gly, Ala, Val, and Leu, $X_3$ is Gln or D Gln, $X_4$ is any one selected from the group consisting of Asp, Ala, isopropyl ester-substituted Asp, D Asp, Glu, Leu, and Asu, and $X_5$ is any one selected from the group consisting of Val, Leu, Ala, Gly, Aib, and isopropyl ester-substituted Gly.

A novel peptide compound or a pharmaceutically acceptable salt thereof according to one embodiment of the present invention is represented by formula 18 below.

$$X_1\text{—}X_2\text{—}X_3\text{—}X_4\text{—}X_5\text{—}X_6 \quad \text{[Formula 18]}$$

in formula 18,
$X_1$ is any one selected from the group consisting of Hyp, D Hyp, cis-4F-Pro, trans-4NH$_2$-Pro, 4,4-difluro-Pro, 4-methylene-Pro, 4,4-dimethyl Pro, and Pro,
$X_2$ is any one selected from the group consisting of Gly, Ala, Val, and Leu,
$X_3$ is Gln or D Gln,
$X_4$ is any one selected from the group consisting of Asp, Ala, isopropyl ester-substituted Asp, D Asp, Glu, Leu, Asu, Asn, His, and Aib,
$X_5$ is any one selected from the group consisting of Val, Leu, Ala, Gly, Aib, and isopropyl ester-substituted Gly, and
$X_6$ is any one selected from the group consisting of Leu, D Leu, isopropyl ester-substituted Leu, and Val.

A novel peptide compound or a pharmaceutically acceptable salt thereof according to one embodiment of the present invention is represented by formula 19 below.

$$X_1\text{—}X_2\text{—}X_3\text{—}X_4\text{—}X_5\text{—}X_6\text{—}X_7 \quad \text{[Formula 19]}$$

in formula 19,
$X_1$ is any one selected from the group consisting of Hyp, D Hyp, cis-4F-Pro, trans-4NH$_2$-Pro, 4,4-difluoro-Pro, 4-methylene-Pro, 4,4-dimethyl Pro, and Pro,
$X_2$ is any one selected from the group consisting of Gly, Ala, Val, and Leu,
$X_3$ is Gln or D Gln,
$X_4$ is any one selected from the group consisting of Asp, Ala, isopropyl ester-substituted Asp, D Asp, Glu, Leu, Asu, Asn, His, and Aib,
$X_5$ is any one selected from the group consisting of Val, Leu, Ala, Gly, Aib, isopropyl ester-substituted Gly, tert Leu, phenyl Gly,
$X_6$ is any one selected from the group consisting of Leu, D Leu, isopropyl ester-substituted Leu, and Val, and
$X_7$ is any one selected from the group consisting of Ala, D Ala, and isopropyl ester-substituted Ala.

A novel peptide compound or a pharmaceutically acceptable salt thereof according to one embodiment of the present invention is represented by formula 20 below.

$$X_1\text{—}X_2\text{—}X_3\text{—}X_4\text{—}X_5\text{—}X_6\text{—}X_7\text{—}X_8 \quad \text{[Formula 20]}$$

in formula 20,
$X_1$ is any one selected from the group consisting of Hyp, D Hyp, cis-4F-Pro, trans-4NH$_2$-Pro, 4,4-difluoro-Pro, 4-methylene-Pro, 4,4-dimethyl Pro, and Pro,
$X_2$ is any one selected from the group consisting of Gly, Ala, Val, and Leu,
$X_3$ is Gln or D Gln,
$X_4$ is any one selected from the group consisting of Asp, Ala, isopropyl ester-substituted Asp, D Asp, Glu, Leu, and Asu,
$X_5$ is any one selected from the group consisting of Val, Leu, Ala, Gly, Aib, and isopropyl ester-substituted Gly,
$X_6$ is any one selected from the group consisting of Leu, D Leu, isopropyl ester-substituted Leu, and Val,
$X_7$ is any one selected from the group consisting of Ala, D Ala, and isopropyl ester-substituted Ala, and
$X_8$ is Gly.

A novel peptide compound or a pharmaceutically acceptable salt thereof according to one embodiment of the present invention is represented by formula 21 below.

$$X_1\text{—}X_2\text{—}X_3\text{—}X_4\text{—}X_5\text{—}X_6 \quad \text{[Formula 21]}$$

in formula 21,
$X_1$ is Gln or Gly
$X_2$ is any one selected from the group consisting of Leu, Gln, Asp, Glu, and Asu,
$X_3$ is any one selected from the group consisting of Gly, Asp, and Ala,
$X_4$ is Leu or Gly,
$X_5$ is any one selected from the group consisting of Ala, Leu, and Pro, and
$X_6$ is any one selected from the group consisting of Gly, Ala, and Lys.

A novel peptide compound or a pharmaceutically acceptable salt thereof according to one embodiment of the present invention is represented by formula 22 below.

$$X_1\text{-Gly-}X_3\text{—}X_4\text{-Gly-Pro-Lys} \quad \text{[Formula 22]}$$

in formula 22,
$X_1$ is any one selected from the group consisting of Asp, Leu, Hyp and Asu,
$X_3$ is Leu or Gln, and
$X_4$ is Ala or Asp.

A novel peptide compound or a pharmaceutically acceptable salt thereof according to one embodiment of the present invention is represented by formula 23 below.

$$\text{Gln-}X_2\text{-Gly-Ley-Ala-Gly-Pro-Lys} \quad \text{[Formula 23]}$$

in formula 23,
$X_2$ is at least any one of Asp, Leu, and Asu.

In formulas 17 to 23 above, Hyp is (2S,4R) trans-4-hydroxy-L-proline, Gly is glycine, Gln is glutamine, Asp is aspartic acid, Leu is leucine, Ala is alanine, Pro is proline, Val is valine, Tert-Leu is L-α-tert-butylglycine, Asu is aspartimide or aminosuccinimide, Lys is lysine, isopropyl ester is a derivative substituted with isopropyl ester at the amino acid terminal group, Aib is 2-aminoisobutyric acid, cis-4F-Pro is cis-4-fluoro-L-proline, trans-4NH$_2$-Pro is trans-4-amino-L-proline, 4,4-difluoro-Pro is 4-difluoro-L-proline, 4-methylene-Pro is 4-methylene-L-proline, 4,4-dimethyl Pro is 4,4-dimethyl-L-proline, D Hyp is trans-4-hydroxy-D-proline, D Gln is D-glutamine, D Asp is D-aspartic acid, D Leu is D-leucine, Asn is asparagine, and His is histidine.

Since the novel peptide compound or pharmaceutically acceptable salt thereof of the present invention has only 5 to 8 amino acid residues, economical mass production is possible.

The above-described novel peptide compound or pharmaceutically acceptable salt thereof does not show cytotoxicity, has excellent stability, and has an anti-inflammatory activity. As used herein, the term "anti-inflammatory" means preventing, treating or ameliorating inflammation. Here, the inflammation refers to a disease caused by infection due to external infectious agents (bacteria, fungi, viruses, various types of allergens, and the like), wounds, surgery, burns, frostbite, electrical stimulation, or chemicals, etc., and the disease includes dermatitis, inflammatory bowel disease, gastric ulcer, colitis, cystitis, rhinitis, tonsillitis or asthma, etc., but is not particularly limited thereto.

The present invention relates to a pharmaceutical composition for preventing or treating inflammation, comprising the above-described novel peptide compound or pharmaceutically acceptable salt thereof as an active ingredient.

In the pharmaceutical composition for preventing or treating inflammation of the present invention, the novel peptide compound or pharmaceutically acceptable salt thereof may be included at a concentration of 0.001 to 10 μM. A composition comprising an anti-inflammatory active peptide at a concentration of less than 0.001 μM may have a weak anti-inflammatory effect, and if it has a concentration of more than 10 μM, the increase in the effect according to the increase in concentration is not proportional, so it may be inefficient, and there is a problem in that the stability of the formulation is not secured.

The pharmaceutical composition for preventing or treating inflammation of the present invention may be several oral or parenteral formulations. When it is formulated, it can be prepared using a diluent or an excipient such as a filler, a bulking agent, a binder, a wetting agent, a disintegrating agent, a surfactant, etc. commonly used. Solid preparations for oral administration include tablets, pills, powders, granules, capsules, and the like, and such a solid preparation may be prepared by mixing one or more compounds with at least one excipient, for example, starch, calcium carbonate, sucrose or lactose, gelatin, and the like. In addition to the excipients, lubricants such as magnesium stearate, talc and the like may also be used.

Liquid preparations for oral administration include suspensions, internal solutions, emulsions, syrups, and the like. In addition to water and liquid paraffin, which are commonly used simple diluents, various excipients such as a wetting agent, a sweeting agent, a perfuming agent, a preserving agent and the like may be included.

Preparations for parenteral administration may include sterile aqueous solutions, non-aqueous solvents, suspensions, emulsions, lyophilized preparations, and suppositories. As a non-aqueous solvent and a suspending solvent, propylene glycol, polyethylene glycol, vegetable oils such as olive oil, injectable esters such as ethyl oleate, and the like may be used. As a base of the suppository, witepsol, macrogol, tween 61, cacao butter, laurin butter, glycerogelatin, and the like may be used.

The dosage form of the composition of the present invention may be used in the form of a salt, and may be also used alone or in combination with other active compounds as well as in an appropriate group. As the salt, for example, hydrochloric acid, sulfuric acid, nitric acid, phosphoric acid, hydrofluoric acid, hydrobromic acid, formic acid, acetic acid, tartaric acid, lactic acid, citric acid, fumaric acid, maleic acid, succinic acid, methanesulfonic acid, benzenesulfonic acid, toluenesulfonic acid, naphthalenesulfonic acid, and the like may be used.

The composition of the present invention may be administered parenterally or orally as desired, and may be administered once to several times in divided doses to be administered in an amount of 0.1 to 500 mg, 1 to 100 mg per 1 kg of body weight per day. The dosage for a specific patient may vary depending on the patient's body weight, age, sex, health condition, diet, administration time, mode of administration, excretion rate, severity of disease, and the like.

The composition according to the present invention may be formulated and used in any form including oral formulations such as a powder, a granule, a tablet, a capsule, a suspension, an emulsion, a syrup and an aerosol, external preparations such as an ointment and a cream, a suppository, and a sterile injection solution, and the like, respectively, according to conventional methods.

The composition according to the present invention may be administered to mammals such as rats, mice, livestock, and humans by various routes such as parenteral and oral administration, and all modes of administration may be expected, and it may be administered, for example, by oral, rectal or intravenous, intramuscular, subcutaneous, intrauterine dural or intracerebroventricular injection.

On the other hand, the composition according to the present invention does not have serious toxicity and side effects, so it can be safely used even when used for a long period of time for preventive purposes.

The present invention relates to a food composition for preventing or ameliorating inflammation, comprising the above-described novel peptide compound or pharmaceutically acceptable salt thereof as an active ingredient.

In the food composition for preventing or ameliorating inflammation of the present invention, the novel peptide compound or pharmaceutically acceptable salt thereof may be included at a concentration of 0.001 to 10 μM. A composition comprising an anti-inflammatory active peptide at a concentration of less than 0.001 μM may have a weak anti-inflammatory effect, and if it has a concentration of more than 10 μM, the increase in the effect according to the increase in concentration is not proportional, so it may be inefficient, and there is a problem in that the stability of the formulation is not secured.

The food composition for preventing or ameliorating inflammation is preferably a powder, a granule, a tablet, a capsule or a beverage, but is not limited thereto.

The food of the present invention may be used by adding the novel peptide compound or pharmaceutically acceptable salt thereof of the present invention as it is, or in combination with other food or food ingredients, and may be appropriately used according to a conventional method.

The type of the food is not particularly limited. Examples of the food to which the novel peptide compound or pharmaceutically acceptable salt thereof of the present invention can be added include meat, sausage, bread, chocolate, candy, snacks, confectionery, pizza, ramen, other noodles, gum, dairy products including ice cream, various soups, beverages, teas, drinks, alcoholic beverages, vitamin complexes, and the like, and include all foods in the ordinary sense.

The beverage composition of the present invention may contain various flavoring agents, natural carbohydrates or the like as additional ingredients, like conventional beverages. The above-described natural carbohydrates are monosaccharides such as glucose and fructose, disaccharides such as maltose and sucrose, and polysaccharides such as dextrin and cyclodextrin, and sugar alcohols such as xylitol, sorbitol and erythritol. As a sweeting agent, natural sweeting agents such as taumatine and stevia extract, synthetic sweeting agents such as saccharin and aspartame, and the like may be used.

In addition to the above, the food of the present invention may contain various nutrients, vitamins, electrolytes, flavoring agents, coloring agents, pectic acid and its salts, alginic acid and its salts, organic acids, protective colloidal thickeners, pH adjusters, stabilizing agents, preserving agents, glycerin, alcohol, a carbonation agent used in carbonated beverages, and the like. In addition, it may contain the pulp for the production of natural fruit juice, fruit juice beverage and vegetable beverage. These ingredients may be used independently or in combination. The proportion of these additives is not critical, but is generally selected in the range of 0.01 to 0.1 parts by weight per 100 parts by weight of the composition of the present invention.

The food composition for preventing or ameliorating inflammation according to the present invention may be used as a feed additive or feed.

When used as a feed additive, the composition may be a solution having a high concentration of 20 to 90% or may be prepared in a powder or granular form. The feed additives may further include any one of or one or more of organic acids such as citric acid, humic acid, adipic acid, lactic acid, and malic acid, phosphates such as sodium phosphate, potassium phosphate, acidic pyrophosphate, and polyphosphate, natural antioxidants such as polyphenol, catechin, alpha-tocopherol, rosemary extract, vitamin C, green tea extract, licorice extract, chitosan, tannic acid, and phytic acid. When used as a feed, the composition may be formulated in a conventional feed form, and may include conventional feed ingredients together.

Feed additives and feeds may further include grains such as milled or crushed wheat, oats, barley, corn and rice; vegetable protein feeds such as feeds based on rape, soybean, and sunflower as a main ingredient; animal protein feeds such as blood meal, meat meal, bone meal and fish meal; dry ingredients consisting of sugar and dairy products, for example, various powdered milk and whey powder, and the like, and may further include nutritional supplements, digestion and absorption enhancers, growth promoters, and the like.

The feed additive may be administered to the animal alone or in combination with other feed additives in an edible carrier. In addition, the feed additive can be easily administered to the animal as a top dressing, directly mixing them with animal feed, or in an oral formulation separate from the feed. When the feed additive is administered separately from animal feed, it may be combined with a pharmaceutically acceptable edible carrier as well known in the art to prepare an immediate release or sustained release formulation. Such edible carriers may be solid or liquid, for example corn starch, lactose, sucrose, soybean flakes, peanut oil, olive oil, sesame oil and propylene glycol. When a solid carrier is used, the feed additive may be a tablet, a capsule, a powder, a troche or a sugar-containing tablet, or a top dressing in a microdispersed form. When a liquid carrier is used, the feed additive may be in the form of a gelatin soft capsule, or a syrup or a suspension, an emulsion, or a solution.

In addition, the feed additive and feed may contain auxiliary agents, for example, preservatives, stabilizers, wetting or emulsifying agents, solubility promoters, and the like. The feed additive may be used by adding to animal feed by immersion, spraying, or mixing.

The feed or feed additive of the present invention may be applied to a diet of a number of animals including mammals, poultry and fish.

It may be used for the mammal including pigs, cattle, sheep, goats, laboratory rodents, and laboratory rodents, as well as pets (for example, dogs, cats), and the like, may be used for the poultry including chickens, turkeys, ducks, geese, pheasants, and quail, and the like, and may be used for the fish such as trout, but is not limited thereto.

In one embodiment, the feed or feed additive may be used for preventing or treating inflammation in pets. The pets include dogs, cats, mice, rabbits, and the like, but are not limited thereto.

The present invention relates to a cosmetic composition having an anti-inflammatory effect, comprising the above-described novel peptide compound or pharmaceutically acceptable salt thereof as an active ingredient.

In the cosmetic composition of the present invention, the novel peptide compound or pharmaceutically acceptable salt thereof may be included at a concentration of 0.001 to 10 µM. A composition comprising an anti-inflammatory active peptide at a concentration of less than 0.001 µM may have a weak anti-inflammatory effect, and if it has a concentration of more than 10 µM, the increase in the effect according to the increase in concentration is not proportional, so it may be inefficient, and there is a problem in that the stability of the formulation is not secured.

When the composition of the present invention is used as a cosmetic composition, as an active ingredient, in addition to the above-described novel peptide compound or pharmaceutically acceptable salt thereof, components commonly used in a cosmetic composition may be additionally included. For example, it may include conventional adjuvants such as antioxidants, stabilizing agents, solubilizers, vitamins, pigments and fragrances, and carriers.

The cosmetic composition may be also prepared in any formulation conventionally prepared in the art, and may be formulated into, for example, a solution, a suspension, an emulsion, a paste, a gel, a cream, a lotion, a powder, a soap, a surfactant-containing cleansing oil, a powder foundation, an emulsion foundation, a wax foundation and a spray and the like, but is not limited thereto. More specifically, it may be prepared in the form of a nourishing cream, an astringent lotion, a softening lotion, a lotion, an essence, a nutrition gel, a massage cream or the like.

When the formulation of the cosmetic composition is a paste, a cream or a gel, animal oil, vegetable oil, wax, paraffin, starch, gum tragacanth, cellulose derivative, polyethylene glycol, silicone, bentonite, silica, talc or zinc oxide, or the like may be used as a carrier component.

When the formulation of the cosmetic composition is a powder or a spray, lactose, talc, silica, aluminum hydroxide, calcium silicate or polyamide powder may be used as a carrier component, and in particular, in the case of a spray, it may additionally include propellants such as chlorofluorohydrocarbon, propane/butane or dimethyl ether.

When the formulation of the cosmetic composition is a solution or an emulsion, a solvent, a solubilizer or an emulsifier is used as a carrier component, and it includes for example, water, ethanol, isopropanol, ethyl carbonate, ethyl acetate, benzyl alcohol, benzyl benzoate, propylene glycol, 1,3-butylglycol oil, glycerol aliphatic esters, fatty acid esters of polyethylene glycol or sorbitan.

When the formulation of the cosmetic composition is a suspension, as a carrier component, a liquid diluent such as water, ethanol or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, tragacanth, or the like may be used.

When the formulation of the cosmetic composition is a surfactant-containing cleansing, as a carrier component, aliphatic alcohol sulfate, aliphatic alcohol ether sulfate, sulfosuccinic acid monoester, isethionate, imidazolinium derivative, methyl taurate, sarcosinate, fatty acid amide ether sulfate, alkylamidobetaine, aliphatic alcohol, fatty acid glyceride, fatty acid diethanolamide, vegetable oil, lanolin derivative, ethoxylated glycerol fatty acid ester, or the like may be used.

MODE FOR CARRYING OUT THE INVENTION

Hereinafter, the present invention will be described in more detail through the examples. These examples are for illustrating the present invention in more detail, and the scope of the present invention is not limited to these examples.

EXAMPLE: PREPARATION OF PEPTIDE

Peptides according to Examples 10 to 125 described in Table 1 below were prepared.

TABLE 1

| No | SEQ ID No. | Example | Sequence |
|---|---|---|---|
| 1 | 1 | Example 10 | Hyp-Gly-Gln-Asp-Gly |
| 2 | 2 | Example 11 | Hyp-Gly-Gln-Asp-Gly-Leu |
| 3 | 3 | Example 12 | Hyp-Gly-Gln-Asp-Gly-Leu-Ala |
| 4 | 4 | Example 13 | Hyp-Gly-Gln-Ala-Gly |
| 5 | 5 | Example 14 | Hyp-Gly-Gln-Ala-Gly-Leu-Ala |
| 6 | 6 | Example 15 | Hyp-Gly-Gln-Asp-Gly-Leu-Ala-Gly |
| 7 | 7 | Example 16 | Gln-Asp-Gly-Leu-Ala-Gly-Pro-Lys |
| 8 | 8 | Example 17 | Hyp-Gly-Gln-Leu-Gly-Leu-Ala-Gly |
| 9 | 9 | Example 18 | Gln-Leu-Gly-Leu-Ala-Gly-Pro-Lys |
| 10 | 10 | Example 19 | Asp-Gly-Leu-Ala-Gly-Pro-Lys |
| 11 | 11 | Example 20 | Leu-Gly-Leu-Ala-Gly-Pro-Lys |
| 12 | 12 | Example 21 | Hyp-Gly-Gln-Asp-Val |
| 13 | 13 | Example 22 | Hyp-Gly-Gln-Asp-Val-Leu |
| 14 | 14 | Example 23 | Hyp-Gly-Gln-Asp-Val-Leu-Ala |
| 15 | 15 | Example 24 | Hyp-Gly-Gln-Asp-Val-Leu-Ala-Gly |
| 16 | 16 | Example 25 | Leu-Ala-Gly-Pro-Lys |
| 17 | 17 | Example 26 | Gly-Leu-Ala-Gly-Pro-Lys |
| 18 | 18 | Example 27 | Hyp-Gly-Leu-Ala-Gly-Pro-Lys |
| 19 | 19 | Example 28 | Hyp-Gly-Gln-Asp-Gly-Pro-Lys |
| 20 | 20 | Example 29 | Gly-Gln-Asp-Gly-Leu-Ala |

TABLE 1-continued

| No | SEQ ID No. | Example | Sequence |
|---|---|---|---|
| 21 | 21 | Example 30 | Gln-Asp-Gly-Leu-Ala-Gly |
| 22 | 22 | Example 31 | Asp-Gly-Leu-Ala-Gly-Pro |
| 23 | 23 | Example 32 | Hyp-Gly-Gln-Asp-Leu |
| 24 | 24 | Example 33 | Hyp-Gly-Gln-Asp-Ala |
| 25 | 25 | Example 34 | Hyp-Gly-Gln-Asp-Val-Leu |
| 26 | 26 | Example 35 | Hyp-Gly-Gln-Asp-Leu-Leu |
| 27 | 27 | Example 36 | Hyp-Gly-Gln-Asp-Ala-Leu |
| 28 | 28 | Example 37 | Hyp-Gly-Gln-Asp-Val-Leu-Ala |
| 29 | 29 | Example 38 | Hyp-Gly-Gln-Asp-Leu-Leu-Ala |
| 30 | 30 | Example 39 | Hyp-Gly-Gln-Asp-Ala-Leu-Ala |
| 31 | 31 | Example 40 | D Hyp-Gly-Gln-Asp-Gly |
| 32 | 32 | Example 41 | cis-4F-Pro-Gly-Gln-Asp-Gly |
| 33 | 33 | Example 42 | trans-4NH$_2$-Pro-Gly-Gln-Asp-Gly |
| 34 | 34 | Example 43 | 4,4-difluoro-Pro-Gly-Gln-Asp-Gly |
| 35 | 35 | Example 44 | 4-methylene-Pro-Gly-Gln-Asp-Gly |
| 36 | 36 | Example 45 | D Hyp-Gly-Gln-Asp-Gly-Leu |
| 37 | 37 | Example 46 | cis-4F-Pro-Gly-Gln-Asp-Gly-Leu |
| 38 | 38 | Example 47 | trans-4NH$_2$-Pro-Gly-Gln-Asp-Gly-Leu |
| 39 | 39 | Example 48 | 4,4-difluoro-Pro-Gly-Gln-Asp-Gly-Leu |
| 40 | 40 | Example 49 | 4-methylene-Pro-Gly-Gln-Asp-Gly-Leu |
| 41 | 41 | Example 50 | D Hyp-Gly-Gln-Asp-Gly-Leu-Ala |
| 42 | 42 | Example 51 | cis-4F Pro-Gly-Gln-Asp-Gly-Leu-Ala |
| 43 | 43 | Example 52 | trans-4NH$_2$-Pro-Gly-Gln-Asp-Gly-Leu-Ala |
| 44 | 44 | Example 53 | 4,4-difluoro-Pro-Gly-Gln-Asp-Gly-Leu-Ala |
| 45 | 45 | Example 54 | 4-methylene-Pro-Gly-Gln-Asp-Gly-Leu-Ala |
| 46 | 46 | Example 55 | 4,4-dimethyl Pro-Gly-Gln-Asp-Gly |
| 47 | 47 | Example 56 | 4,4-dimethyl Pro-Gly-Gln-Asp-Gly-Leu |
| 48 | 48 | Example 57 | 4,4-dimethyl Pro-Gly-Gln-Asp-Gly-Leu-Ala |
| 49 | 49 | Example 58 | Hyp-Gly-D Gln-Asp-Gly |
| 50 | 50 | Example 59 | Hyp-Gly-Gln-D Asp-Gly |
| 51 | 51 | Example 60 | Hyp-Gly-D Gln-Asp-Gly-Leu |

TABLE 1-continued

| No | SEQ ID No. | Example | Sequence |
|---|---|---|---|
| 52 | 52 | Example 61 | Hyp-Gly-Gln-D Asp-Gly-Leu |
| 53 | 53 | Example 62 | Hyp-Gly-Gln-Asp-Gly-D Leu |
| 54 | 54 | Example 63 | Hyp-Gly-D Gln-Asp-Gly-Leu-Ala |
| 55 | 55 | Example 64 | Hyp-Gly-Gln-D Asp-Gly-Leu-Ala |
| 56 | 56 | Example 65 | Hyp-Gly-Gln-Asp-Gly-D Leu-Ala |
| 57 | 57 | Example 66 | Hyp-Gly-Gln-Asp-Gly-Leu-D Ala |
| 58 | 58 | Example 67 | Hyp-Gly-Gln-Glu-Gly |
| 59 | 59 | Example 68 | Hyp-Gly-Gln-Glu-Gly-Leu |
| 60 | 60 | Example 69 | Hyp-Gly-Gln-Glu-Gly-Leu-Ala |
| 61 | 61 | Example 70 | Gln-Glu-Gly-Leu-Ala-Gly |
| 62 | 62 | Example 71 | Hyp-Gly-Gln-Asp-Gly-Val |
| 63 | 63 | Example 72 | Hyp-Gly-Gln-Asp-Gly-Val-Ala |
| 64 | 64 | Example 73 | Hyp-Ala-Gln-Asp-Gly |
| 65 | 65 | Example 74 | Hyp-Val-Gln-Asp-Gly |
| 66 | 66 | Example 75 | Hyp-Leu-Gln-Asp-Gly |
| 67 | 67 | Example 76 | Pro-Gly-Gln-Asp-Gly |
| 68 | 68 | Example 77 | Pro-Gly-Gln-Asp-Gly-Leu |
| 69 | 69 | Example 78 | Pro-Gly-Gln-Asp-Gly-Leu-Ala |
| 70 | 70 | Example 79 | Hyp-Gly-Gln-Asn-Gly-Leu-Ala |
| 71 | 71 | Example 80 | Hyp-Gly-Gln-His-Gly-Leu-Ala |
| 72 | 72 | Example 81 | Hyp-Gly-Gln-Asn-Gly-Leu |
| 73 | 73 | Example 82 | Hyp-Gly-Gln-His-Gly-Leu |
| 74 | 74 | Example 83 | Hyp-Gly-Gln-Asp-Aib-Leu-Ala |
| 75 | 75 | Example 84 | Hyp-Gly-Gln-Aib-Gly-Leu |
| 76 | 76 | Example 85 | Hyp-Gly-Gln-Asp-Aib |
| 77 | 77 | Example 86 | Hyp-Gly-Gln-Glu-Leu-Leu-Ala |
| 78 | 78 | Example 87 | Hyp-Gly-Gln-Glu-Val-Leu-Ala |
| 79 | 79 | Example 88 | Hyp-Gly-Gln-Glu-Leu-Leu |
| 80 | 80 | Example 89 | Hyp-Gly-Gln-Glu-Val-Leu |
| 81 | 81 | Example 90 | Hyp-Gly-Gln-Glu-Leu |
| 82 | 82 | Example 91 | Hyp-Gly-Gln-Glu-Val |
| 83 | 83 | Example 92 | Hyp-Gly-Gln-Glu-Aib-Leu-Ala |
| 84 | 84 | Example 93 | Hyp-Gly-Gln-Glu-tert Leu-Leu-Ala |
| 85 | 85 | Example 94 | Hyp-Gly-Gln-Glu-Phenyl Gly-Leu-Ala |
| 86 | 86 | Example 95 | Hyp-Gly-Gln-Leu-Val |
| 87 | 87 | Example 96 | Hyp-Gly-Gln-Leu-Leu-Leu-Ala |
| 88 | 88 | Example 97 | Hyp-Gly-Gln-Leu-Val-Leu-Ala |
| 89 | 89 | Example 98 | Hyp-Gly-Gln-Leu-Leu-Leu |
| 90 | 90 | Example 99 | Hyp-Gly-Gln-Leu-Val-Leu |
| 91 | 91 | Example 100 | Hyp-Gly-Gln-Asu-Gly |
| 92 | 92 | Example 101 | Hyp-Gly-Gln-Asu-Gly-Leu |
| 93 | 93 | Example 102 | Hyp-Gly-Gln-Asu-Gly-Leu-Ala |
| 94 | 94 | Example 103 | Hyp-Gly-Gln-Asu-Gly-Leu-Ala-Gly |
| 95 | 95 | Example 104 | Gln-Asu-Gly-Leu-Ala-Gly-Pro-Lys |
| 96 | 96 | Example 105 | Asu-Gly-Leu-Ala-Gly-Pro-Lys |
| 97 | 97 | Example 106 | Hyp-Gly-Gln-Asp-Gly (isopropyl ester) |
| 98 | 98 | Example 107 | Hyp-Gly-Gln-Asp-Gly-Leu (isopropyl ester) |
| 99 | 99 | Example 108 | Hyp-Gly-Gln-Asp-Gly-Leu-Ala (isopropyl ester) |
| 100 | 100 | Example 109 | Hyp-Gly-Gln-Asu-Gly (isopropyl ester) |
| 101 | 101 | Example 110 | Hyp-Gly-Gln-Asp (isopropyl ester)-Gly (isopropyl ester) |
| 102 | 102 | Example 111 | Hyp-Gly-Gln-Asu-Gly-Leu (isopropyl ester) |
| 103 | 103 | Example 112 | Hyp-Gly-Gln-Asp (isopropyl ester)-Gly-Leu (isopropyl ester) |
| 104 | 104 | Example 113 | Hyp-Gly-Gln-Asu-Gly-Leu-Ala (isopropyl ester) |
| 105 | 105 | Example 114 | Hyp-Gly-Gln-Asp (isopropyl ester)-Gly-Leu-Ala (isopropyl ester) |
| 106 | 106 | Example 115 | Hyp-Gly-Gln-Asp (isopropyl ester)-Gly |
| 107 | 107 | Example 116 | Hyp-Gly-Gln-Asp (isopropyl ester)-Gly-Leu |
| 108 | 108 | Example 117 | Hyp-Gly-Gln-Asp (isopropyl ester)-Gly-Leu-Ala |
| 109 | 109 | Example 118 | Gln-Asu-Gly-Leu-Ala-Gly |
| 114 | 110 | Example 119 | Hyp-Gly-Gln-Ala-Val |
| 115 | 111 | Example 120 | Hyp-Gly-Gln-Ala-Leu |
| 116 | 112 | Example 121 | Hyp-Gly-Gln-Leu-Leu |
| 117 | 113 | Example 122 | Hyp-Gly-Gln-Ala-Gly-Leu |
| 118 | 114 | Example 123 | Hyp-Gly-Gln-Ala-Leu-Leu |
| 119 | 115 | Example 124 | Hyp-Gly-Gln-Ala-Val-Leu |
| 120 | 116 | Example 125 | Hyp-Gly-Gln-D Asp-Leu |

(1) Example 1 (Trityl Resin-Lys (Boc) Step)

2.2 L of dichloromethane (hereinafter, MC) was injected into 150 g of 2-chlorotrityl resin, stirred for 1 hour, and then dehydrated. 205.22 g of Fmoc-Lys (Boc)-OH, 1.8 L of MC, and 153 ml of N,N-diisopropylethylamine (hereinafter, DIEA) were injected into the other reaction part, and stirred for 10 minutes to dissolve, and then injected into the reaction part containing resin, and stirred at room temperature for 4 hours. They were stirred and then dehydrated. 1.8 L of MC was injected into the dehydrated solid, and stirred for 10 minutes, and then dehydrated, and this process was repeated twice. The dissolved solution of 1530 ml of MC, 180 ml of MeOH, 90 ml of DIEA was injected, and stirred for 30 minutes, and then dehydrated, and this process was repeated twice. After drying with nitrogen for 15 hours, the dried solid was dried under vacuum at 25° C. for 15 hours to obtain 267 g of a final solid. It was found that the loading rate was calculated to be 0.82 mmol/g.

(2) Example 2 (Trityl Resin-Pro Step)

It was found that the loading rate was calculated to be a total of 0.61 mmol/g in the same manner as in Example 1 using Fmoc-Pro-OH.

(3) Example 3 (Trityl Resin-Gly Step)

It was found that the loading rate was calculated to be a total of 0.96 mmol/g in the same manner as in Example 1 using Fmoc-Gly-OH.

(4) Example 4 (Trityl Resin-Ala Step)

It was found that the loading rate was calculated to be a total of 0.87 mmol/g in the same manner as in Example 1 using Fmoc-Ala-OH.

(5) Example 5 (Trityl Resin-Leu Step)

It was found that the loading rate was calculated to be a total of 0.97 mmol/g in the same manner as in Example 1 using Fmoc-Leu-OH.

(6) Example 6 (Trityl Resin-Asp (OtBu) Step)

It was found that the loading rate was calculated to be a total of 0.94 mmol/g in the same manner as in Example 1 using Fmoc-Asp (OtBu)-OH.

(7) Example 7 (Trityl Resin-Glu (OtBu) Step)

It was found that the loading rate was calculated to be a total of 0.62 mmol/g in the same manner as in Example 1 using Fmoc-Glu (OtBu)-OH.

(8) Example 8 (Trityl Resin-Val Step)

It was found that the loading rate was calculated to be a total of 0.992 mmol/g in the same manner as in Example 1 using Fmoc-Val-OH.

(9) Example 9 (Cleavage Step)

99 ml of 20% piperidie/DMF (dimethylformamide) was injected into the compound in which the desired amino acid sequence is bound to the trityl group-introduced resin, which has been synthesized, and dehydrated by stirring for 10 minutes. This process was repeated twice. 99 ml of DMF was injected and dehydrated by stirring for 10 minutes. This process was repeated twice. 99 ml of MC was injected and then dehydrated by stirring for 10 minutes. This process was repeated three times. 30 ml of MC, 70 ml of TFA (trifluoroacetic acid), and 1 ml of $H_2O$ were injected into the other reaction part, and dissolved, and then injected into the reaction part. They were stirred for 4 hours at room temperature and filtered. The filtered solution was concentrated to ½ under reduced pressure based on the volume of the filtered solution. The concentrated solution was added dropwise to the reaction part containing 300 ml of IPE (isopropyl ether) and stirred for 30 minutes. A crude solid can be obtained by dehydrating the precipitated solid.

(10) Example 10

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.15 g of Fmoc-Asp (OtBu)-OH, 13.52 g of 1-hydroxy-1H-benzotriazole (hereinafter, HOBt), and 900 ml of DMF were dissolved by stirring for 10 minutes. The dissolved solution was injected into the trityl-Gly reaction part, and then 31.32 ml of diisopropyl carbodiimide (hereinafter, DIC) was injected and dehydrated by stirring for 4 hours at room temperature. 16.7 g of a crude solid can be obtained by repeating a series of processes according to the amino acid sequence according to Table 1 and performing the cleavage step (Example 9). 4 g of the crude solid was purified through Prep LC and then lyophilized to obtain 1.8 g of a final solid.

(11) Example 11

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.7 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 21.1 g of a crude solid can be obtained by repeating a series of processes according to the amino acid sequence according to Table 1 and performing the cleavage step (Example 9). 4 g of the crude solid was purified through Prep LC and then lyophilized to obtain 2.1 g of a final solid.

(12) Example 12

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.3 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 24.4 g of a crude solid can be obtained by repeating a series of processes according to the amino acid sequence according to Table 1 and performing the cleavage step (Example 9). 4 g of the crude solid was purified through Prep LC and then lyophilized to obtain 2.0 g of a final solid.

(13) Example 13

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 31.1 g of Fmoc-Ala-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 24.4 g of a crude solid can be obtained by repeating a series of processes according to the amino acid sequence according to Table 1 and performing the cleavage step (Example 9). 4 g of the crude solid was purified through Prep LC and then lyophilized to obtain 1.6 g of a final solid.

(14) Example 14

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 31.1 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 20.2 g of a crude solid can be obtained by repeating a series of processes according to the amino acid sequence according to Table 1 and performing the cleavage step (Example 9). 4 g of the crude solid was purified through Prep LC and then lyophilized to obtain 1.9 g of a final solid.

(15) Example 15

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 31.13 g of Fmoc-Ala-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 27.5 g of a crude solid can be obtained by repeating a series of processes according to the amino acid sequence according to Table 1 and performing the cleavage step (Example 9). 4 g of the crude solid was purified through Prep LC and then lyophilized to obtain 2.1 g of a final solid.

(16) Example 16

400 ml of 20% piperidine/DMF was injected into 50 mmol of lysine loaded in the same manner as in Example 1 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.73 g of Fmoc-Pro-OH, 13.52 g of HOBt, and 900 ml of DMF were dissolved by stirring for 10 minutes. The dissolved solution was injected into the trityl-Lys reaction part, and then 31.32 ml of DIC was injected and dehydrated by stirring for 4 hours at room temperature. 28.3 g of a crude solid can be obtained by repeating a series of processes according to the amino acid sequence according to Table 1 and performing the cleavage step (Example 9). 4 g of the crude solid was purified through Prep LC and then lyophilized to obtain 2.2 g of a final solid.

(17) Example 17

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 31.13 g of Fmoc-Ala-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 23.1 g of a crude solid can be obtained by repeating a series of processes according to the amino acid sequence according to Table 1 and performing the cleavage step (Example 9). 4 g of the crude solid was purified through Prep LC and then lyophilized to obtain 2.0 g of a final solid.

(18) Example 18

400 ml of 20% piperidine/DMF was injected into 50 mmol of lysine loaded in the same manner as in Example 1 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.73 g of Fmoc-Pro-OH, 13.52 g of HOBt, and 900 ml of DMF were dissolved by stirring for 10 minutes. The dissolved solution was injected into the trityl-Lys reaction part, and then 31.32 ml of DIC was injected and dehydrated by stirring for 4 hours at room temperature. 26.4 g of a crude solid can be obtained by repeating a series of processes according to the amino acid sequence according to Table 1 and performing the cleavage step (Example 9). 4 g of the crude solid was purified through Prep LC and then lyophilized to obtain 2.9 g of a final solid.

(19) Example 19

400 ml of 20% piperidine/DMF was injected into 50 mmol of lysine loaded in the same manner as in Example 1 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.73 g of Fmoc-Pro-OH, 13.52 g of HOBt, and 900 ml of DMF were dissolved by stirring for 10 minutes. The dissolved solution was injected into the trityl-Lys reaction part, and then 31.32 ml of DIC was injected and dehydrated by stirring for 4 hours at room temperature. 21.37 g of a crude solid can be obtained by repeating a series of processes according to the amino acid sequence according to Table 1 and performing the cleavage step (Example 9). 4 g of the crude solid was purified through Prep LC and then lyophilized to obtain 2.2 g of a final solid.

(20) Example 20

400 ml of 20% piperidine/DMF was injected into 50 mmol of lysine loaded in the same manner as in Example 1 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.73 g of Fmoc-Pro-OH, 13.52 g of HOBt, and 900 ml of DMF were dissolved by stirring for 10 minutes. The dissolved solution was injected into the trityl-Lys reaction part, and then 31.32 ml of DIC was injected and dehydrated by stirring for 4 hours at room temperature. 23.25 g of a crude solid can be obtained by repeating a series of processes according to the amino acid sequence according to Table 1 and performing the cleavage step (Example 9). 4 g of the crude solid was purified through Prep LC and then lyophilized to obtain 1.8 g of a final solid.

(21) Example 21

400 ml of 20% piperidine/DMF was injected into 50 mmol of valine loaded in the same manner as in Example 1 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Val reaction part, and then 31.32 ml of DIC was injected and dehydrated by stirring for 4 hours at room temperature. 23.25 g of a crude solid can be obtained by repeating a series of processes according to the amino acid sequence according to Table 1 and performing the cleavage step (Example 9). 4 g of the crude solid was purified through Prep LC and then lyophilized to obtain 1.8 g of a final solid.

(22) Example 22

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.93 g of Fmoc-Val-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 20.76 g of a crude solid can be obtained by repeating a series of processes according to the amino acid sequence according to Table 1 and performing the cleavage step (Example 9). 4 g of the crude solid was purified through Prep LC and then lyophilized to obtain 1.4 g of a final solid.

(23) Example 23

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 20.76 g of a crude solid can be obtained by repeating a series of processes according to the amino acid sequence according to Table 1 and performing the cleavage step (Example 9). 4 g of the crude solid was purified through Prep LC and then lyophilized to obtain 1.8 g of a final solid.

(24) Example 24

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Ala-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 30.26 g of a crude solid can be obtained by repeating a series of processes according to the amino acid sequence according to Table 1 and performing the cleavage step (Example 9). 4 g of the crude solid was purified through Prep LC and then lyophilized to obtain 1.9 g of a final solid.

(25) Example 25

400 ml of 20% piperidine/DMF was injected into 50 mmol of lysine loaded in the same manner as in Example 1 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Pro-OH, 13.52 g of HOBt, and 900 ml of DMF were dissolved by stirring for 10 minutes. The dissolved solution was injected into the trityl-Lys reaction part, and then 31.32 ml of DIC was injected and dehydrated by stirring for 4 hours at room temperature. 16.16 g of a crude solid can be obtained by repeating a series of processes according to the amino acid sequence according to Table 1 and performing the cleavage step (Example 9). 4 g of the crude solid was purified through Prep LC and then lyophilized to obtain 2.7 g of a final solid.

(26) Example 26

400 ml of 20% piperidine/DMF was injected into 50 mmol of lysine loaded in the same manner as in Example 1 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.73 g of Fmoc-Pro-OH, 13.52 g of HOBt, and 900 ml of DMF were dissolved by stirring for 10 minutes. The dissolved solution was injected into the trityl-Lys reaction part, and then 31.32 ml of DIC was injected and dehydrated by stirring for 4 hours at room temperature. 18.63 g of a crude solid can be obtained by repeating a series of processes according to the amino acid sequence according to Table 1 and performing the cleavage step (Example 9). 4 g of the crude solid was purified through Prep LC and then lyophilized to obtain 3.0 g of a final solid.

(27) Example 27

400 ml of 20% piperidine/DMF was injected into 50 mmol of lysine loaded in the same manner as in Example 1 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.73 g of Fmoc-Pro-OH, 13.52 g of HOBt, and 900 ml of DMF were dissolved by stirring for 10 minutes. The dissolved solution was injected into the trityl-Lys reaction part, and then 31.32 ml of DIC was injected and dehydrated by stirring for 4 hours at room temperature. 18.63 g of a crude solid can be obtained by repeating a series of processes according to the amino acid sequence according to Table 1 and performing the cleavage step (Example 9). 4 g of the crude solid was purified through Prep LC and then lyophilized to obtain 3.0 g of a final solid.

(28) Example 28

400 ml of 20% piperidine/DMF was injected into 50 mmol of lysine loaded in the same manner as in Example 1 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.73 g of Fmoc-Pro-OH, 13.52 g of HOBt, and 900 ml of DMF were dissolved by stirring for 10 minutes. The dissolved solution was injected into the trityl-Lys reaction part, and then 31.32 ml of DIC was injected and dehydrated by stirring for 4 hours at room temperature. 21.35 g of a crude solid can be obtained by repeating a series of processes according to the amino acid sequence according to Table 1 and performing the cleavage step (Example 9). 4 g of the crude solid was purified through Prep LC and then lyophilized to obtain 2.7 g of a final solid.

(29) Example 29

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 20.80 g of a crude solid can be obtained by repeating a series of processes according to the amino acid sequence according to Table 1 and performing the cleavage step (Example 9). 4 g of the crude solid was purified through Prep LC and then lyophilized to obtain 3.3 g of a final solid.

(30) Example 30

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 31.13 g of Fmoc-Ala-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 19.28 g of a crude solid can be obtained by repeating a series of processes according to the amino acid sequence according to Table 1 and performing the cleavage step (Example 9). 4 g of the crude solid was purified through Prep LC and then lyophilized to obtain 1.9 g of a final solid.

(31) Example 31

400 ml of 20% piperidine/DMF was injected into 50 mmol of proline loaded in the same manner as in Example 2 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Pro reaction part, and then 31.32 ml of DIC was injected and dehydrated by stirring for 4 hours at room temperature. 18.87 g of a crude solid can be obtained by repeating a series of processes according to the amino acid sequence according to Table 1 and performing the cleavage step (Example 9). 4 g of the crude solid was purified through Prep LC and then lyophilized to obtain 2.4 g of a final solid.

(32) Example 32

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 20.30 g of a crude solid can be obtained by repeating a series of processes according to the amino acid sequence according to Table 1 and performing the cleavage step (Example 9). 4 g of the crude solid was purified through Prep LC and then lyophilized to obtain 2.0 g of a final solid.

(33) Example 33

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 17.10 g of a crude solid can be obtained by repeating a series of processes according to the amino acid sequence according to Table 1 and performing the cleavage step (Example 9). 4 g of the crude solid was purified through Prep LC and then lyophilized to obtain 2.5 g of a final solid.

(34) Example 34

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.93 g of Fmoc-Val-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 20.62 g of a crude solid can be obtained by repeating a series of processes according to the amino acid sequence according to Table 1 and performing the cleavage step (Example 9). 4 g of the crude solid was purified through Prep LC and then lyophilized to obtain 2.1 g of a final solid.

(35) Example 35

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 22.48 g of a crude solid can be obtained by repeating a series of processes according to the amino acid sequence according to Table 1 and performing the cleavage step (Example 9). 4 g of the crude solid was purified through Prep LC and then lyophilized to obtain 2.0 g of a final solid.

(36) Example 36

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 31.13 g of Fmoc-Ala-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 22.12 g of a crude solid can be obtained by repeating a series of processes according to the amino acid sequence according to Table 1 and performing the cleavage step (Example 9). 4 g of a solid was purified through Prep LC and then lyophilized to obtain 2.1 g of a final solid.

(37) Example 37

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 22.32 g of a crude solid can be obtained by repeating a series of processes according to the amino acid sequence according to Table 1 and performing the cleavage step (Example 9). 4 g of the crude solid was purified through Prep LC and then lyophilized to obtain 1.9 g of a final solid.

(38) Example 38

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 24.80 g of a crude solid can be obtained by repeating a series of processes according to the amino acid sequence according to Table 1 and performing the cleavage step (Example 9). 4 g of the crude solid was purified through Prep LC and then lyophilized to obtain 2.1 g of a final solid.

(39) Example 39

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 24.50 g of a crude solid can be obtained by repeating a series of processes according to the amino acid sequence according to Table 1 and performing the cleavage step (Example 9). 4 g of the crude solid was purified through Prep LC and then lyophilized to obtain 2.7 g of a final solid.

(40) Example 40

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 15.26 g of a crude solid can be obtained by repeating a series of processes according to the amino acid sequence according to Table 1 and performing the cleavage step (Example 9). 4 g of the crude solid was purified through Prep LC and then lyophilized to obtain 2.4 g of a final solid.

(41) Example 41

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 15.91 g of a crude solid can be obtained by repeating a series of processes according to the amino acid sequence according to Table 1 and performing the cleavage step (Example 9). 4 g of the crude solid was purified through Prep LC and then lyophilized to obtain 1.5 g of a final solid.

(42) Example 42

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 19.82 g of a crude solid can be obtained by repeating a series of processes according to the amino acid sequence according to Table 1 and performing the cleavage step (Example 9). 4 g of the crude solid was purified through Prep LC and then lyophilized to obtain 1.6 g of a final solid.

(43) Example 43

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 17.90 g of a crude solid can be obtained by repeating a series of processes according to the amino acid sequence according to Table 1 and performing the cleavage step (Example 9). 4 g of the crude solid was purified through Prep LC and then lyophilized to obtain 0.9 g of a final solid.

(44) Example 44

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 14.32 g of a crude solid can be obtained by repeating a series of processes according to the amino acid sequence according to Table 1 and performing the cleavage step (Example 9). 4 g of the crude solid was purified through Prep LC and then lyophilized to obtain 1.7 g of a final solid.

(45) Example 45

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 18.62 g of a crude solid can be obtained by repeating a series of processes according to the amino acid sequence according to Table 1 and performing the cleavage step (Example 9). 4 g of the crude solid was purified through Prep LC and then lyophilized to obtain 1.2 g of a final solid.

(46) Example 46

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 20.00 g of a crude solid can be obtained by repeating a series of processes according to the amino acid sequence according to Table 1 and performing the cleavage step (Example 9). 4 g of the crude solid was purified through Prep LC and then lyophilized to obtain 1.5 g of a final solid.

(47) Example 47

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 17.81 g of a crude solid can be obtained by repeating a series of processes according to the amino acid sequence according to Table 1 and performing the cleavage step (Example 9). 4 g of the crude solid was purified through Prep LC and then lyophilized to obtain 1.2 g of a final solid.

(48) Example 48

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 17.81 g of a crude solid can be obtained by repeating a series of processes according to the amino acid sequence according to Table 1 and performing the cleavage step (Example 9). 4 g of the crude solid was purified through Prep LC and then lyophilized to obtain 1.2 g of a final solid.

(49) Example 49

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 21.54 g of a crude solid can be obtained by repeating a series of processes according to the amino acid sequence according to Table 1 and performing the cleavage step (Example 9). 4 g of the crude solid was purified through Prep LC and then lyophilized to obtain 2.4 g of a final solid.

(50) Example 50

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 18.23 g of a crude solid can be obtained by repeating a series of processes according to the amino acid sequence according to Table 1 and performing the cleavage step (Example 9). 4 g of the crude solid was purified through Prep LC and then lyophilized to obtain 1.6 g of a final solid.

(51) Example 51

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 9.14 g of a crude solid can be obtained by repeating a series of processes according to the amino acid sequence according to Table 1 and performing the cleavage step (Example 9). 4 g of the crude solid was purified through Prep LC and then lyophilized to obtain 1.5 g of a final solid.

(52) Example 52

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 17.23 g of a crude solid can be obtained by repeating a series of processes according to the amino acid sequence according to Table 1 and performing the cleavage step (Example 9). 4 g of the crude solid was purified through Prep LC and then lyophilized to obtain 1.5 g of a final solid.

(53) Example 53

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 10.56 g of a crude solid can be obtained by repeating a series of processes according to the amino acid sequence according to Table 1 and performing the cleavage step (Example 9). 4 g of the crude solid was purified through Prep LC and then lyophilized to obtain 0.9 g of a final solid.

(54) Example 54

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 13.94 g of a crude solid can be obtained by repeating a series of processes according to the amino acid sequence according to Table 1 and performing the cleavage step (Example 9). 4 g of the crude solid was purified through Prep LC and then lyophilized to obtain 1.2 g of a final solid.

(55) Example 55

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.15 g of Fmoc-Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 17.29 g of a crude solid can be obtained by repeating a series of processes according to the amino acid sequence according to Table 1 and performing the cleavage step (Example 9). 4 g of the crude solid was purified through Prep LC and then lyophilized to obtain 1.8 g of a final solid.

(56) Example 56

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 18.69 g of a crude solid can be obtained by repeating a series of processes according to the amino acid sequence according to Table 1 and performing the cleavage step (Example 9). 4 g of the crude solid was purified through Prep LC and then lyophilized to obtain 1.1 g of a final solid.

(57) Example 57

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 21.09 g of a crude solid can be obtained by repeating a series of processes according to the amino acid sequence according to Table 1 and performing the cleavage step (Example 9). 4 g of the crude solid was purified through Prep LC and then lyophilized to obtain 2.1 g of a final solid.

(58) Example 58

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.15 g of Fmoc-Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 15.67 g of a crude solid can be obtained by repeating a series of processes according to the amino acid sequence according to Table 1 and performing the cleavage step (Example 9). 4 g of the crude solid was purified through Prep LC and then lyophilized to obtain 1.3 g of a final solid.

(59) Example 59

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.15 g of Fmoc-D Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 17.21 g of a crude solid can be obtained by repeating a series of processes according to the amino acid sequence according to Table 1 and performing the cleavage step (Example 9). 4 g of the crude solid was purified through Prep LC and then lyophilized to obtain 2.2 g of a final solid.

(60) Example 60

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 20.48 g of a crude solid can be obtained by repeating a series of processes according to the amino acid sequence according to Table 1 and performing the cleavage step (Example 9). 4 g of the crude solid was purified through Prep LC and then lyophilized to obtain 1.9 g of a final solid.

(61) Example 61

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 21.32 g of a crude solid can be obtained by repeating a series of processes according to the amino acid sequence according to Table 1 and performing the cleavage step (Example 9). 4 g of the crude solid was purified through Prep LC and then lyophilized to obtain 1.6 g of a final solid.

(62) Example 62

400 ml of 20% piperidine/DMF was injected into 50 mmol of D leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-D Leu reaction part, and then 31.32 ml of DIC was injected and dehydrated by stirring for 4 hours at room temperature. 24.76 g of a crude solid can be obtained by repeating a series of processes according to the amino acid sequence according to Table 1 and performing the cleavage step (Example 9). 4 g of the crude solid was purified through Prep LC and then lyophilized to obtain 1.9 g of a final solid.

(63) Example 63

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 23.68 g of a crude solid can be obtained by repeating a series of processes according to the amino acid sequence according to Table 1 and performing the cleavage step (Example 9). 4 g of the crude solid was purified through Prep LC and then lyophilized to obtain 1.6 g of a final solid.

(64) Example 64

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and dehydrated by stirring for 10 minutes. This process was repeated three times. In the other reaction part, 29.73 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 24.15 g of a crude solid can be obtained by repeating a series of processes according to the amino acid sequence according to Table 1 and performing the cleavage step (Example 9). 4 g of the crude solid was purified through Prep LC and then lyophilized to obtain 1.7 g of a final solid.

(65) Example 65

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-D Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 26.98 g of a crude solid can be obtained by repeating a series of processes according to the amino acid sequence according to Table 1 and performing the cleavage step (Example 9). 4 g of the crude solid was purified through Prep LC and then lyophilized to obtain 1.7 g of a final solid.

(66) Example 66

400 ml of 20% piperidine/DMF was injected into 50 mmol of D alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Leu-OH, 13.52 g of HOBt, and 900 ml of DMF were dissolved by stirring for 10 minutes. The dissolved solution was injected into the trityl-D Ala reaction part, and then 31.32 ml of DIC was injected and dehydrated by stirring for 4 hours at room temperature. 22.78 g of a crude solid can be obtained by repeating a series of processes according to the amino acid sequence according to Table 1 and performing the cleavage step (Example 9). 4 g of the crude solid was purified through Prep LC and then lyophilized to obtain 1.9 g of a final solid.

(67) Example 67

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 42.54 g of Fmoc-Glu (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 17.18 g of a crude solid can be obtained by repeating a series of processes according to the amino acid sequence according to Table 1 and performing the cleavage step (Example 9). 4 g of the crude solid was purified through Prep LC and then lyophilized to obtain 1.6 g of a final solid.

(68) Example 68

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 19.11 g of a crude solid can be obtained by repeating a series of processes according to the amino acid sequence according to Table 1 and performing the cleavage step (Example 9). 4 g of the crude solid was purified through Prep LC and then lyophilized to obtain 2.8 g of a final solid.

(69) Example 69

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 20.40 g of a crude solid can be obtained by repeating a series of processes according to the amino acid sequence according to Table 1 and performing the cleavage step (Example 9). 4 g of the crude solid was purified through Prep LC and then lyophilized to obtain 2.2 g of a final solid.

(70) Example 70

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Ala-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 17.78 g of a crude solid can be obtained by repeating a series of processes according to the amino acid sequence according to Table 1 and performing the cleavage step (Example 9). 4 g of the crude solid was purified through Prep LC and then lyophilized to obtain 3.1 g of a final solid.

(71) Example 71

400 ml of 20% piperidine/DMF was injected into 50 mmol of valine loaded in the same manner as in Example 8 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Val reaction part, and then 31.32 ml of DIC was injected and dehydrated by stirring for 4 hours at room temperature. 15.24 g of a crude solid can be obtained by repeating a series of processes according to the amino acid sequence according to Table 1 and performing the cleavage step (Example 9). 4 g of the crude solid was purified through Prep LC and then lyophilized to obtain 1.1 g of a final solid.

(72) Example 72

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.93 g of Fmoc-Val-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 22.23 g of a crude solid can be obtained by repeating a series of processes according to the amino acid sequence according to Table 1 and performing the cleavage step (Example 9). 4 g of the crude solid was purified through Prep LC and then lyophilized to obtain 0.8 g of a final solid.

(73) Example 73

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 18.04 g of a crude solid can be obtained by repeating a series of processes according to the amino acid sequence according to Table 1 and performing the cleavage step (Example 9). 4 g of the crude solid was purified through Prep LC and then lyophilized to obtain 2.6 g of a final solid.

(74) Example 74

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 18.17 g of a crude solid can be obtained by repeating a series of processes according to the amino acid sequence according to Table 1 and performing the cleavage step (Example 9). 4 g of the crude solid was purified through Prep LC and then lyophilized to obtain 2.1 g of a final solid.

(75) Example 75

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 16.94 g of a crude solid can be obtained by repeating a series of processes according to the amino acid sequence according to Table 1 and performing the cleavage step (Example 9). 4 g of the crude solid was purified through Prep LC and then lyophilized to obtain 1.6 g of a final solid.

(76) Example 76

400 ml of 20% piperidine/DMF was injected into 50 mmol of glycine loaded in the same manner as in Example 3 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Gly reaction part, and then 31.32 ml of DIC was injected and dehydrated by stirring for 4 hours at room temperature. 16.87 g of a crude solid can be obtained by repeating a series of processes according to the amino acid sequence according to Table 1 and performing the cleavage step (Example 9). 4 g of the crude solid was purified through Prep LC and then lyophilized to obtain 2.1 g of a final solid.

(77) Example 77

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 19.35 g of a crude solid can be obtained by repeating a series of processes according to the amino acid sequence according to Table 1 and performing the cleavage step (Example 9). 4 g of the crude solid was purified through Prep LC and then lyophilized to obtain 1.8 g of a final solid.

(78) Example 78

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 19.90 g of a crude solid can be obtained by repeating a series of processes according to the amino acid sequence according to Table 1 and performing the cleavage step (Example 9). 4 g of the crude solid was purified through Prep LC and then lyophilized to obtain 2.2 g of a final solid.

(79) Example 79

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 14.37 g of a crude solid can be obtained by repeating a series of processes according to the amino acid sequence according to Table 1 and performing the cleavage step (Example 9). 4 g of the crude solid was purified through Prep LC and then lyophilized to obtain 1.8 g of a final solid.

(80) Example 80

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 21.38 g of a crude solid can be obtained by repeating a series of processes according to the amino acid sequence according to Table 1 and performing the cleavage step (Example 9). 4 g of the crude solid was purified through Prep LC and then lyophilized to obtain 2.3 g of a final solid.

(81) Example 81

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 23.27 g of a crude solid can be obtained by repeating a series of processes according to the amino acid sequence according to Table 1 and performing the cleavage step (Example 9). 4 g of the crude solid was purified through Prep LC and then lyophilized to obtain 1.7 g of a final solid.

(82) Example 82

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 20.64 g of a crude solid can be obtained by repeating a series of processes according to the amino acid sequence according to Table 1 and performing the cleavage step (Example 9). 3 g of the crude solid was purified through Prep LC and then lyophilized to obtain 1.3 g of a final solid.

(83) Example 83

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 450 ml of DMF were dissolved by stirring for 10 minutes. The dissolved solution was injected into the trityl-Ala reaction part, and then 31.32 ml of DIC was injected and dehydrated by stirring for 4 hours at room temperature. 14.68 g of a crude solid can be obtained by repeating a series of processes according to the amino acid sequence according to Table 1 and performing the cleavage step (Example 9). 4 g of the crude solid was purified through Prep LC and then lyophilized to obtain 0.5 g of a final solid.

(84) Example 84

400 ml of 20% piperidine/DMF was injected into 50 mmol of leucine loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 29.73 g of Fmoc-Gly-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 14.68 g of a crude solid can be obtained by repeating a series of processes according to the amino acid sequence according to Table 1 and performing the cleavage step (Example 9). 3 g of the crude solid was purified through Prep LC and then lyophilized to obtain 1.0 g of a final solid.

(85) Example 85

400 ml of 20% piperidine/DMF was injected into 50 mmol of Aib (alpa-Me-Ala) loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.14 g of Fmoc-Asp (OtBu)-OH, 13.52 g of HOBt, and 900 ml of DMF were dissolved by stirring for 10 minutes. The dissolved solution was injected into the trityl-Aib reaction part, and then 31.32 ml of DIC was injected and dehydrated by stirring for 4 hours at room temperature. 8.96 g of a crude solid can be obtained by repeating a series of processes according to the amino acid sequence according to Table 1 and performing the cleavage step (Example 9). 1.5 g of the crude solid was purified through Prep LC and then lyophilized to obtain 0.3 g of a final solid.

(86) Example 86

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 15.41 g of a crude solid can be obtained by repeating a series of processes according to the amino acid sequence according to Table 1 and performing the cleavage step (Example 9). 5 g of the crude solid was purified through Prep LC and then lyophilized to obtain 1.42 g of a final solid.

(87) Example 87

400 ml of 20% piperidine/DMF was injected into 50 mmol of alanine loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 17.53 g of a crude solid can be obtained by repeating a series of processes according to the amino acid sequence according to Table 1 and performing the cleavage step (Example 9). 3 g of the crude solid was purified through Prep LC and then lyophilized to obtain 0.53 g of a final solid.

(88) Example 88

400 ml of 20% piperidine/DMF was injected into 50 mmol of Leu loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 20.76 g of a crude solid can be obtained by repeating a series of processes according to the amino acid sequence according to Table 1 and performing the cleavage step (Example 9). 5 g of the crude solid was purified through Prep LC and then lyophilized to obtain 2.3 g of a final solid.

(89) Example 89

400 ml of 20% piperidine/DMF was injected into 50 mmol of Leu loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.93 g of Fmoc-Val-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 18.81 g of a crude solid can be obtained by repeating a series of processes according to the amino acid sequence according to Table 1 and performing the cleavage step (Example 9). 5 g of the crude solid was purified through Prep LC and then lyophilized to obtain 1.6 g of a final solid.

(90) Example 90

400 ml of 20% piperidine/DMF was injected into 50 mmol of Leu loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 42.54 g of Fmoc-Glu (OtBu)-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 18.66 g of a crude solid can be obtained by repeating a series of processes according to the amino acid sequence according to Table 1 and performing the cleavage step (Example 9). 5 g of the crude solid was purified through Prep LC and then lyophilized to obtain 2.6 g of a final solid.

(91) Example 91

400 ml of 20% piperidine/DMF was injected into 50 mmol of Val loaded in the same manner as in Example 8 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 42.54 g of Fmoc-Glu (OtBu)-OH, 13.52 g of HOBt, and 900 ml of DMF were dissolved by stirring for 10 minutes. The dissolved solution was injected into the trityl-Val reaction part, and then 31.32 ml of DIC was injected and dehydrated by stirring for 4 hours at room temperature. 19.74 g of a crude solid can be obtained by repeating a series of processes according to the amino acid sequence according to Table 1 and performing the cleavage step (Example 9). 5 g of the crude solid was purified through Prep LC and then lyophilized to obtain 0.4 g of a final solid.

(92) Example 92

400 ml of 20% piperidine/DMF was injected into 50 mmol of Ala loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 22.48 g of a crude solid can be obtained by repeating a series of processes according to the amino acid sequence according to Table 1 and performing the cleavage step (Example 9). 3 g of the crude solid was purified through Prep LC and then lyophilized to obtain 0.11 g of a final solid.

(93) Example 93

400 ml of 20% piperidine/DMF was injected into 50 mmol of Ala loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 20.35 g of a crude solid can be obtained by repeating a series of processes according to the amino acid sequence according to Table 1 and performing the cleavage step (Example 9). 3 g of the crude solid was purified through Prep LC and then lyophilized to obtain 0.65 g of a final solid.

(94) Example 94

400 ml of 20% piperidine/DMF was injected into 50 mmol of Ala loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 23.91 g of a crude solid can be obtained by repeating a series of processes according to the amino acid sequence according to Table 1 and performing the cleavage step (Example 9). 3 g of the crude solid was purified through Prep LC and then lyophilized to obtain 0.67 g of a final solid.

(95) Example 95

400 ml of 20% piperidine/DMF was injected into 50 mmol of Val loaded in the same manner as in Example 8 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Val reaction part, and then 31.32 ml of DIC was injected and dehydrated by stirring for 4 hours at room temperature. 15.41 g of a crude solid can be obtained by repeating a series of processes according to the amino acid sequence according to Table 1 and performing the cleavage step (Example 9). 3 g of the crude solid was purified through Prep LC and then lyophilized to obtain 1.17 g of a final solid.

(96) Example 96

400 ml of 20% piperidine/DMF was injected into 50 mmol of Ala loaded in the same manner as in Example 4 and dehydrated by stirring for 10 minutes. This process was repeated twice. 450 ml of DMF was injected and dehydrated by stirring for 10 minutes. This process was repeated twice.

450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 22.60 g of a crude solid can be obtained by repeating a series of processes according to the amino acid sequence according to Table 1 and performing the cleavage step (Example 9). 5 g of the crude solid was purified through Prep LC and then lyophilized to obtain 1.27 g of a final solid.

(97) Example 97

400 ml of 20% piperidine/DMF was injected into 50 mmol of Ala loaded in the same manner as in Example 4 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 35.34 g of Fmoc-Leu-OH, 13.52 g of HOBt, and 900 ml of DMF were dissolved by stirring for 10 minutes. The dissolved solution was injected into the trityl-Ala reaction part, and then 31.32 ml of DIC was injected and dehydrated by stirring for 4 hours at room temperature. 19.39 g of a crude solid can be obtained by repeating a series of processes according to the amino acid sequence according to Table 1 and performing the cleavage step (Example 9). 3 g of the crude solid was purified through Prep LC and then lyophilized to obtain 1.08 g of a final solid.

(98) Example 98

400 ml of 20% piperidine/DMF was injected into 50 mmol of Leu loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, Fmoc-Leu-OH (35.34 g), 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 20.26 g of a crude solid can be obtained by repeating a series of processes according to the amino acid sequence according to Table 1 and performing the cleavage step (Example 9). 3 g of the crude solid was purified through Prep LC and then lyophilized to obtain 1.46 g of a final solid.

(99) Example 99

400 ml of 20% piperidine/DMF was injected into 50 mmol of Leu loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes.
This process was repeated three times. In the other reaction part, 33.93 g of Fmoc-Val-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 20.76 g of a crude solid can be obtained by repeating a series of processes according to the amino acid sequence according to Table 1 and performing the cleavage step (Example 9). 3 g of the crude solid was purified through Prep LC and then lyophilized to obtain 1.13 g of a final solid.

(100) Example 100

5 g of the crude solid obtained in Example 10 was injected, and then 240 mL of toluene was injected. The reaction part was heated to 110° C., and the reaction proceeded for 24 hours. After completion of the reaction, the solid was dehydrated by cooling to room temperature, and 4.4 g can be obtained. 4 g of the crude solid was purified through Prep LC and then lyophilized to obtain 1.15 g of a final solid.

(101) Example 101

4 g of the crude solid obtained in Example 11 was injected, and then 192 mL of toluene was injected. The reaction part was heated to 110° C., and the reaction proceeded for 24 hours. After completion of the reaction, the solid was dehydrated by cooling to room temperature, and 3.7 g can be obtained. 3 g of the crude solid was purified through Prep LC and then lyophilized to obtain 0.86 g of a final solid.

(102) Example 102

5 g of the crude solid obtained in Example 12 was injected, and then 240 mL of toluene was injected. The reaction part was heated to 110° C., and the reaction proceeded for 24 hours. After completion of the reaction, the solid was dehydrated by cooling to room temperature, and 3.9 g can be obtained. 3 g of the crude solid was purified through Prep LC and then lyophilized to obtain 1.15 g of a final solid.

(103) Example 103

4 g of the crude solid obtained in Example 15 was injected, and then 192 mL of toluene was injected. The reaction part was heated to 110° C., and the reaction proceeded for 24 hours. After completion of the reaction, the solid was dehydrated by cooling to room temperature, and 3.7 g can be obtained. 3.5 g of the crude solid was purified through Prep LC and then lyophilized to obtain 1.41 g of a final solid.

(104) Example 104

5 g of the crude solid obtained in Example 16 was injected, and then 240 mL of toluene was injected. The reaction part was heated to 110° C., and the reaction proceeded for 24 hours. After completion of the reaction, the solid was dehydrated by cooling to room temperature, and 4.9 g can be obtained. 4 g of the crude solid was purified through Prep LC and then lyophilized to obtain 2.14 g of a final solid.

(105) Example 105

4 g of the crude solid obtained in Example 19 was injected, and then 192 mL of toluene was injected. The reaction part was heated to 110° C., and the reaction proceeded for 24 hours. After completion of the reaction, the solid was dehydrated by cooling to room temperature, and 3.7 g can be obtained. 3.5 g of the crude solid was purified through Prep LC and then lyophilized to obtain 1.49 g of a final solid.

(106) Example 106

1 g of the crude solid obtained in Example 10 was injected, and then 4 mL of IPA (isopropyl alcohol) was injected. 0.62 mL of $H_2SO_4$ was added and stirred under reflux to confirm the completion of the reaction by HPLC. It was dehydrated by cooling to room temperature, and 0.95 g of a crude solid can be obtained. 0.5 g of the crude solid was purified through Prep LC and then lyophilized to obtain 0.14 g of a final solid.

(107) Example 107

3 g of the crude solid obtained in Example 11 was injected, and then 12 mL of IPA was injected. 1.86 mL of $H_2SO_4$ was added and stirred under reflux to confirm the completion of the reaction by HPLC. It was dehydrated by cooling to room temperature, and 2.1 g of a crude solid can be obtained. 2 g of the crude solid was purified through Prep LC and then lyophilized to obtain 0.57 g of a final solid.

(108) Example 108

4 g of the crude solid obtained in Example 12 was injected, and then 16 mL of IPA was injected. 2.48 mL of $H_2SO_4$ was added and stirred under reflux to confirm the completion of the reaction by HPLC. It was dehydrated by cooling to room temperature, and 3.0 g of a crude solid can be obtained. 2 g of the crude solid was purified through Prep LC and then lyophilized to obtain 0.62 g of a final solid.

(109) Example 109

1 g of the crude solid obtained in Example 100 was injected, and then 4 mL of IPA was injected. 0.62 mL of $H_2SO_4$ was added and stirred under reflux to confirm the completion of the reaction by HPLC. It was dehydrated by cooling to room temperature, and 0.72 g of a crude solid can be obtained. 0.5 g of the crude solid was purified through Prep LC and then lyophilized to obtain 0.11 g of a final solid.

(110) Example 110

1 g of the crude solid obtained in Example 100 was injected, and then 4 mL of IPA was injected. 0.62 mL of $H_2SO_4$ was added and stirred under reflux to confirm the completion of the reaction by HPLC. It was dehydrated by cooling to room temperature, and 0.52 g of a crude solid can be obtained. 0.5 g of the crude solid was purified through Prep LC and then lyophilized to obtain 0.08 g of a final solid.

(111) Example 111

1 g of the crude solid obtained in Example 101 was injected, and then 4 mL of IPA was injected. 0.62 mL of $H_2SO_4$ was added and stirred under reflux to confirm the completion of the reaction by HPLC. It was dehydrated by cooling to room temperature, and 0.59 g of a crude solid can be obtained. 0.5 g of the crude solid was purified through Prep LC and then lyophilized to obtain 0.14 g of a final solid.

(112) Example 112

1 g of the crude solid obtained in Example 101 was injected, and then 4 mL of IPA was injected. 0.62 mL of $H_2SO_4$ was added and stirred under reflux to confirm the completion of the reaction by HPLC. It was dehydrated by cooling to room temperature, and 0.64 g of a crude solid can be obtained. 0.5 g of the crude solid was purified through Prep LC and then lyophilized to obtain 0.12 g of a final solid.

(113) Example 113

1 g of the crude solid obtained in Example 102 was injected, and then 4 mL of IPA was injected. 0.62 mL of $H_2SO_4$ was added and stirred under reflux to confirm the completion of the reaction by HPLC. It was dehydrated by cooling to room temperature, and 0.39 g of a crude solid can be obtained. 0.3 g of the crude solid was purified through Prep LC and then lyophilized to obtain 0.07 g of a final solid.

(114) Example 114

1 g of the crude solid obtained in Example 102 was injected, and then 4 mL of IPA was injected. 0.62 mL of $H_2SO_4$ was added and stirred under reflux to confirm the completion of the reaction by HPLC. It was dehydrated by cooling to room temperature, and 0.79 g of a crude solid can be obtained. 0.5 g of the crude solid was purified through Prep LC and then lyophilized to obtain 0.20 g of a final solid.

(115) Example 115

1 g of the crude solid obtained in Example 10 was injected, and then 4 mL of IPA was injected. 0.62 mL of $H_2SO_4$ was added and stirred under reflux to confirm the completion of the reaction by HPLC. It was dehydrated by cooling to room temperature, and 0.48 g of a crude solid can be obtained. 0.3 g of the crude solid was purified through Prep LC and then lyophilized to obtain 0.08 g of a final solid.

(116) Example 116

1 g of the crude solid obtained in Example 11 was injected, and then 4 mL of IPA was injected. 0.62 mL of $H_2SO_4$ was added and stirred under reflux to confirm the completion of the reaction by HPLC. It was dehydrated by cooling to room temperature, and 0.81 g of a crude solid can be obtained. 0.5 g of the crude solid was purified through Prep LC and then lyophilized to obtain 0.10 g of a final solid.

(117) Example 117

1 g of the crude solid obtained in Example 12 was injected, and then 4 mL of IPA was injected. 0.62 mL of $H_2SO_4$ was added and stirred under reflux to confirm the completion of the reaction by HPLC. It was dehydrated by cooling to room temperature, and 0.69 g of a crude solid can be obtained. 0.5 g of the crude solid was purified through Prep LC and then lyophilized to obtain 0.11 g of a final solid.

(118) Example 118

1 g of the crude solid obtained in Example 30 was injected, and then 4 mL of IPA was injected. $H_2SO_4$ (0.62 mL) was added and stirred under reflux to confirm the completion of the reaction by HPLC. It was dehydrated by cooling to room temperature, and 0.48 g of a crude solid can be obtained. 0.4 g of the crude solid was purified through Prep LC and then lyophilized to obtain 0.27 g of a final solid.

(119) Example 119

400 ml of 20% piperidine/DMF was injected into 50 mmol of Val loaded in the same manner as in Example 8 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 31.13 g of Fmoc-Ala-OH, 13.52 g of HOBt, and 900 ml of DMF were dissolved by stirring for 10 minutes. The dissolved solution was injected into the trityl-Val reaction part, and then 31.32 ml of DIC was injected and dehydrated by stirring for 4 hours at room temperature. 11.94 g of a crude solid can be obtained by repeating a series of processes according to the amino acid sequence according to Table 1 and performing the cleavage step (Example 9). 3 g of the crude solid was purified through Prep LC and then lyophilized to obtain 1.07 g of a final solid.

(120) Example 120

400 ml of 20% piperidine/DMF was injected into 50 mmol of Leu loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 31.13 g of Fmoc-Ala-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 13.57 g of a crude solid can be obtained by repeating a series of processes according to the amino acid sequence according to Table 1 and performing the cleavage step (Example 9). 3 g of the crude solid was purified through Prep LC and then lyophilized to obtain 1.44 g of a final solid.

(121) Example 121

400 ml of 20% piperidine/DMF was injected into 50 mmol of Leu loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 31.13 g of Fmoc-Leu-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 12.91 g of a crude solid can be obtained by repeating a series of processes according to the amino acid sequence according to Table 1 and performing the cleavage step (Example 9). 3 g of the crude solid was purified through Prep LC and then lyophilized to obtain 0.89 g of a final solid.

(122) Example 122

400 ml of 20% piperidine/DMF was injected into 50 mmol of Leu loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, Fmoc-Gly-OH (29.73 g), 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 11.82 g of a crude solid can be obtained by repeating a series of processes according to the amino acid sequence according to Table 1 and performing the cleavage step (Example 9). 3 g of the crude solid was purified through Prep LC and then lyophilized to obtain 1.26 g of a final solid.

(123) Example 123

400 ml of 20% piperidine/DMF was injected into 50 mmol of Leu loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 31.13 g of Fmoc-Leu-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 12.44 g of a crude solid can be obtained by repeating a series of processes according to the amino acid sequence according to Table 1 and performing the cleavage step (Example 9). 3 g of the crude solid was purified through Prep LC and then lyophilized to obtain 1.08 g of a final solid.

(124) Example 124

400 ml of 20% piperidine/DMF was injected into 50 mmol of Leu loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 33.93 g of Fmoc-Val-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 10.47 g of a crude solid can be obtained by repeating a series of processes according to the amino acid sequence according to Table 1 and performing the cleavage step (Example 9). 3 g of the crude solid was purified through Prep LC and then lyophilized to obtain 1.20 g of a final solid.

(125) Example 125

400 ml of 20% piperidine/DMF was injected into 50 mmol of Leu loaded in the same manner as in Example 5 and dehydrated by stirring for 10 minutes. This process was repeated twice. 450 ml of DMF was injected and dehydrated by stirring for 10 minutes. This process was repeated twice. 450 ml of MC was injected and then dehydrated by stirring for 10 minutes. This process was repeated three times. In the other reaction part, 41.15 g of Fmoc-D Asp (OtBu)-OH, 13.52 g of HOBt, and 900 ml of DMF were dissolved by stirring for 10 minutes. The dissolved solution was injected into the trityl-Leu reaction part, and then 31.32 ml of DIC was injected and dehydrated by stirring for 4 hours at room temperature. 8.41 g of a crude solid can be obtained by repeating a series of processes according to the amino acid sequence according to Table 1 and performing the cleavage step (Example 9). 4 g of the crude solid was purified through Prep LC and then lyophilized to obtain 2.06 g of a final solid.

Experimental Example 1: Evaluation of Dissolution Stability

For each of the peptides of Examples 10 to 125 above, the content change was confirmed when stored for 7 days at a concentration of 1 mg/1 ml in a dissolved state at a storage condition of 40° C. and RH 75%. The results are shown in Table 2 below.

TABLE 2

| No. | Example | Initial content (%) | Day 1 content (%) | Day 3 content (%) | Day 7 content (%) |
|---|---|---|---|---|---|
| 1 | Example 10 | 98.76 | NT | 86.65 | 78.68 |
| 2 | Example 11 | 98.96 | 91.37 | 81.21 | 64.19 |
| 3 | Example 12 | 95.31 | 89.90 | 79.04 | 58.75 |
| 4 | Example 13 | 98.51 | 98.39 | 98.04 | 97.64 |
| 5 | Example 14 | 97.13 | 96.58 | 96.07 | 95.55 |
| 6 | Example 15 | 91.84 | 91.06 | 81.63 | 70.56 |
| 7 | Example 16 | 80.41 | 47.33 | 16.48 | 10.78 |
| 8 | Example 17 | 96.55 | 96.53 | 96.69 | 96.27 |
| 9 | Example 18 | 82.99 | 53.91 | 36.72 | 13.41 |
| 10 | Example 19 | 95.90 | 89.94 | 79.26 | 71.50 |
| 11 | Example 20 | 99.35 | 98.77 | 99.69 | 99.66 |
| 12 | Example 21 | 84.05 | 79.91 | 77.37 | 69.10 |
| 13 | Example 22 | 88.14 | 85.47 | 83.10 | 82.67 |
| 14 | Example 23 | 96.40 | 95.25 | 94.22 | 90.56 |
| 15 | Example 24 | 96.57 | 96.14 | 95.71 | 95.13 |
| 16 | Example 25 | 89.14 | 85.76 | 81.09 | 77.40 |
| 17 | Example 26 | 92.17 | 89.41 | 87.99 | 85.43 |
| 18 | Example 27 | 98.24 | 98.16 | 98.15 | 98.16 |
| 19 | Example 28 | 99.14 | 98.50 | 97.37 | 96.19 |
| 20 | Example 29 | 95.19 | 93.74 | 92.16 | 90.82 |
| 21 | Example 30 | 96.44 | 95.61 | 94.27 | 91.57 |
| 22 | Example 31 | 91.42 | 85.08 | 78.24 | 60.99 |
| 23 | Example 32 | 98.05 | 96.81 | 93.57 | 90.50 |
| 24 | Example 33 | 99.46 | 96.68 | 89.94 | 86.76 |
| 25 | Example 34 | 97.18 | 97.05 | 95.50 | 91.59 |
| 26 | Example 35 | 98.51 | 97.50 | 95.78 | 93.68 |
| 27 | Example 36 | 95.40 | 94.13 | 90.58 | 85.95 |
| 28 | Example 37 | 98.59 | 98.64 | 97.76 | 93.55 |
| 29 | Example 38 | 97.06 | 92.19 | 88.19 | 85.93 |
| 30 | Example 39 | 93.03 | 91.76 | 88.16 | 85.50 |
| 31 | Example 40 | 89.95 | 81.96 | 70.04 | 51.11 |
| 32 | Example 41 | 96.95 | 93.20 | 91.07 | 85.34 |
| 33 | Example 42 | 71.84 | 65.09 | 52.07 | 37.87 |
| 34 | Example 43 | 99.47 | 86.75 | 65.09 | 48.43 |
| 35 | Example 44 | 99.11 | 89.07 | 78.54 | 56.03 |
| 36 | Example 45 | 94.45 | 86.74 | 69.07 | 56.03 |
| 37 | Example 46 | 93.29 | 87.32 | 81.37 | 62.32 |
| 38 | Example 47 | 94.90 | 84.03 | 75.02 | 51.42 |
| 39 | Example 48 | 92.71 | 84.40 | 76.53 | 53.82 |
| 40 | Example 49 | 94.35 | 86.53 | 79.49 | 60.01 |
| 41 | Example 50 | 96.67 | 89.44 | 80.15 | 56.11 |
| 42 | Example 51 | 92.07 | 83.35 | 72.55 | 49.31 |
| 43 | Example 52 | 96.55 | 86.35 | 74.65 | 54.51 |
| 44 | Example 53 | 94.88 | 87.14 | 76.02 | 62.88 |
| 45 | Example 54 | 95.42 | 83.66 | 73.59 | 62.48 |
| 46 | Example 55 | 97.82 | 94.34 | 90.29 | 81.00 |
| 47 | Example 56 | 90.94 | 84.52 | 79.98 | 51.41 |
| 48 | Example 57 | 91.95 | 75.20 | 71.82 | 53.88 |
| 49 | Example 58 | 98.03 | 98.01 | 97.85 | 97.56 |
| 50 | Example 59 | 98.78 | 98.78 | 98.76 | 98.75 |
| 51 | Example 60 | 97.21 | 92.72 | 88.92 | 58.84 |
| 52 | Example 61 | 92.80 | 87.65 | 83.70 | 56.36 |
| 53 | Example 62 | 97.24 | 92.60 | 84.99 | 70.41 |

TABLE 2-continued

| No. | Example | Initial content (%) | Day 1 content (%) | Day 3 content (%) | Day 7 content (%) |
|---|---|---|---|---|---|
| 54 | Example 63 | 94.37 | 88.74 | 81.41 | 64.20 |
| 55 | Example 64 | 96.19 | 91.62 | 86.18 | 48.37 |
| 56 | Example 65 | 95.64 | 92.97 | 86.96 | 75.40 |
| 57 | Example 66 | 96.42 | 89.15 | 79.64 | 60.49 |
| 58 | Example 67 | 98.36 | 99.14 | 98.75 | 98.07 |
| 59 | Example 68 | 98.71 | 98.25 | 97.51 | 96.93 |
| 60 | Example 69 | 97.12 | 96.94 | 96.32 | 95.69 |
| 61 | Example 70 | 92.41 | 90.84 | 88.52 | 85.77 |
| 62 | Example 71 | 95.21 | 93.07 | 88.76 | 82.04 |
| 63 | Example 72 | 97.08 | 95.91 | 90.84 | 82.07 |
| 64 | Example 73 | 92.11 | 89.07 | 82.64 | 75.49 |
| 65 | Example 74 | 98.01 | 92.95 | 85.57 | 79.66 |
| 66 | Example 75 | 98.53 | 91.10 | 75.24 | 61.06 |
| 67 | Example 76 | 95.07 | 90.01 | 82.34 | 69.13 |
| 68 | Example 77 | 92.01 | 86.66 | 80.88 | 69.44 |
| 69 | Example 78 | 97.41 | 92.18 | 85.14 | 74.01 |
| 70 | Example 79 | 94.36 | 97.87 | 81.04 | 76.89 |
| 71 | Example 80 | 98.44 | 97.18 | 97.13 | 97.07 |
| 72 | Example 81 | 95.87 | 93.01 | 92.10 | 89.51 |
| 73 | Example 82 | 97.54 | 92.51 | 85.09 | 79.04 |
| 74 | Example 83 | 95.42 | 95.35 | 94.70 | 94.00 |
| 75 | Example 84 | 97.78 | 97.91 | 97.29 | 96.49 |
| 76 | Example 85 | 92.62 | 92.08 | 88.07 | 75.04 |
| 77 | Example 86 | 98.16 | 97.40 | 97.77 | 97.55 |
| 78 | Example 87 | 99.14 | 98.07 | 96.57 | 94.38 |
| 79 | Example 88 | 99.23 | 98.94 | 98.07 | 97.37 |
| 80 | Example 89 | 99.57 | 99.07 | 98.81 | 98.43 |
| 81 | Example 90 | 98.68 | 98.58 | 98.32 | 97.94 |
| 82 | Example 91 | 99.08 | 99.10 | 98.74 | 98.68 |
| 83 | Example 92 | 96.92 | 97.05 | 96.92 | 96.56 |
| 84 | Example 93 | 98.39 | 98.35 | 98.05 | 97.79 |
| 85 | Example 94 | 98.59 | 98.77 | 98.43 | 98.15 |
| 86 | Example 95 | 98.64 | 98.62 | 98.10 | 97.78 |
| 87 | Example 96 | 98.07 | 97.14 | 96.64 | 96.02 |
| 88 | Example 97 | 97.08 | 95.01 | 94.31 | 94.08 |
| 89 | Example 98 | 99.03 | 99.07 | 98.86 | 98.74 |
| 90 | Example 99 | 99.45 | 99.44 | 99.28 | 99.15 |
| 91 | Example 100 | 97.58 | 93.43 | 85.30 | 74.12 |
| 92 | Example 101 | 88.72 | 86.61 | 86.38 | 83.40 |
| 93 | Example 102 | 92.47 | 90.18 | 85.07 | 81.09 |
| 94 | Example 103 | 97.09 | 97.20 | 96.90 | 94.88 |
| 95 | Example 104 | 94.22 | 96.52 | 93.78 | 93.01 |
| 96 | Example 105 | 89.11 | 54.80 | 41.83 | 31.24 |
| 97 | Example 106 | 89.54 | 81.47 | 75.61 | 68.25 |
| 98 | Example 107 | 87.55 | 76.34 | 65.41 | 58.41 |
| 99 | Example 108 | 79.49 | 67.07 | 62.81 | 59.24 |
| 100 | Example 109 | 85.34 | 79.15 | 69.45 | 59.07 |
| 101 | Example 110 | 98.00 | 85.18 | 72.44 | 91.84 |
| 102 | Example 111 | 97.48 | 90.71 | 82.07 | 69.37 |
| 103 | Example 112 | 95.34 | 92.78 | 86.07 | 80.91 |
| 104 | Example 113 | 93.25 | 92.40 | 85.41 | 72.35 |
| 105 | Example 114 | 84.91 | 75.01 | 56.84 | 32.74 |
| 106 | Example 115 | 92.71 | 88.57 | 82.00 | 71.64 |
| 107 | Example 116 | 88.64 | 85.82 | 84.31 | 83.50 |
| 108 | Example 117 | 94.77 | 90.61 | 85.37 | 76.88 |
| 109 | Example 118 | 96.15 | 92.71 | 85.67 | 79.33 |
| 114 | Example 119 | 96.39 | 96.33 | 96.18 | 95.89 |
| 115 | Example 120 | 99.07 | 98.87 | 98.73 | 98.44 |
| 116 | Example 121 | 99.39 | 99.29 | 99.13 | 99.22 |
| 117 | Example 122 | 98.82 | 98.66 | 98.56 | 98.27 |
| 118 | Example 123 | 99.26 | 99.14 | 98.98 | 98.86 |
| 119 | Example 124 | 99.40 | 99.22 | 99.11 | 98.97 |
| 120 | Example 125 | 98.28 | 97.15 | 95.07 | 88.48 |

Referring to Table 2 above, it can be seen that in most examples, the content was maintained at 50% or more after 7 days, and the stability was very good.

Experimental Example 2: In Vitro Evaluation of Anti-Inflammatory Efficacy Using Mouse Macrophage An anti-inflammatory efficacy was evaluated for representative examples of the above examples. Specifically, in order to confirm whether Examples 10, 32, 41, 55, 59 and 91, which are representative examples of 5 amino acid residues, Examples 11 and 30, which are representative examples of 6 amino acid residues, Example 86, which is a representative example of 7 amino acid residues, and Examples 103 and 104, which are representative examples of 8 amino acid residues, have an anti-inflammatory effect, a change in the secretion amount of inflammatory cytokines was confirmed by enzyme-linked immunosorbent assay (ELISA) using Raw 264.7 cells, which are macrophage (monocyte) cell lines.

Specifically, the Examples were diluted in Raw264.7 cells (Korean Cell Line Bank, 40071) at a concentration of 10 nM, 100 nM, 1 µM, and 10 µM, respectively, and pretreated for 1 hour, and then LPS (Sigma, L6529) at a concentration of 1 µg/ml was added to induce an inflammatory response. After 24 hours of induction, the cell culture supernatant was collected and analyzed. Enzyme-linked immunosorbent assay was performed using Mouse IL-6 Quantikine ELISA Kit (R&D systems, M6000B), TNF-alpha Quantikine ELISA Kit (R&D systems, MTA00B), Mouse IL-1 beta/IL-1F2 Quantikine ELISA Kit (R&D systems, MLB00C) in accordance with the manufacturer's manual.

Figure 1C:
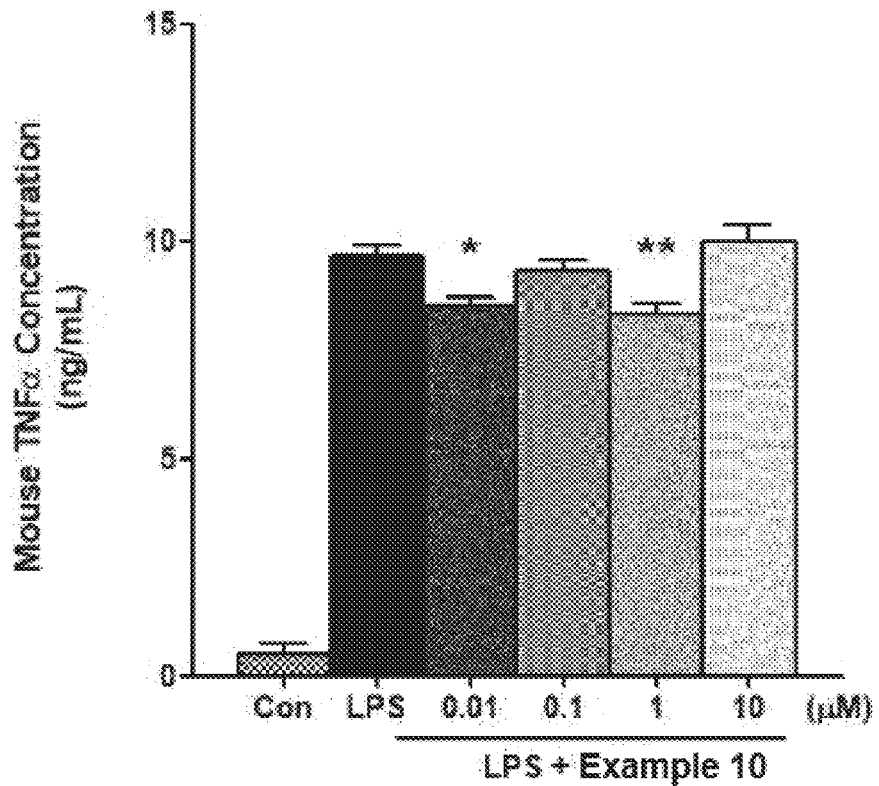

As a result, referring to FIG. 1a, Example 10, which is a 5 mer, significantly reduced the IL-1β level increased by LPS at a concentration of 100 nM and 1 µM, and referring to FIG. 1c, significantly reduced the TNFα level increased by LPS at a concentration of 10 nM and 1 µM.

Figure 2A:
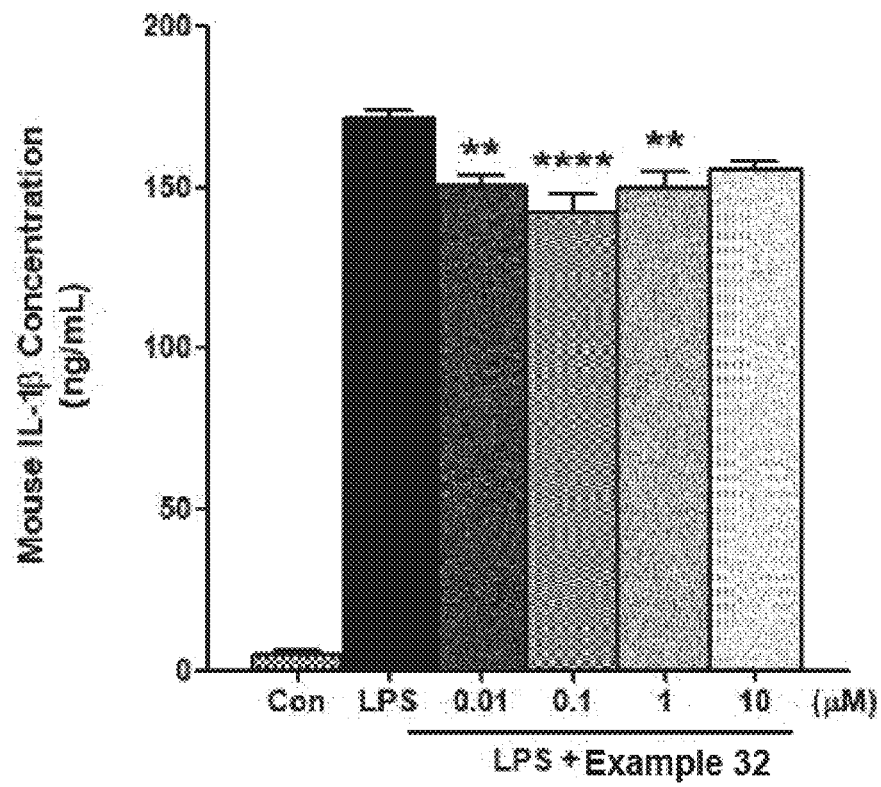
FIGS. 2a, 2b and 2c show results of measuring the expression levels of IL-1β, IL-6 and TNFα according to the treatment of Example 32 in LPS-stimulated macrophages, respectively.
Figure 2B:
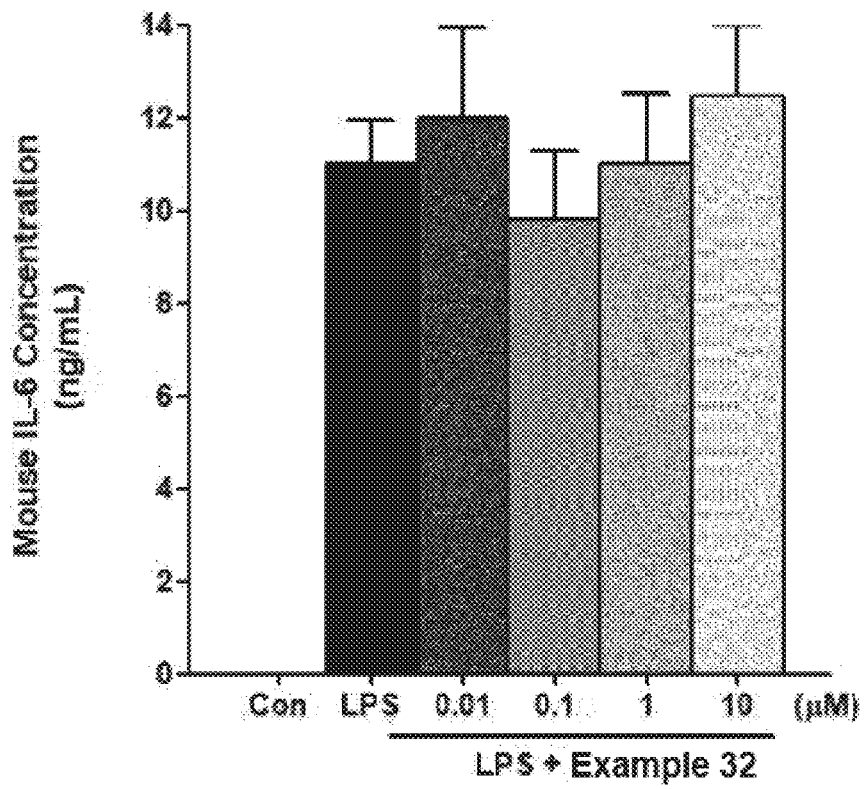
Figure 2C:
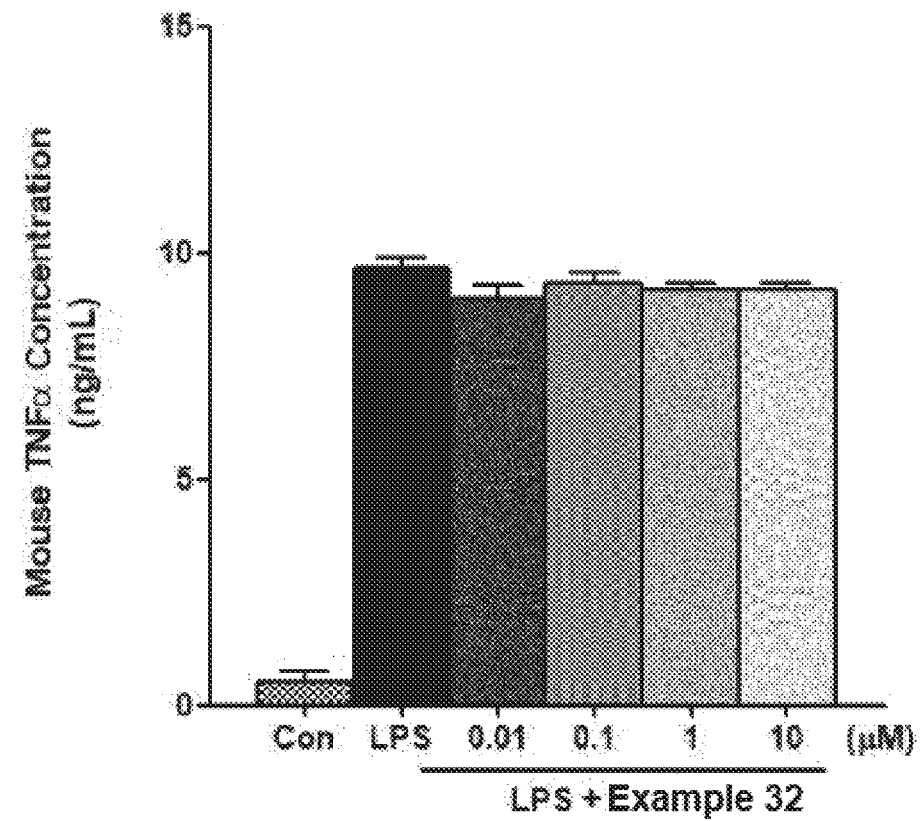

Referring to FIG. 2a, Example 32, which is a 5 mer, significantly reduced the IL-1β level increased by LPS at a concentration of 10 nM, 100 nM and 1 µM.

Figure 3A:
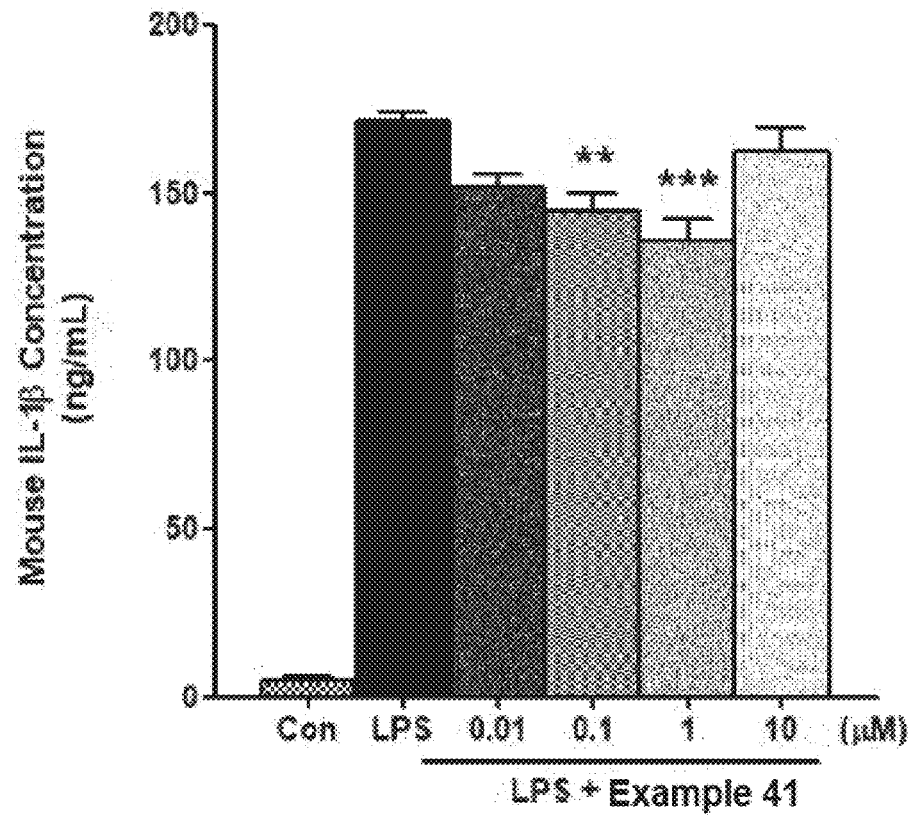
FIGS. 3a, 3b and 3c show results of measuring the expression levels of IL-1β, IL-6 and TNFα according to the treatment of Example 41 in LPS-stimulated macrophages, respectively.
Figure 3B:
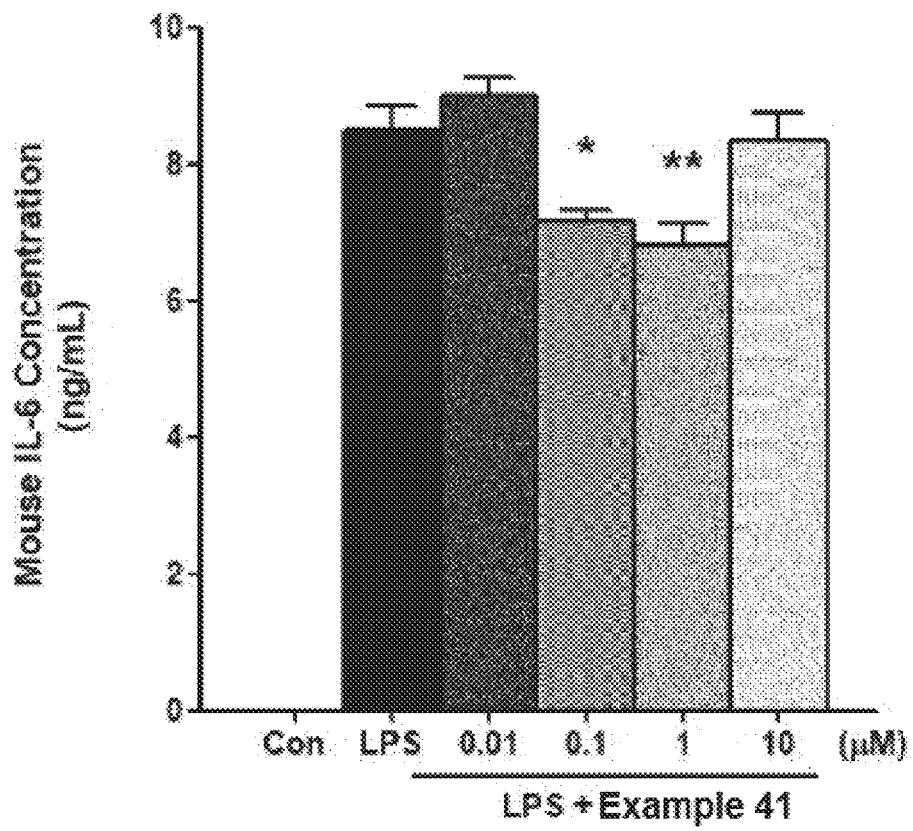
Figure 3C:
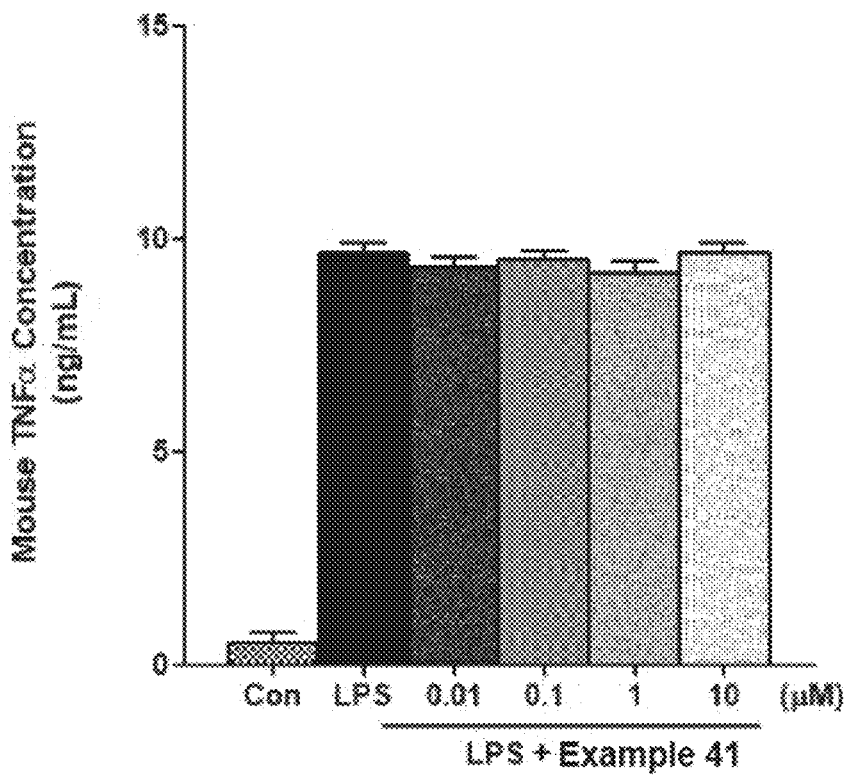

Referring to FIG. 3a, Example 41, which is a 5 mer, significantly reduced the IL-1β level and IL-6 level increased by LPS at a concentration of 100 nM and 1 µM, respectively.

Figure 4A:
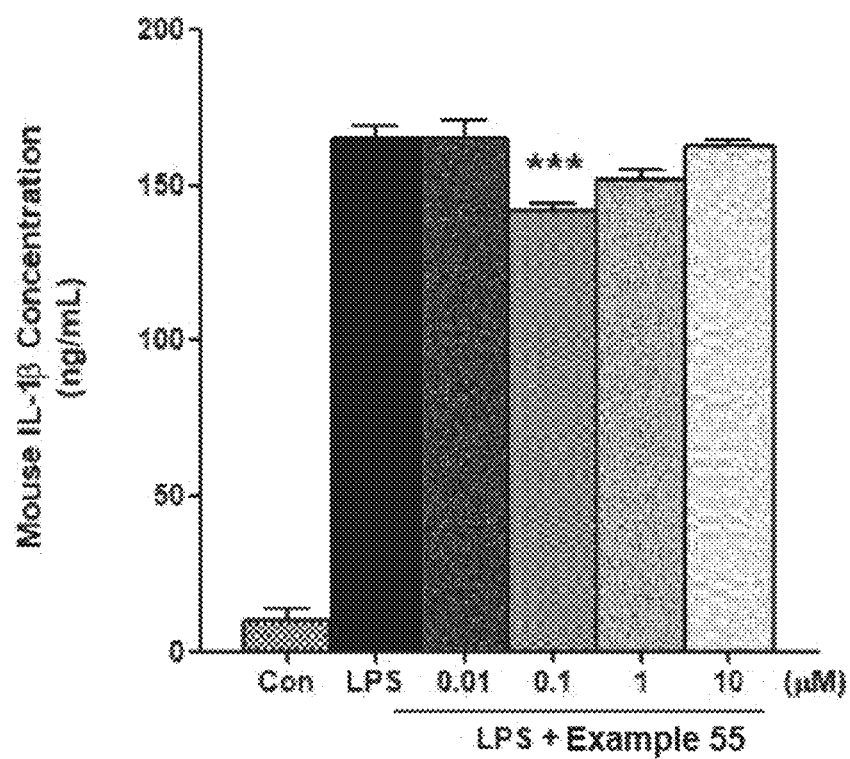
FIGS. 4a, 4b and 4c show results of measuring the expression levels of IL-1β, IL-6 and TNFα according to the treatment of Example 55 in LPS-stimulated macrophages, respectively.
Figure 4B:
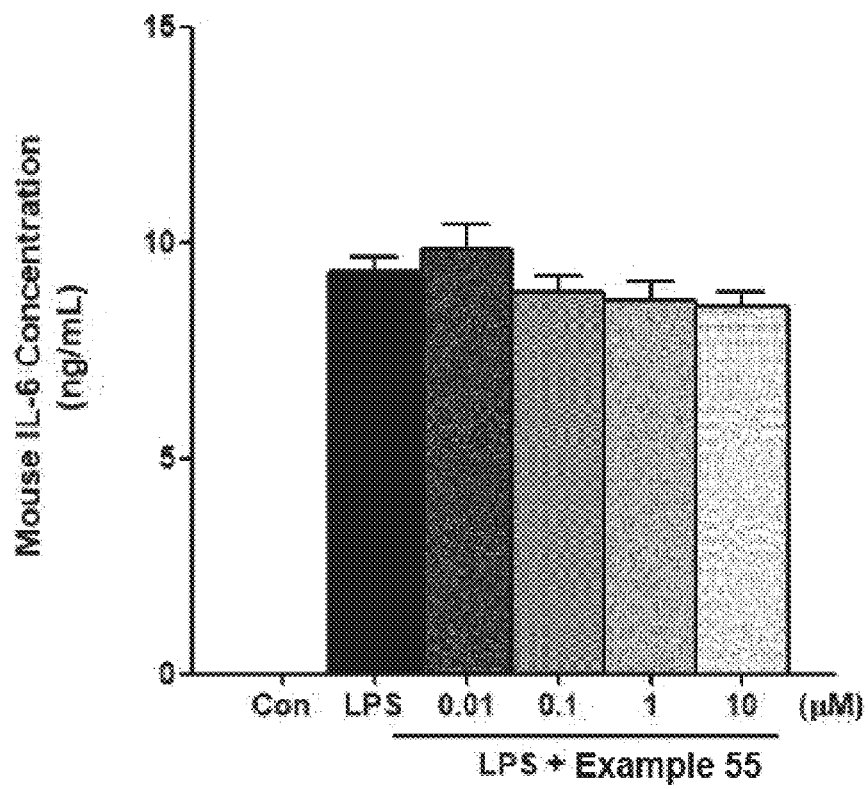
Figure 4C:
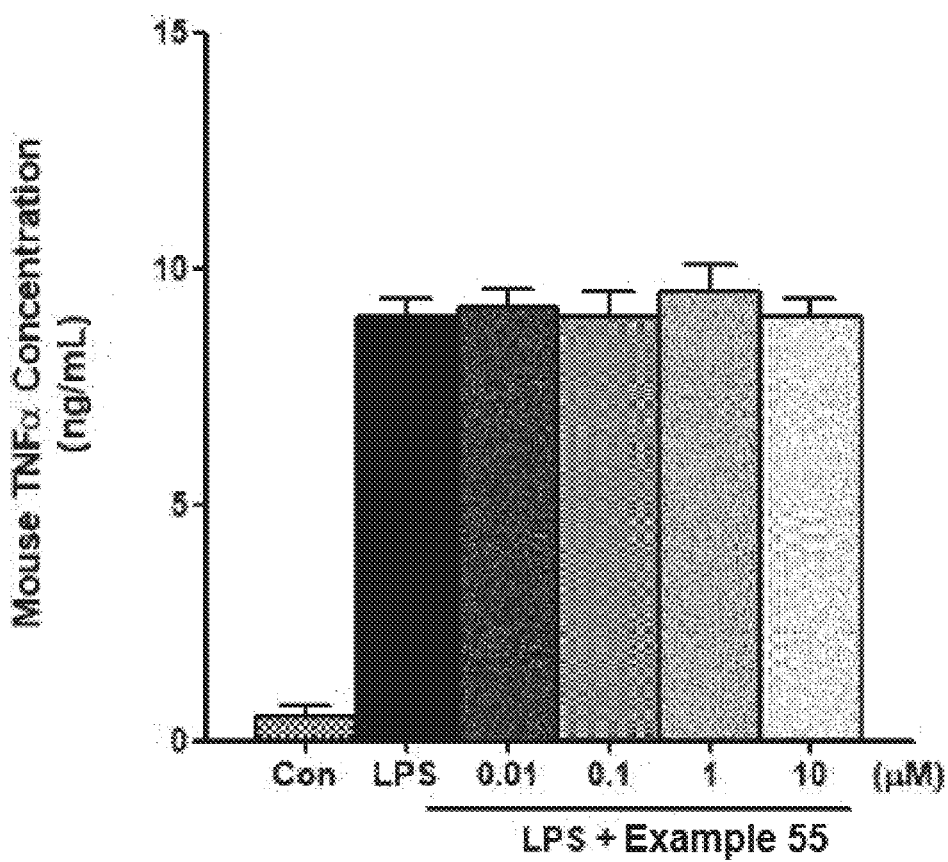
Figure 5A:
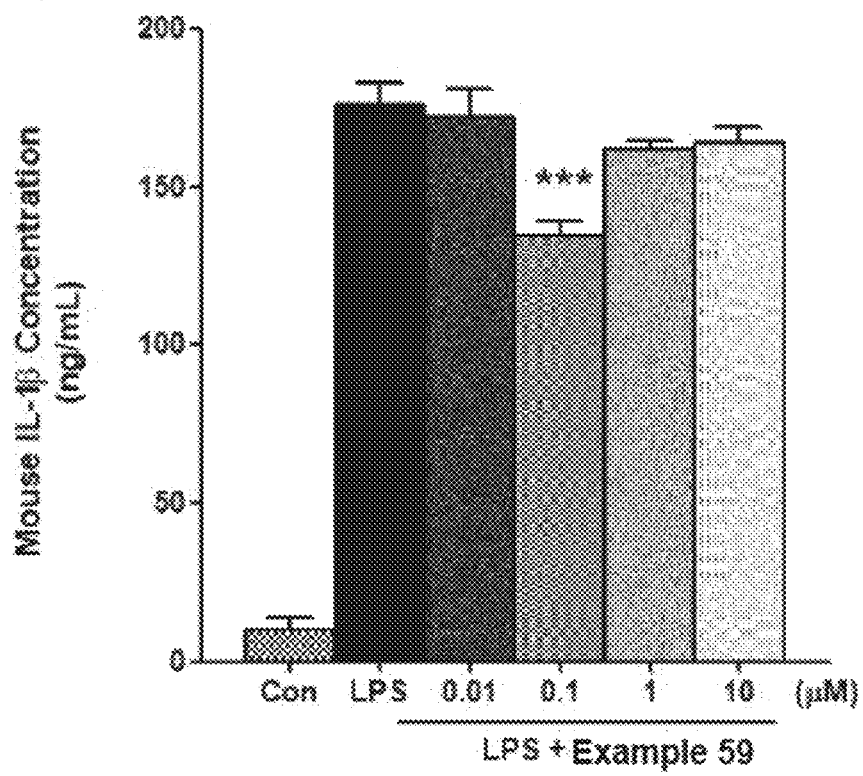
FIGS. 5a, 5b and 5c show results of measuring the expression levels of IL-1β, IL-6 and TNFα according to the treatment of Example 59 in LPS-stimulated macrophages, respectively.
Figure 5B:
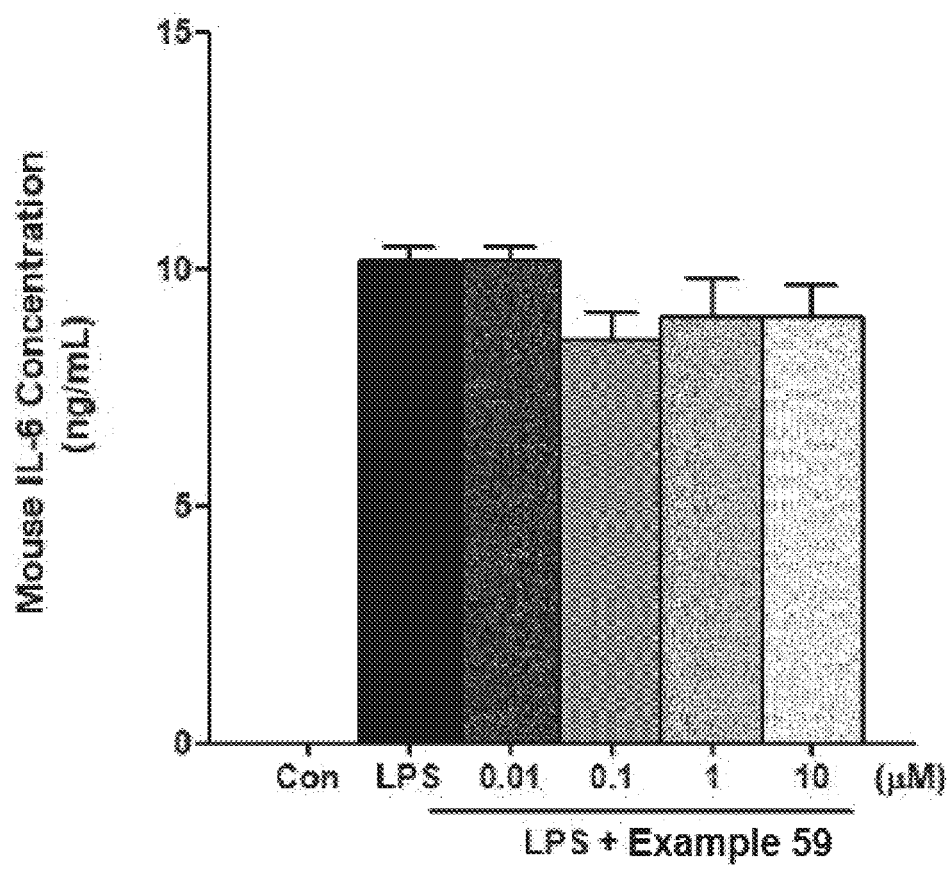
Figure 5C:
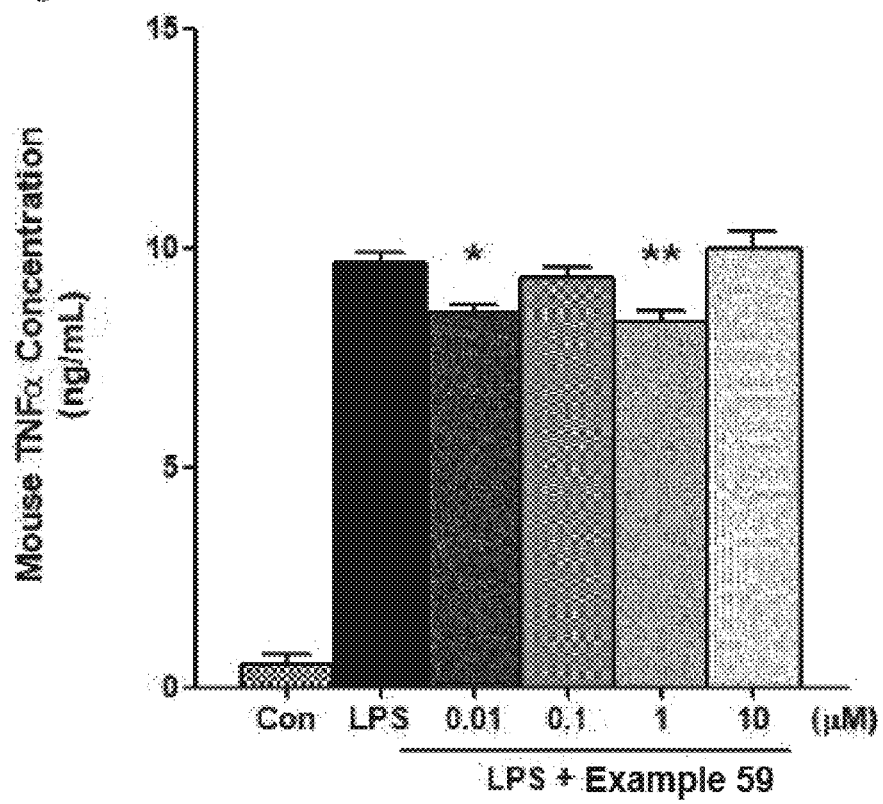

Referring to FIGS. 4a and 5a, Examples 55 and 59, which are 5 mer, significantly reduced the IL-1β level increased by LPS at a concentration of 100 nM.

Figure 6A:
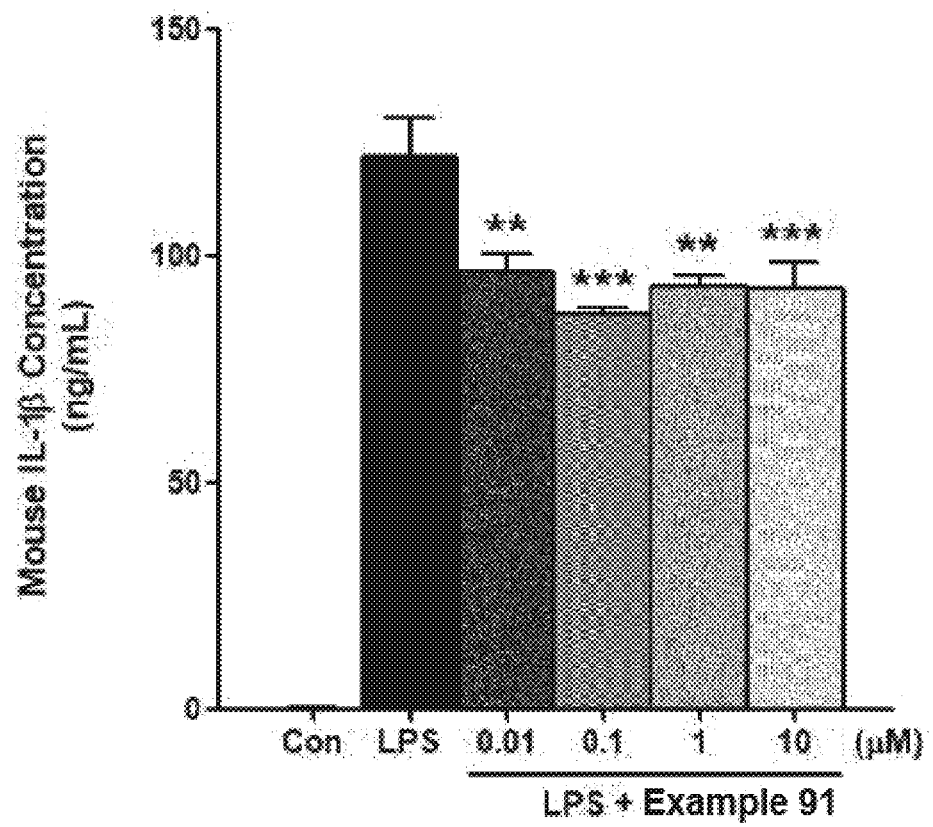
FIGS. 6a, 6b and 6c show results of measuring the expression levels of IL-1β, IL-6 and TNFα according to the treatment of Example 91 in LPS-stimulated macrophages, respectively.
Figure 6B:
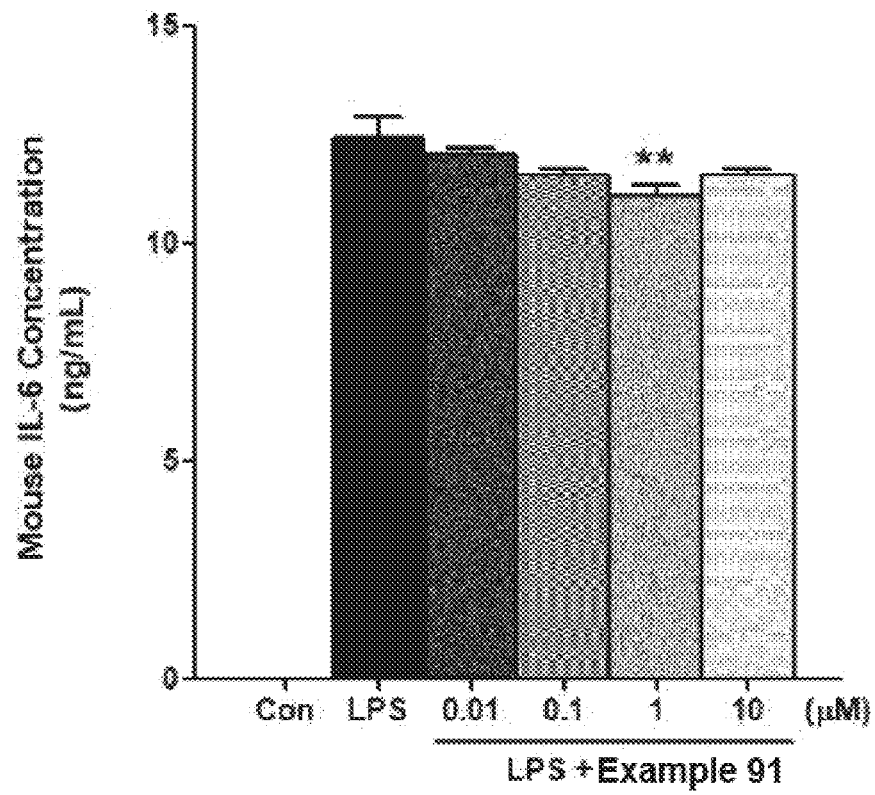
Figure 6C:
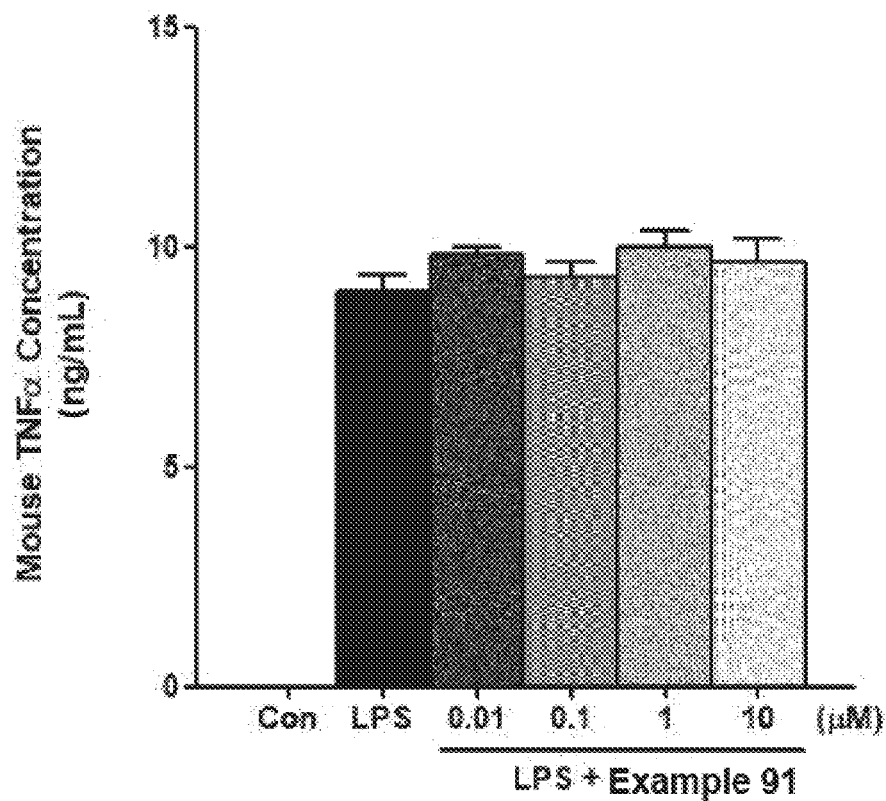

Referring to FIGS. 6a and 6b, Example 91, which is a 5 mer, reduced the IL-1β level increased by LPS at all concentrations (10 nM, 100 nM, 1 µM, and 10 µM), and significantly reduced only the IL-6 level increased by LPS at a concentration of 1 µM.

Figure 7A:
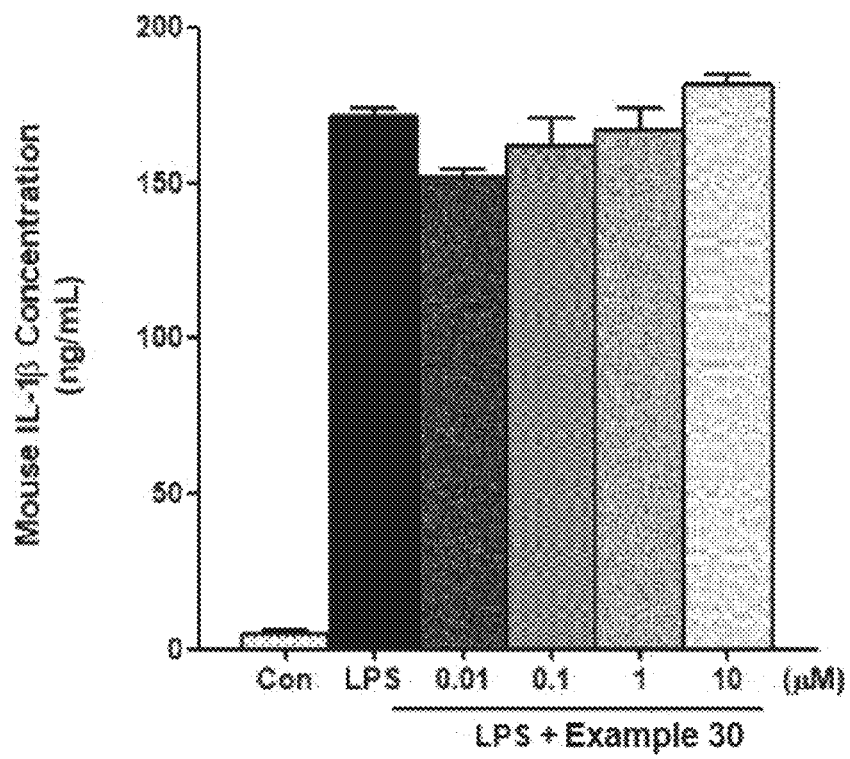
FIGS. 7a, 7b and 7c show results of measuring the expression levels of IL-1β, IL-6 and TNFα according to the treatment of Example 30 in LPS-stimulated macrophages, respectively.
Figure 7B:
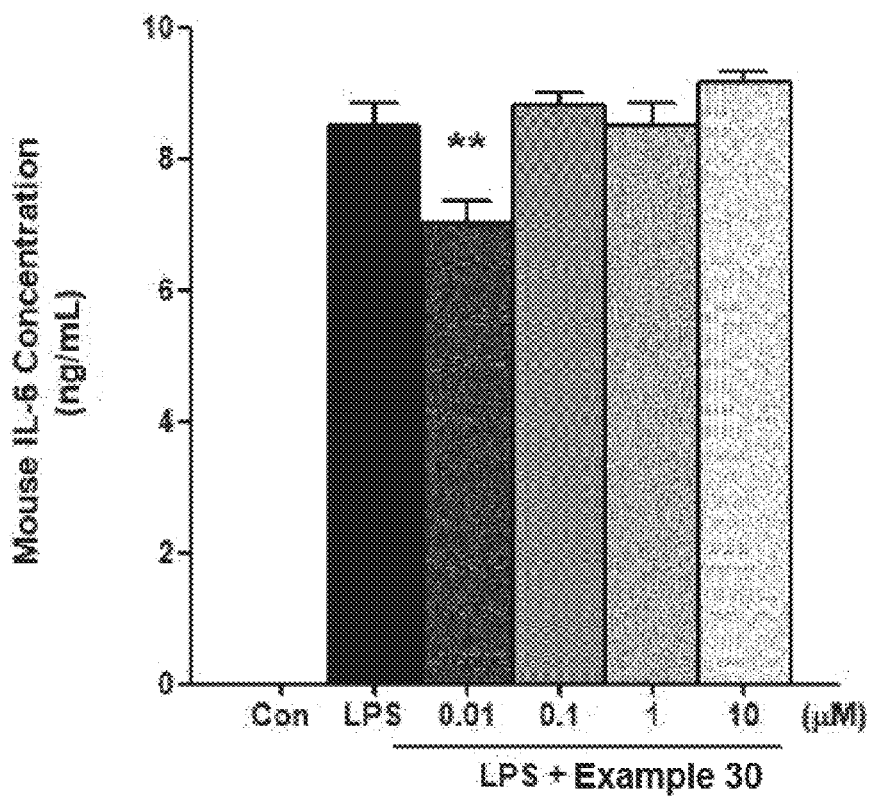
Figure 7C:
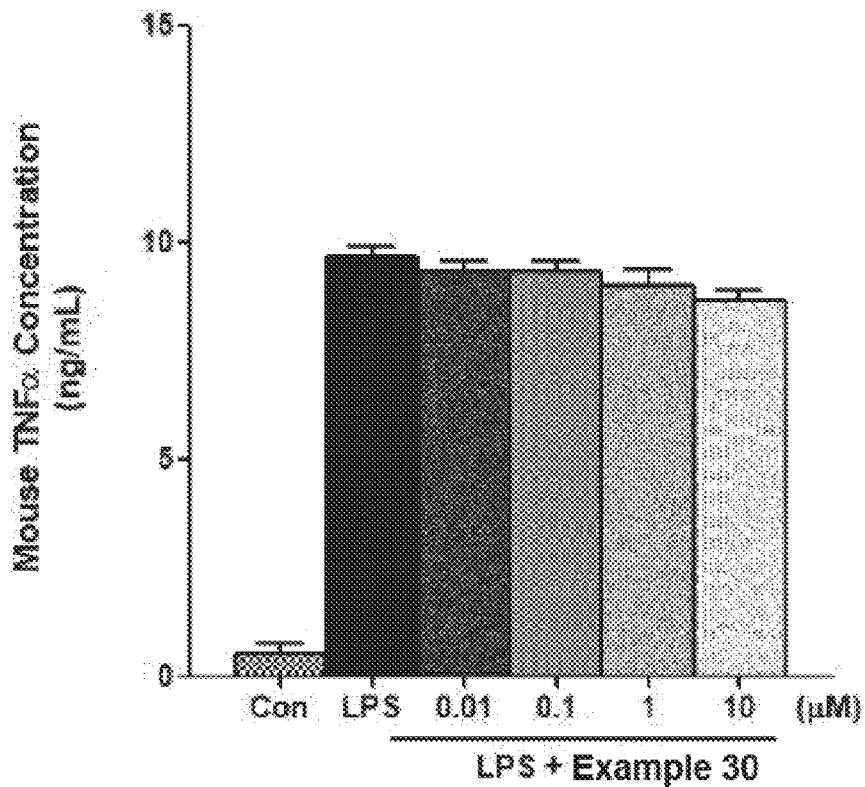

Referring to FIG. 7b, Example 30, which is a 6 mer, significantly reduced the IL-6 level increased by LPS at a concentration of 10 nM.

Figure 8A:
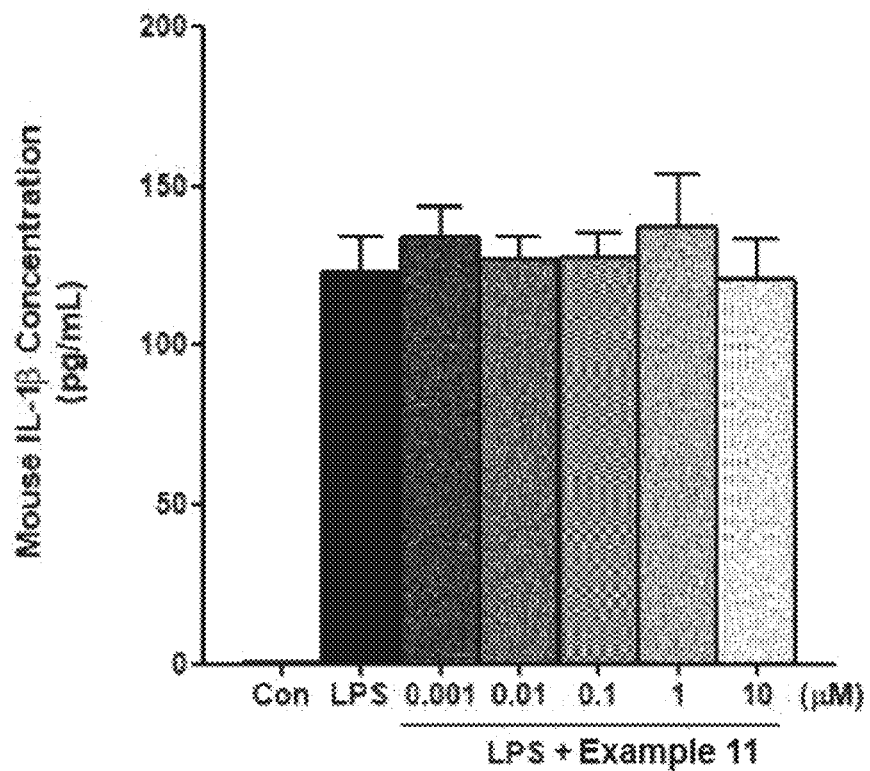
FIGS. 8a, 8b and 8c show results of measuring the expression levels of IL-1β, IL-6 and TNFα according to the treatment of Example 11 in LPS-stimulated macrophages, respectively.
Figure 8B:
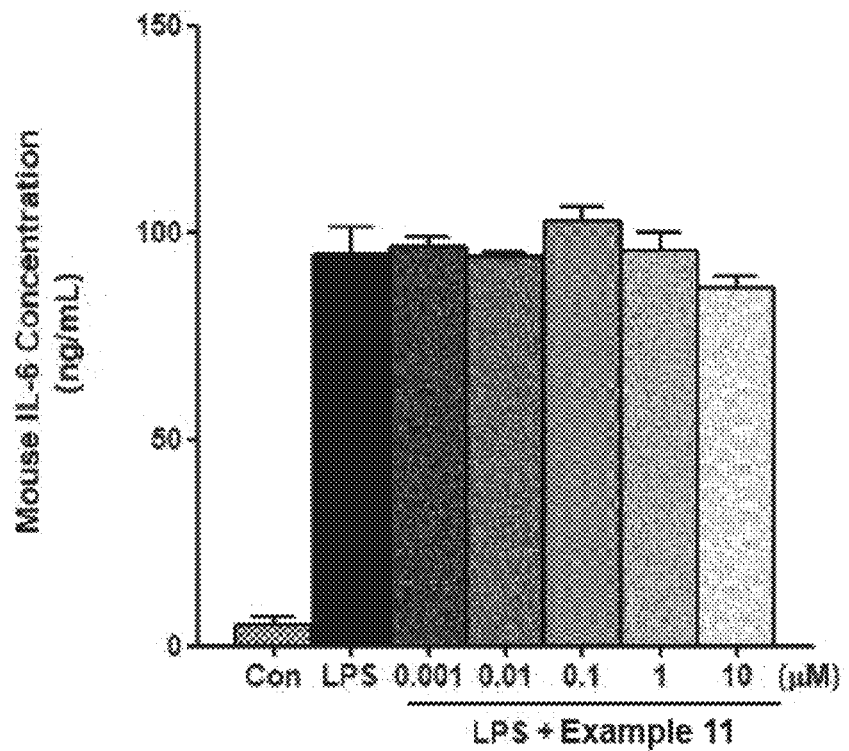
Figure 8C:
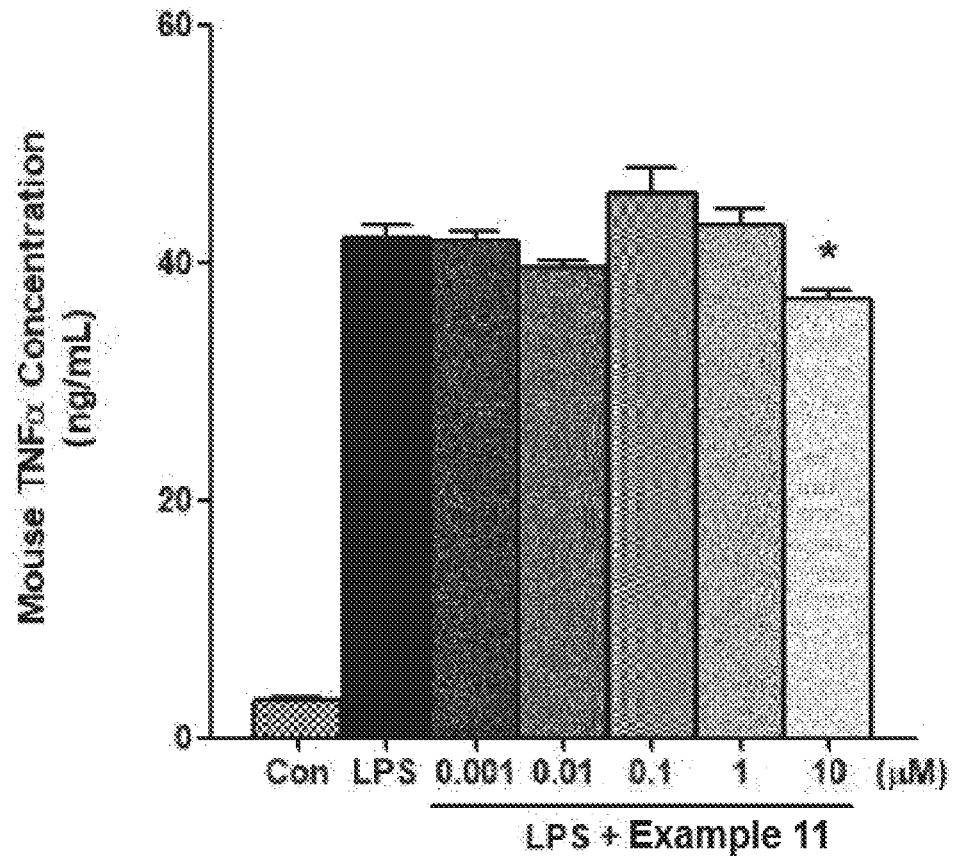

Referring to FIG. 8c, Example 11, which is a 6 mer, significantly reduced the TNFα level increased by LPS at a concentration of 10 µM.

Figure 9A:
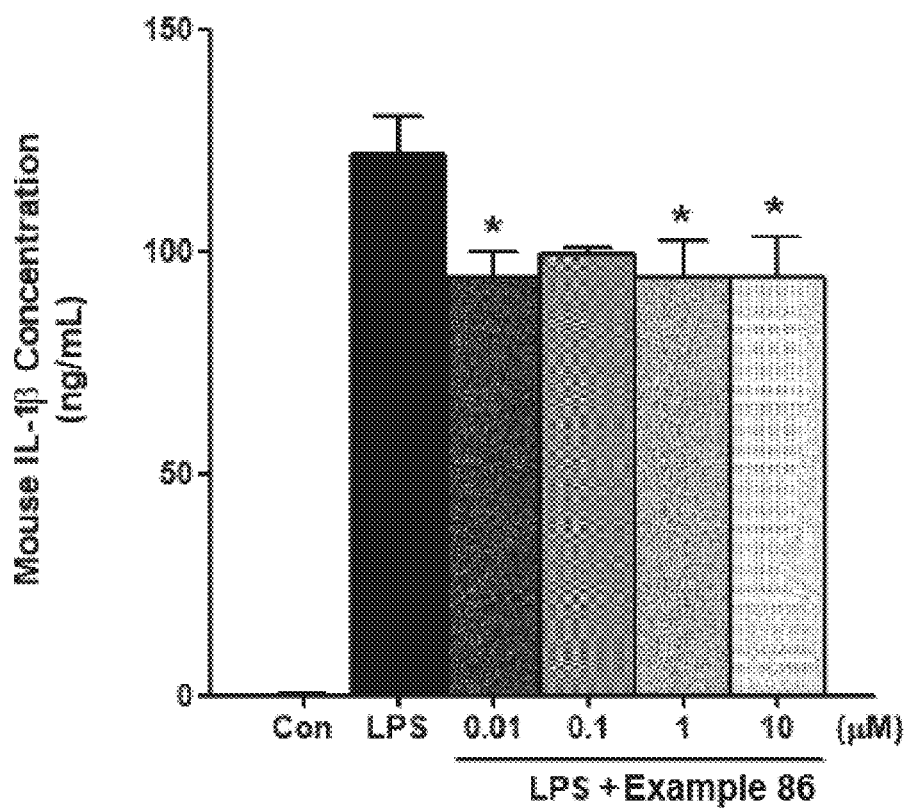
FIGS. 9a, 9b and 9c show results of measuring the expression levels of IL-1β, IL-6 and TNFα according to the treatment of Example 86 in LPS-stimulated macrophages, respectively.
Figure 9B:
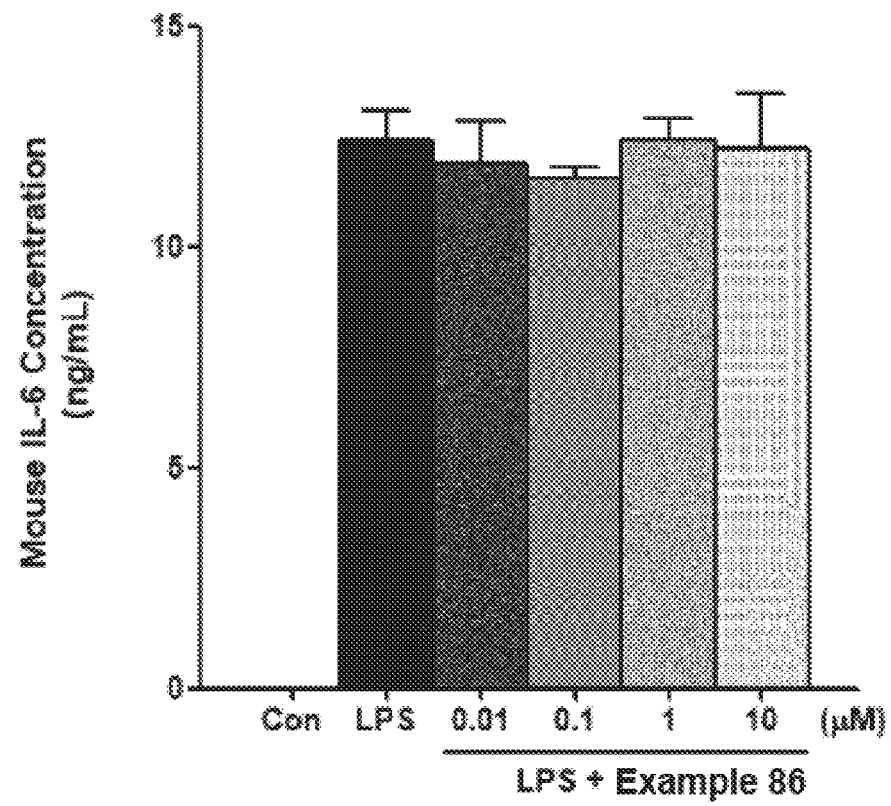
Figure 9C:
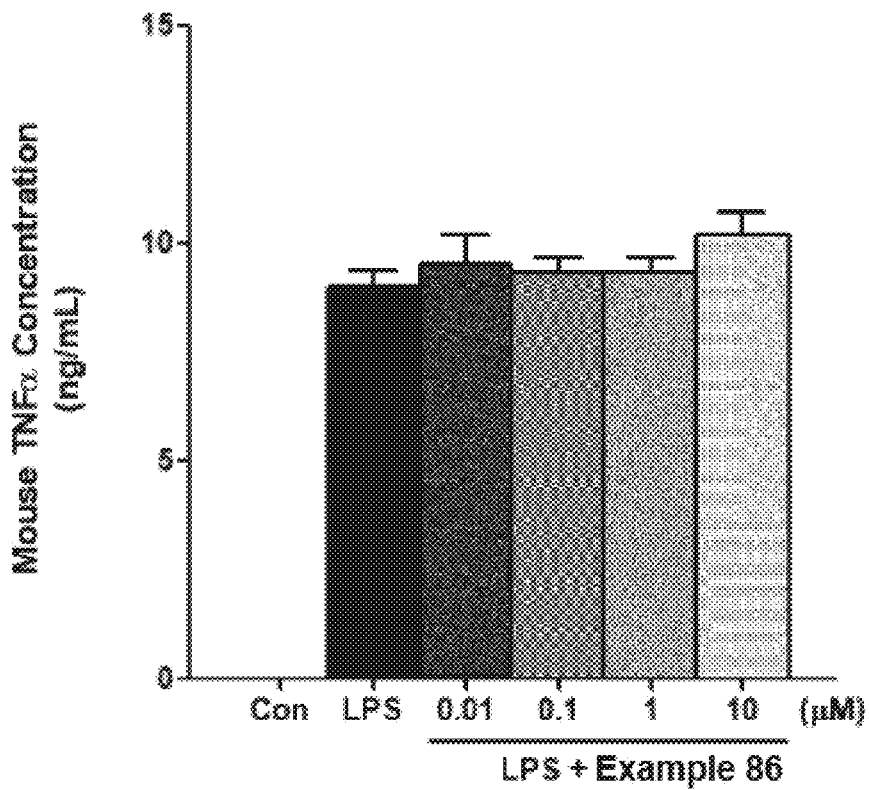

Referring to FIG. 9a, Example 86, which is a 7 mer, significantly reduced the IL-1β level increased by LPS at a concentration of 10 nM, 1 µM, and 10 µM.

Figure 10A:
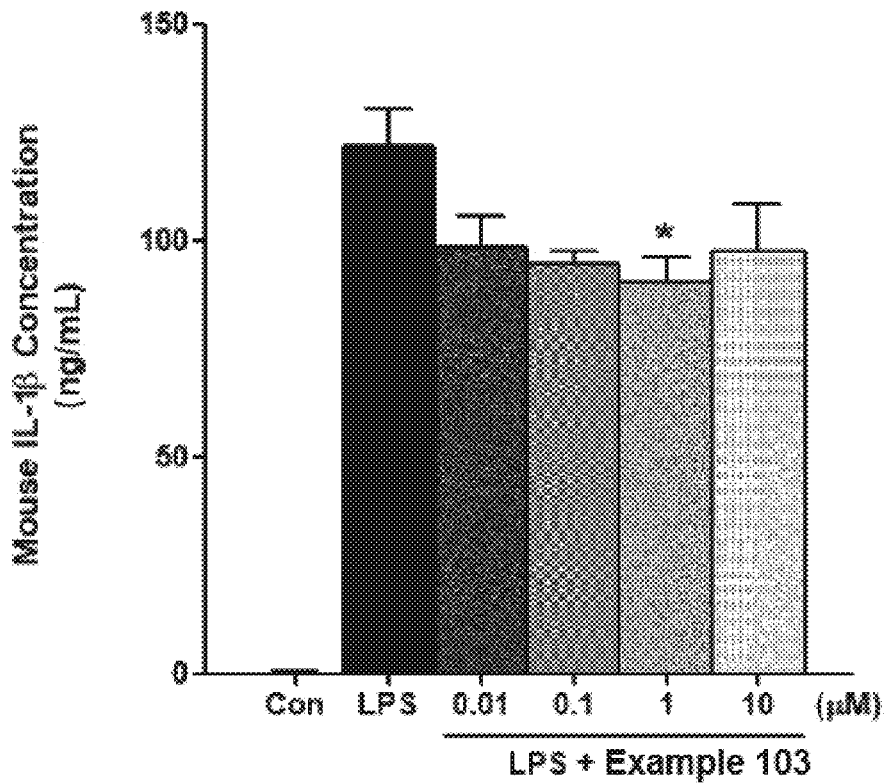
FIGS. 10a, 10b and 10c show results of measuring the expression levels of IL-1β, IL-6 and TNFα according to the treatment of Example 103 in LPS-stimulated macrophages, respectively.
Figure 10B:
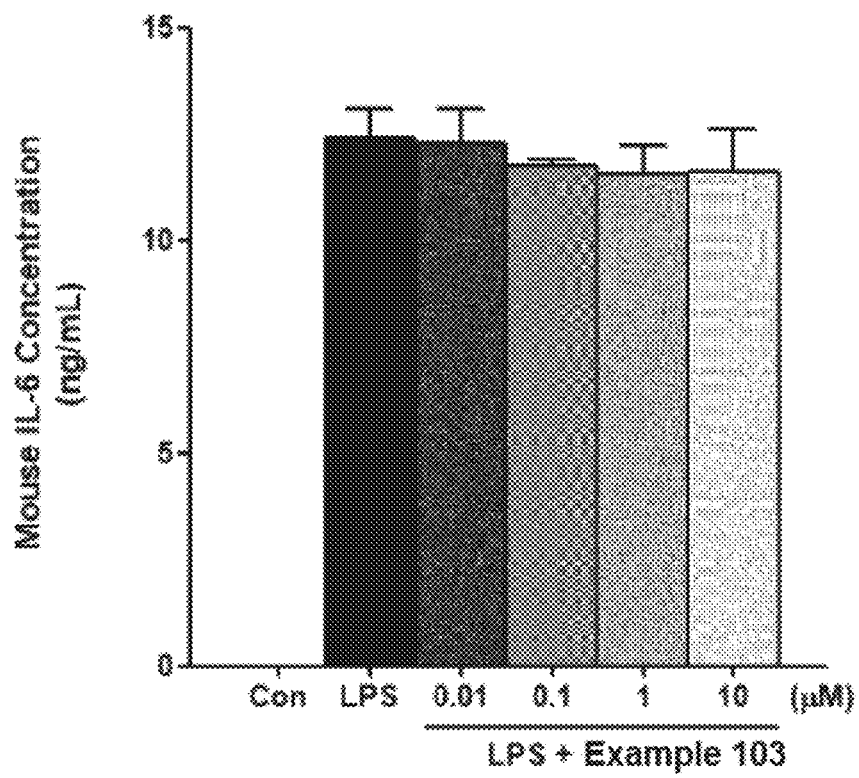
Figure 10C:
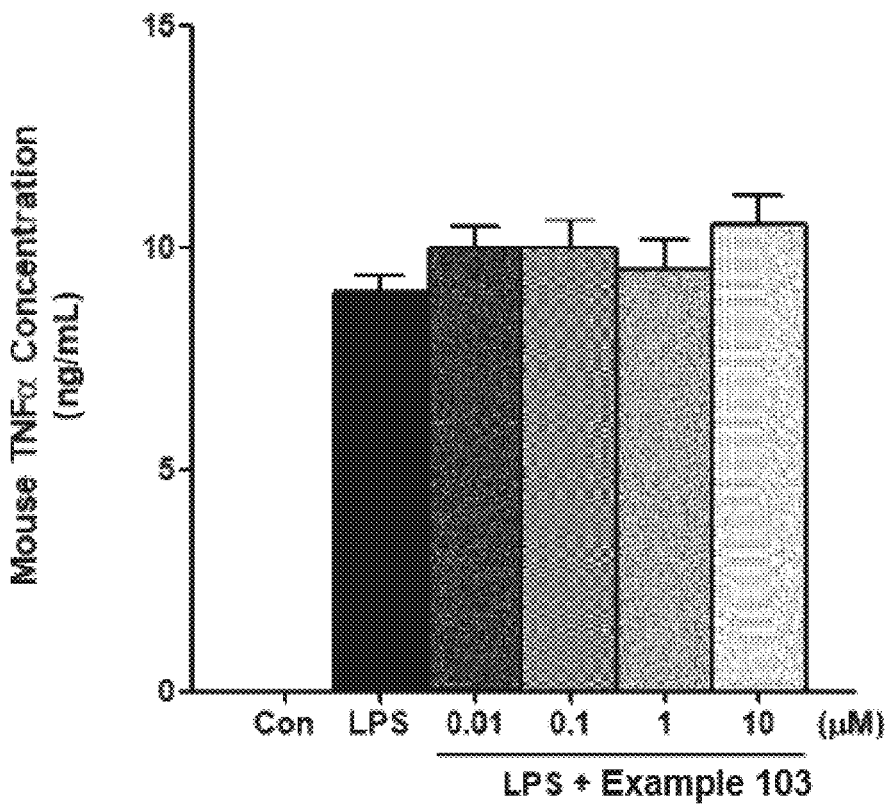

Referring to FIG. 10a, Example 103, which is a 8 mer, significantly reduced the IL-1β level increased by LPS at a concentration of 1 µM.

Figure 11A:
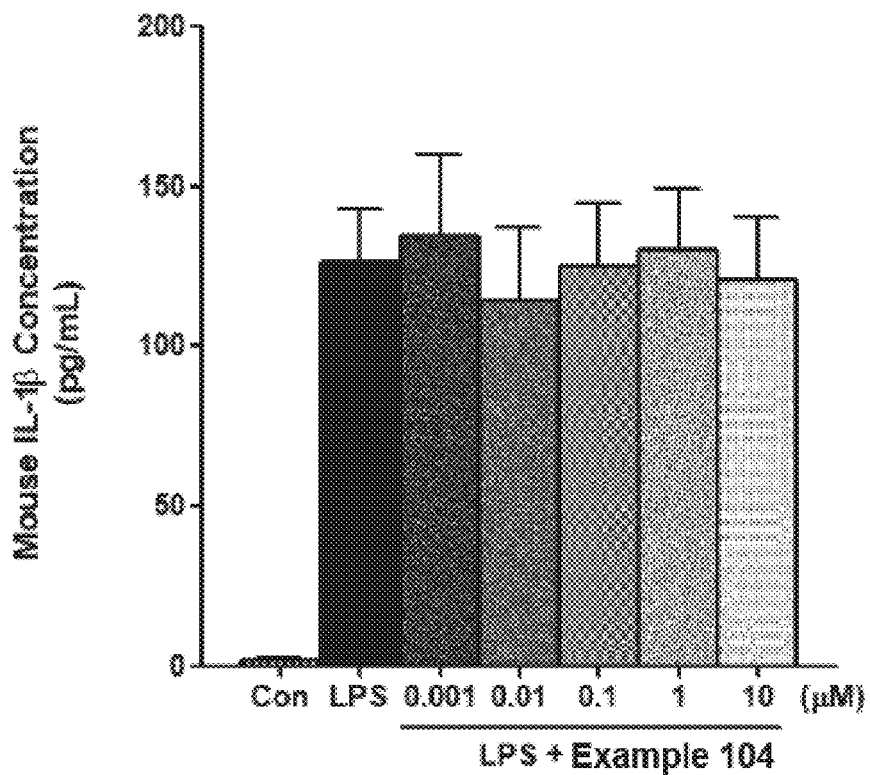
FIGS. 11a, 11b and 11c show results of measuring the expression levels of IL-1β, IL-6 and TNFα according to the treatment of Example 104 in LPS-stimulated macrophages, respectively.
Figure 11B:
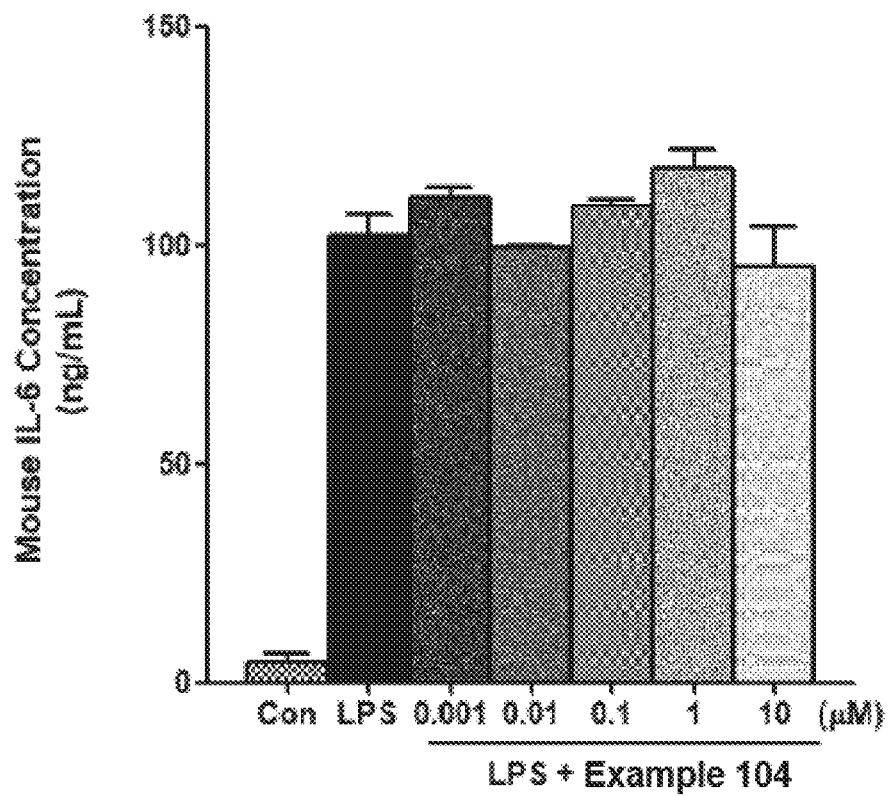
Figure 11C:
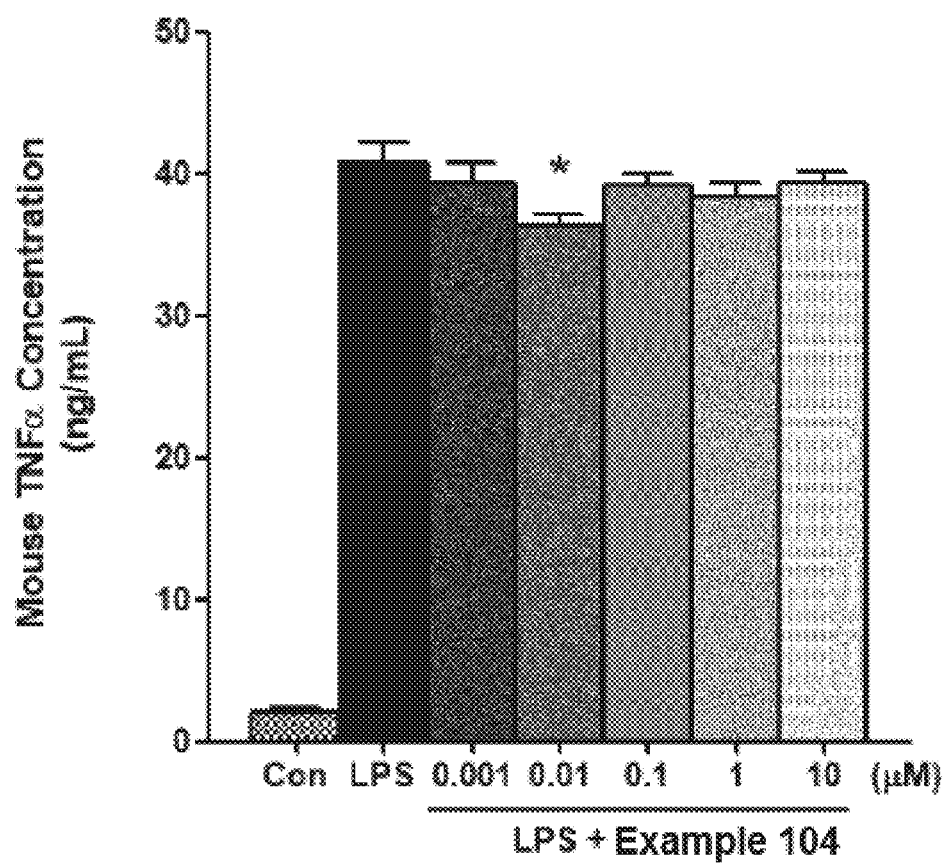

Referring to FIG. 11c, Example 104, which is a 8 mer, significantly reduced the TNFα level increased by LPS at a concentration of 10 nM.

That is, Examples 10, 32, 41, 55, 59, 86, 91 and 103, which are representative examples of the present invention, showed a significant anti-inflammatory effect by regulating the secretion of IL-1β secreted from immune cells, and Examples 30, 32, 41, and 91 showed a significant anti-inflammatory activity by regulating the secretion of IL-6, and Examples 10, 11, 59, and 104 showed a significant anti-inflammatory activity by regulating the secretion of TNFα, respectively.

Features, structures, effects, and the like described in the above-described embodiments are included in at least one embodiment of the present invention, and are not necessarily limited to only one embodiment. Furthermore, features, structures, effects, and the like illustrated in each embodiment can be combined or modified for other embodiments by those of ordinary skill in the art to which the embodiments belong. Therefore, the contents related to such combinations and modifications should be interpreted as being included in the scope of the present invention.

In addition, although the embodiments have been described above, these are merely examples and do not limit the present invention, and those of ordinary skill in the art to which the present invention belongs will appreciate that various modifications and applications not exemplified above are possible in a range that does not depart from the essential characteristics of the present embodiment. For example, each component specifically shown in the embodiments may be implemented by modification. In addition, differences related to such modifications and applications should be construed as being included in the scope of the present invention defined in the appended claims.

The invention claimed is:

1. A peptide or a pharmaceutically acceptable salt thereof, wherein the peptide is selected from the group consisting of:

Hyp-Gly-Gln-Glu-Leu-Leu-Ala, (SEQ ID NO.: 77)

Hyp-Gly-Gln-Glu-Val-Leu-Ala, and (SEQ ID NO.: 78)

Hyp-Gly-Gln-Glu-Aib-Leu-Ala. (SEQ ID NO.: 83)

2. A peptide or a pharmaceutically acceptable salt thereof, wherein the peptide comprises consists of the amino acid sequence Hyp-Gly-Gln-Glu-Aib-Leu-Ala. (SEQ ID NO.: 83)

3. A pharmaceutical composition for treating inflammation, comprising the peptide according to claim 1 as an active ingredient.

4. A food composition for ameliorating inflammation, comprising the peptide according to claim 1 as an active ingredient.

5. A cosmetic composition for ameliorating inflammation, comprising the peptide according to claim 1 as an active ingredient.

* * * * *

SEQUENCE LISTING

```
<160> NUMBER OF SEQ ID NOS: 116

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 1

Xaa Gly Gln Asp Gly
1               5

<210> SEQ ID NO 2
```

```
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 2

Xaa Gly Gln Asp Gly Leu
1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 3

Xaa Gly Gln Asp Gly Leu Ala
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 4

Xaa Gly Gln Ala Gly
1               5

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 5

Xaa Gly Gln Ala Gly Leu Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (1)..(1)
<223> OTHER INFORMATION: Xaa at position 1 is (2S,4R) trans-4-hydroxy-L-
      proline.

<400> SEQUENCE: 6

Xaa Gly Gln Asp Gly Leu Ala Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 7

Gln Asp Gly Leu Ala Gly Pro Lys
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 8

Xaa Gly Gln Leu Gly Leu Ala Gly
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 9

Gln Leu Gly Leu Ala Gly Pro Lys
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 10

Asp Gly Leu Ala Gly Pro Lys
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 11

Leu Gly Leu Ala Gly Pro Lys
1               5
```

```
<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 12

Xaa Gly Gln Asp Val
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: The X at position 1 is Trans-4-hydroxy-L-
      proline
<220> FEATURE:
<221> NAME/KEY: MISC_FEATURE
<222> LOCATION: (1)..(1)
<223> OTHER INFORMATION: The Xaa at position 1 is Trans-4-hydroxy-L-
      proline

<400> SEQUENCE: 13

Xaa Gly Gln Asp Val Leu
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 14

Xaa Gly Gln Asp Val Leu Ala
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 15

Xaa Gly Gln Asp Val Leu Ala Gly
1               5

<210> SEQ ID NO 16
```

```
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 16

Leu Ala Gly Pro Lys
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 17

Gly Leu Ala Gly Pro Lys
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 18

Xaa Gly Leu Ala Gly Pro Lys
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 19

Xaa Gly Gln Asp Gly Pro Lys
1               5

<210> SEQ ID NO 20
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 20

Gly Gln Asp Gly Leu Ala
1               5

<210> SEQ ID NO 21
<211> LENGTH: 6
<212> TYPE: PRT
<213> ORGANISM: Artificial Sequence
<220> FEATURE:
```

```
<223> OTHER INFORMATION: Synthetic Peptide

<400> SEQUENCE: 21

Gln Asp Gly Leu Ala Gly
1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 22

Asp Gly Leu Ala Gly Pro
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 23

Xaa Gly Gln Asp Leu
1               5

<210> SEQ ID NO 24
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 24

Xaa Gly Gln Asp Ala
1               5

<210> SEQ ID NO 25
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 25

Xaa Gly Gln Asp Val Leu
1               5

<210> SEQ ID NO 26
<211> LENGTH: 6
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 26

Xaa Gly Gln Asp Leu Leu
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 27

Xaa Gly Gln Asp Ala Leu
1               5

<210> SEQ ID NO 28
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 28

Xaa Gly Gln Asp Val Leu Ala
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 29

Xaa Gly Gln Asp Leu Leu Ala
1               5

<210> SEQ ID NO 30
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
```

```
<400> SEQUENCE: 30

Xaa Gly Gln Asp Ala Leu Ala
1               5

<210> SEQ ID NO 31
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is trans-4-Hydroxy-D-proline.

<400> SEQUENCE: 31

Xaa Gly Gln Asp Gly
1               5

<210> SEQ ID NO 32
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is cis-4-fluoro-L-proline.

<400> SEQUENCE: 32

Xaa Gly Gln Asp Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is trans-4-amino-L-proline.

<400> SEQUENCE: 33

Xaa Gly Gln Asp Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is 4-difluoro-L-proline.

<400> SEQUENCE: 34

Xaa Gly Gln Asp Gly
1               5

<210> SEQ ID NO 35
<211> LENGTH: 5
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is 4-methylene-L-proline.

<400> SEQUENCE: 35

Xaa Gly Gln Asp Gly
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is trans-4-Hydroxy-D-proline.

<400> SEQUENCE: 36

Xaa Gly Gln Asp Gly Leu
1               5

<210> SEQ ID NO 37
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is cis-4-fluoro-L-proline.

<400> SEQUENCE: 37

Xaa Gly Gln Asp Gly Leu
1               5

<210> SEQ ID NO 38
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is trans-4-amino-L-proline.

<400> SEQUENCE: 38

Xaa Gly Gln Asp Gly Leu
1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is 4-difluoro-L-proline.

<400> SEQUENCE: 39

Xaa Gly Gln Asp Gly Leu
1               5
```

```
<210> SEQ ID NO 40
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is 4-methylene-L-proline.

<400> SEQUENCE: 40

Xaa Gly Gln Asp Gly Leu
1               5

<210> SEQ ID NO 41
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is trans-4-hydroxy-D-proline.

<400> SEQUENCE: 41

Xaa Gly Gln Asp Gly Leu Ala
1               5

<210> SEQ ID NO 42
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is cis-4-fluoro-L-proline.

<400> SEQUENCE: 42

Xaa Gly Gln Asp Gly Leu Ala
1               5

<210> SEQ ID NO 43
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is trans-4-amino-L-proline.

<400> SEQUENCE: 43

Xaa Gly Gln Asp Gly Leu Ala
1               5

<210> SEQ ID NO 44
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
```

```
<223> OTHER INFORMATION: Xaa at position 1 is 4-difluoro-L-proline.

<400> SEQUENCE: 44

Xaa Gly Gln Asp Gly Leu Ala
1               5

<210> SEQ ID NO 45
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is 4-methylene-L-proline.

<400> SEQUENCE: 45

Xaa Gly Gln Asp Gly Leu Ala
1               5

<210> SEQ ID NO 46
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is 4,4-dimethyl-L-proline.

<400> SEQUENCE: 46

Xaa Gly Gln Asp Gly
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is 4,4-dimethyl-L-proline.

<400> SEQUENCE: 47

Xaa Gly Gln Asp Gly Leu
1               5

<210> SEQ ID NO 48
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is 4,4-dimethyl-L-proline.

<400> SEQUENCE: 48

Xaa Gly Gln Asp Gly Leu Ala
1               5

<210> SEQ ID NO 49
<211> LENGTH: 5
<212> TYPE: PRT
```

```
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (3)..(3)
<223> OTHER INFORMATION: Xaa at position 3 is D-glutamine.

<400> SEQUENCE: 49

Xaa Gly Xaa Asp Gly
1               5

<210> SEQ ID NO 50
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is D-aspartic acid.

<400> SEQUENCE: 50

Xaa Gly Gln Xaa Gly
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (3)..(3)
<223> OTHER INFORMATION: Xaa at position 3 is D-glutamine.

<400> SEQUENCE: 51

Xaa Gly Xaa Asp Gly Leu
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is D-aspartic acid.
```

```
<400> SEQUENCE: 52

Xaa Gly Gln Xaa Gly Leu
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (6)..(6)
<223> OTHER INFORMATION: Xaa at position 6 is D-leucine.

<400> SEQUENCE: 53

Xaa Gly Gln Asp Gly Xaa
1               5

<210> SEQ ID NO 54
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (3)..(3)
<223> OTHER INFORMATION: Xaa at position 3 is D-glutamine.

<400> SEQUENCE: 54

Xaa Gly Xaa Asp Gly Leu Ala
1               5

<210> SEQ ID NO 55
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is D-aspartic acid.

<400> SEQUENCE: 55

Xaa Gly Gln Xaa Gly Leu Ala
1               5

<210> SEQ ID NO 56
<211> LENGTH: 7
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (6)..(6)
<223> OTHER INFORMATION: Xaa at position 6 is D-leucine.

<400> SEQUENCE: 56

Xaa Gly Gln Asp Gly Xaa Ala
1               5

<210> SEQ ID NO 57
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (7)..(7)
<223> OTHER INFORMATION: Xaa at position 7 is D-alanine.

<400> SEQUENCE: 57

Xaa Gly Gln Asp Gly Leu Xaa
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 58

Xaa Gly Gln Glu Gly
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 59

Xaa Gly Gln Glu Gly Leu
1               5

<210> SEQ ID NO 60
<211> LENGTH: 7
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 60

Xaa Gly Gln Glu Gly Leu Ala
1               5

<210> SEQ ID NO 61
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 61

Gln Glu Gly Leu Ala Gly
1               5

<210> SEQ ID NO 62
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 62

Xaa Gly Gln Asp Gly Val
1               5

<210> SEQ ID NO 63
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 63

Xaa Gly Gln Asp Gly Val Ala
1               5

<210> SEQ ID NO 64
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 64

Xaa Ala Gln Asp Gly
1               5
```

```
<210> SEQ ID NO 65
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 65

Xaa Val Gln Asp Gly
1               5

<210> SEQ ID NO 66
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 66

Xaa Leu Gln Asp Gly
1               5

<210> SEQ ID NO 67
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 67

Pro Gly Gln Asp Gly
1               5

<210> SEQ ID NO 68
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 68

Pro Gly Gln Asp Gly Leu
1               5

<210> SEQ ID NO 69
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 69

Pro Gly Gln Asp Gly Leu Ala
1               5

<210> SEQ ID NO 70
<211> LENGTH: 7
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 70

Xaa Gly Gln Asn Gly Leu Ala
1               5

<210> SEQ ID NO 71
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 71

Xaa Gly Gln His Gly Leu Ala
1               5

<210> SEQ ID NO 72
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 72

Xaa Gly Gln Asn Gly Leu
1               5

<210> SEQ ID NO 73
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 73

Xaa Gly Gln His Gly Leu
1               5

<210> SEQ ID NO 74
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
```

```
<220> FEATURE:
<221> NAME/KEY: MISC_FEATURE
<222> LOCATION: (5)..(5)
<223> OTHER INFORMATION: Xaa at position 5 is 2-aminoisobutyric acid.

<400> SEQUENCE: 74

Xaa Gly Gln Asp Xaa Leu Ala
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is 2-aminoisobutyric acid.

<400> SEQUENCE: 75

Xaa Gly Gln Xaa Gly Leu
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (5)..(5)
<223> OTHER INFORMATION: Xaa at position 5 is 2-aminoisobutyric acid.

<400> SEQUENCE: 76

Xaa Gly Gln Asp Xaa
1               5

<210> SEQ ID NO 77
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 77

Xaa Gly Gln Glu Leu Leu Ala
1               5

<210> SEQ ID NO 78
<211> LENGTH: 7
<212> TYPE: PRT
<213> ORGANISM: Artificial Sequence
<220> FEATURE:
<223> OTHER INFORMATION: Synthetic Peptide
```

```
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 78

Xaa Gly Gln Glu Val Leu Ala
1               5

<210> SEQ ID NO 79
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 79

Xaa Gly Gln Glu Leu Leu
1               5

<210> SEQ ID NO 80
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 80

Xaa Gly Gln Glu Val Leu
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 81

Xaa Gly Gln Glu Leu
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 82
```

```
Xaa Gly Gln Glu Val
1               5

<210> SEQ ID NO 83
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (5)..(5)
<223> OTHER INFORMATION: Xaa at position 5 is 2-aminoisobutyric acid.

<400> SEQUENCE: 83

Xaa Gly Gln Glu Xaa Leu Ala
1               5

<210> SEQ ID NO 84
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (5)..(5)
<223> OTHER INFORMATION: Xaa at position 5 is L-a-tert-butylglycine.

<400> SEQUENCE: 84

Xaa Gly Gln Glu Xaa Leu Ala
1               5

<210> SEQ ID NO 85
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline
<220> FEATURE:
<221> NAME/KEY: MISC_FEATURE
<222> LOCATION: (5)..(5)
<223> OTHER INFORMATION: Xaa at position 5 is phenylglycine.

<400> SEQUENCE: 85

Xaa Gly Gln Glu Xaa Leu Ala
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (1)..(1)
<223> OTHER INFORMATION: Xaa at position 1 is (2S,4R) trans-4-hydroxy-L-
      proline.

<400> SEQUENCE: 86

Xaa Gly Gln Leu Val
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 87

Xaa Gly Gln Leu Leu Leu Ala
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 88

Xaa Gly Gln Leu Val Leu Ala
1               5

<210> SEQ ID NO 89
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 89

Xaa Gly Gln Leu Leu Leu
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 90

Xaa Gly Gln Leu Val Leu
```

```
<210> SEQ ID NO 91
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is apartimide or
      aminosuccinimide.

<400> SEQUENCE: 91

Xaa Gly Gln Xaa Gly
1               5

<210> SEQ ID NO 92
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is apartimide or
      aminosuccinimide.

<400> SEQUENCE: 92

Xaa Gly Gln Xaa Gly Leu
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is apartimide or
      aminosuccinimide.

<400> SEQUENCE: 93

Xaa Gly Gln Xaa Gly Leu Ala
1               5

<210> SEQ ID NO 94
<211> LENGTH: 8
<212> TYPE: PRT
<213> ORGANISM: Artificial Sequence
<220> FEATURE:
<223> OTHER INFORMATION: Synthetic Peptide
<220> FEATURE:
```

```
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is apartimide or
      aminosuccinimide

<400> SEQUENCE: 94

Xaa Gly Gln Xaa Gly Leu Ala Gly
1               5

<210> SEQ ID NO 95
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa at position 2 is apartimide or
      aminosuccinimide.

<400> SEQUENCE: 95

Gln Xaa Gly Leu Ala Gly Pro Lys
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is apartimide or
      aminosuccinimide.

<400> SEQUENCE: 96

Xaa Gly Leu Ala Gly Pro Lys
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (5)..(5)
<223> OTHER INFORMATION: Xaa at position 5 is glycine substituted with
      isopropyl ester.

<400> SEQUENCE: 97

Xaa Gly Gln Asp Xaa
1               5

<210> SEQ ID NO 98
<211> LENGTH: 6
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (6)..(6)
<223> OTHER INFORMATION: Xaa at position 6 is leucine substituted with
      isopropyl ester.

<400> SEQUENCE: 98

Xaa Gly Gln Asp Gly Xaa
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (7)..(7)
<223> OTHER INFORMATION: Xaa at position 7 is alanine substituted with
      isopropyl ester.

<400> SEQUENCE: 99

Xaa Gly Gln Asp Gly Leu Xaa
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is apartimide or
      aminosuccinimide.
<220> FEATURE:
<221> NAME/KEY: MISC_FEATURE
<222> LOCATION: (5)..(5)
<223> OTHER INFORMATION: Xaa at position 5 is glycine substituted with
      isopropyl ester.

<400> SEQUENCE: 100

Xaa Gly Gln Xaa Xaa
1               5

<210> SEQ ID NO 101
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
```

```
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is aspartic acid substituted
      with isopropyl ester.
<220> FEATURE:
<221> NAME/KEY: MISC_FEATURE
<222> LOCATION: (5)..(5)
<223> OTHER INFORMATION: Xaa at position 5 is glycine substituted with
      isopropyl ester.

<400> SEQUENCE: 101

Xaa Gly Gln Xaa Xaa
1               5

<210> SEQ ID NO 102
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is apartimide or
      aminosuccinimide.
<220> FEATURE:
<221> NAME/KEY: MISC_FEATURE
<222> LOCATION: (6)..(6)
<223> OTHER INFORMATION: Xaa at position 6 is leucine substituted with
      isopropyl ester.

<400> SEQUENCE: 102

Xaa Gly Gln Xaa Gly Xaa
1               5

<210> SEQ ID NO 103
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is aspartic acid substituted
      with isopropyl ester.
<220> FEATURE:
<221> NAME/KEY: MISC_FEATURE
<222> LOCATION: (6)..(6)
<223> OTHER INFORMATION: Xaa at position 6 is leucine substituted with
      isopropyl ester.

<400> SEQUENCE: 103

Xaa Gly Gln Xaa Gly Xaa
1               5

<210> SEQ ID NO 104
<211> LENGTH: 7
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is apartimide or
      aminosuccinimide.
<220> FEATURE:
<221> NAME/KEY: MISC_FEATURE
<222> LOCATION: (7)..(7)
<223> OTHER INFORMATION: Xaa at position 7 is alanine substituted with
      isopropyl ester.

<400> SEQUENCE: 104

Xaa Gly Gln Xaa Gly Leu Xaa
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is aspartic acid substituted
      with isopropyl ester.
<220> FEATURE:
<221> NAME/KEY: MISC_FEATURE
<222> LOCATION: (7)..(7)
<223> OTHER INFORMATION: Xaa at position 7 is alanine substituted with
      isopropyl ester.

<400> SEQUENCE: 105

Xaa Gly Gln Xaa Gly Leu Xaa
1               5

<210> SEQ ID NO 106
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is aspartic acid substituted
      with isopropyl ester.

<400> SEQUENCE: 106

Xaa Gly Gln Xaa Gly
1               5

<210> SEQ ID NO 107
<211> LENGTH: 6
<212> TYPE: PRT
<213> ORGANISM: Artificial Sequence
```

```
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is aspartic acid substituted
      with isopropyl ester.

<400> SEQUENCE: 107

Xaa Gly Gln Xaa Gly Leu
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is aspartic acid substituted
      with isopropyl ester.

<400> SEQUENCE: 108

Xaa Gly Gln Xaa Gly Leu Ala
1               5

<210> SEQ ID NO 109
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (2)..(2)
<223> OTHER INFORMATION: Xaa at position 2 is apartimide or
      aminosuccinimide.

<400> SEQUENCE: 109

Gln Xaa Gly Leu Ala Gly
1               5

<210> SEQ ID NO 110
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 110

Xaa Gly Gln Ala Val
1               5

<210> SEQ ID NO 111
```

```
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 111

Xaa Gly Gln Ala Leu
1               5

<210> SEQ ID NO 112
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 112

Xaa Gly Gln Leu Leu
1               5

<210> SEQ ID NO 113
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 113

Xaa Gly Gln Ala Gly Leu
1               5

<210> SEQ ID NO 114
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.

<400> SEQUENCE: 114

Xaa Gly Gln Ala Leu Leu
1               5

<210> SEQ ID NO 115
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
```

```
<222> LOCATION: (1)..(1)
<223> OTHER INFORMATION: Xaa at position 1 is (2S,4R) trans-4-hydroxy-L-
      proline.

<400> SEQUENCE: 115

Xaa Gly Gln Ala Val Leu
1               5

<210> SEQ ID NO 116
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa at position 1 is (2S,4R) trans-4-hydroxy-L-
      proline.
<220> FEATURE:
<221> NAME/KEY: MISC_FEATURE
<222> LOCATION: (4)..(4)
<223> OTHER INFORMATION: Xaa at position 4 is D-aspartic acid.

<400> SEQUENCE: 116

Xaa Gly Gln Xaa Leu
1               5
```

UNITED STATES PATENT AND TRADEMARK OFFICE
CERTIFICATE OF CORRECTION

| | | |
|---|---|---|
| PATENT NO. | : 12,428,446 B2 | Page 1 of 1 |
| APPLICATION NO. | : 17/613176 | |
| DATED | : September 30, 2025 | |
| INVENTOR(S) | : Kim et al. | |

It is certified that error appears in the above-identified patent and that said Letters Patent is hereby corrected as shown below:

In the Claims

In Column 117, Claim 2, Line 42, please delete "comprises" before "consists of".

Signed and Sealed this
Thirteenth Day of January, 2026

John A. Squires
*Director of the United States Patent and Trademark Office*